US007569543B2

(12) United States Patent
Yu

(10) Patent No.: US 7,569,543 B2
(45) Date of Patent: Aug. 4, 2009

(54) COMPOSITIONS OF ANGIOPOIETIN, FRAGMENTS, MUTANTS AND ANALOGS THEREOF AND USES OF THE SAME

(75) Inventor: Qin Yu, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/789,222

(22) Filed: Feb. 27, 2004

(65) Prior Publication Data

US 2004/0186054 A1 Sep. 23, 2004

Related U.S. Application Data

(60) Provisional application No. 60/450,582, filed on Feb. 27, 2003.

(51) Int. Cl.
*A61K 38/00* (2006.01)
(52) U.S. Cl. .................. 514/12; 530/350; 530/300; 530/324; 514/8; 514/2
(58) Field of Classification Search ............ None
See application file for complete search history.

(56) References Cited

U.S. PATENT DOCUMENTS 6,441,137 B1 * 8/2002 Davis et al. ............ 530/350

OTHER PUBLICATIONS

Folkman, "Tumor angiogenesis: therapeutic implications," New. Eng. J. Med. (1971) 285:1182-1186.
Risau, "Mechanisms of angiogenesis," Nature (1997) 386:671-674.
Kim, et al., "Inhibition of vascular endothelial growth factor-induced angiogenesis suppresses tumor growth in vivo," Nature (1993) 362:841-844.
Hanahan and Folkman, "Patterns and emerging mechanisms fo the angiogenic switch during tumorigenesis," Cell (1996) 86:353-364.
Hanahan, "Signalling vascular morhogenesis and maintenance," Science (1997) 277:48-50.
Hanahan and Weinberg, "The hallmarks of cancer," Cell (2000) 100:57-70.
Folkman and D'Amore, "Blood vessel formation: what is its molecular basis?", Cell (1996) 87:1153-1155.
Yancopoulos, et al., "Vascular-specific growth factors and blood vessel formation," Nature (2000) 407:242-248.
Ingber and Folkman, "How does extracellular matrix control capillary morphogenesis?", Cell (1989) 58:803-805.
Ramsauer and D'Amore, "Getting tie(2)d up in angiogenesis," J. Clin. Investig. (2002) 110:1615-1617.
Betsholtz, et al., "Developmental roles of platelet-derived growth factors," BioEssays (2001) 23:494-507.
Fong, et al., "Role of the Flt-1 receptor tyrosine kinase in regulating the assembly of vascular endothelium," Nature (1995) 376:66-70.
Maisonpierre, et al., "Angiopoietin-2, a natural antagonist for tie2 that disrupts in vivo angiogenesis," Science (1997) 277:55-60.

Sato, et al., "tie-1 and tie-2 define another class of putative receptor tyrosine kinase genes expressed in early embryonic vascular system," Proc. Natl. Acad. Sci. USA (1993) 90:9355-9358.
Schnurch and Risau, "Expression of the tie-2, a member of a novel family of receptor tyrosine kinases, in the endothelial cell lineage," Development (1993) 119:957-968.
Dumont, et al., "Dominant-negative and targeted null mutations in the endothelial receptor tyrosine kinase, tek, reveal a critical role in vasculogenesis of the embryo," Genes Dev. (1994) 8:1897-1909.
Coogan, et al., "Expression of tie2/tek in breast tumor vasculature provides a new marker for evaluation of tumor angiogenesis," Br. J. Cancer (1998) 77:51-56.
Sato, et al., "Distinct roles of the receptor tyrosine kinases tie-1 and tie-2 in blood vessel formation," Nature (1995) 376:70-74.
Suri, et al., "Requisite role of angiopoietin-1, a ligand for the Tie2 receptor during embryonic angiogenesis," Cell (1996) 87:1171-1180.
Gale and Yancopoulos, "Growth factors acting via endothelial cell-specific receptor tyrosine kinases: VEGFs, angiopoietins, and ephrins in vascular development," Genes Dev. (1999) 13:1055-1066.
Suri, et al., "Increased vascularization in mice overexpressing angiopoietin-1," Science (1998) 282:468-471.
Thurston, et al., "Leakage-resistant blood vessels in mice transenically overexpressing angiopoietin-1," Science (1999) 286:2511-2514.
Thurston, et al., "Angiopoietin-1 protects the adult vasculature against plasma leakage," Nature Med. (2000) 6:460-463.
Stratmann, et al., "Cell type-specific expression of angiopoietin-1 and angiopoietin-2 suggests a role in glioblastoma angiogenesis," Am. J. Pathol. (1998) 153:1459-1468.
Witzenbichler, et al., "Chemotactic properties of angiopoietin-1 and -2, ligands for the endothelial-specific receptor tyrosine kinase tie2.," J. Biol. Chem. (1998) 273:18514-18521.
Carlson, et al., "Direct cell adhesion to the angiopoietins mediated by integrins," J. Biol. Chem. (2001) 276:26516-26525.
Papapetropoulos, et al., "Angiopoietin-1 inhibits endothelial cell apoptosis via the Akt/survivin pathway," J. Biol. Chem. (2000) 275:9102-9105.
Kim, et al., "Angiopoietin-1 regulates endothelial cell survival through the phosphatidylinositol 3'-kinase/Akt signal transduction pathway," Circulation Res. (2000) 86:24-29.
Hayes, et al., "Angiopoietin-1 and its receptor Tie-2 participate in the regulation of capillary-like tubulin formation and survival of endothelial cells," Microvasc. Res. (1999) 58:224-237.
Oh, et al., "Hypoxia and vascular endothelial growth factor selectively upregulate angiopoietin-2 in bovine microvascular endothelial cells," J. Biol. Chem. (1999) 274:15732-15739.
Mandriota and Pepper, "Regulation of angiopoietin-2 mRNA levels in bovine microvascular endothelial cells by cytokines and hypoxia," Circulation Res. (1998) 83:852-859.
Kim, et al., "Tumor necrosis factor-alpha upregulates angiopoietin-2 in human umbilical vein endothelial cells," Biochem. Biophys. Res. Comm. (2000) 269:361-365.

(Continued)

*Primary Examiner*—Hope A Robinson
(74) *Attorney, Agent, or Firm*—Pepper Hamilton LLP

(57) ABSTRACT

The present invention relates to Ang-1, Ang-2, and Ang-3, and to methods and uses of the same. The present invention also relates to ECM-binding fragments, non-ECM-binding fragments, proteolytic resistant fragments and C-terminal fragments of Ang-1, and to methods and uses of the same.

2 Claims, 8 Drawing Sheets

OTHER PUBLICATIONS

Kim, et al., "Angiopoietin-1 induces endothelial cell sprouting through the activation of focal adhesion kinase and plasmin secretion," Circulation Res. (2000) 86:952-959.
Valenzuela, et al., "Angiopoietins 3 and 4: diverging gene counterparts in mice and humans," Proc. Natl. Acad. Sci. USA (1999) 96:1904-1909.
Siemeister, et al., "Two independent mechanisms essential for tumor angiogenesis: inhibition fo human melanoma xenograft growth by interfering with eiter the vascular endothelial growth factor receptor pathway of the tie-2 pathway," Cancer Res. (1999) 59:3185-3193.
Millauer, et al., "Glioblastoma growth inhibited in vivo by a dominant-negative Flk-1 mutant," Nature (1994) 367:576-579.
Goldman, et al., "Paracrine expression of a native soluble vascular endothelial growth factor receptor inhibits tumor growth, metastsis, and mortality rate," Proc. Natl. Acad. Sci. USA (1998) 95:8795-8800.
Ahmad, et al., "The effects of angiopoietin-1 and -2 on tumor growth and angiogenesis in human colon cancer," Cancer Res. (2001) 61:1255-1259.
Etoh, et al., "Angiopoietin-2 is related to tumor angiogenesis in gastric carcinoma:possible in vivo regulation via induction of proteases," Cancer Res. (2001) 61:2145-2153.
Hawighorst, et al., "Activation of the tie2 receptor by angiopoietin-1 enhances tumor vessel maturation nad impairs squamous cell carcinoma growth," Am. J. Pathol. (2002) 100:1381-1392.
Koga, et al., "Expression of angiopoietin-2 in human glioma cells and its role for angiogenesis," Cancer Res. (2001) 61:6248-6254.
Papetti and Herman, "Mechanisms of normal and tumor-derived angiogenesis," Am. J. Physiol. Cell Physiol. (2002) 282:C947-C970.
Teichert-Kuliszewska, et al., "Biological action of angiopoietin-2 in a fibrin matrix model of angiogenesis is associated with activation if Tie2," Cardiovasc. Res. (2001) 49:659-670.
Yu and Stamenkovic, "Localization of matrix metalloproteinase 9 to the cell surface provides a mechanism for CD44-mediated tumor invasion," Genes Dev. (1999) 13:35-48.
Hungerford and Little, "Developmental biology of the vascular smooth muscle cell: building a multilayed vessel wall," J. Vasc. Res. (1999) 36:2-27.
Gale, et al., "Angiopoietin-2 is required for postnatal angiogenesis and lymphatic patterning, and only the latter role is rescued by angiopoietin-1," Devel. Cell (2002) 3:411-423.
Shyu, et al., "Direct intramuscular injection of plasmid DNA encoding angiopoietin-1 but not angiopoietin-2 augments revascularization in the rabbit ischemic hindlimb," Circulation (1998) 98:2081-2087.
Kim, et al., "Angiopoietin-2 at high concentration can enhance endothelial cell survival through the phosphatidylinositol 3'-kinase/Akt signal transduction pathway," Oncogene (2000) 19:4549-4552.
Lander and Selleck, "The elusive functions of proteoglycans: in vivo veritas," J. Cell Biol. (2000) 148:227-232.
Iozzo, "Matrix metalloproteins: from molecular design to cellular function," Ann. Rev. Biochem. (1998) 67:609-652.
Iozzo and San Antonio, "Heparan sulfate proteoglycans: heavy hitters in the angiogenesis arena," J. Clin. Investig. (2001) 108:349-355.
Fiedler, et al., "Angiopoietin-1 and angiopoietin-2 share the same binding domains in the tie-2 receptor involving the first Ig-like loop and the epidermal growth factor-like repeats," J. Biol. Chem. (2003) 278:1721-1727.
Yu, et al., "Induction of apoptosis of metastatic mammary carcinoma cells in vivo by disruption of tumor cell surface CD44 function," J. Exp. Med. (1997) 186:1985-1996.
Kontos, et al., "Tyrosine 1011 of tie2 is the major site of association of p85 and is required for activation of phosphatidylinositol 3-kinase and Akt," Mol. Cell. Biol. (1998) 18:4131-4140.
Fidler and Ellis, "The implications of angiogenesis for the biology and therapy of cancer metastasis," Cell (1994) 79:185-188.
Fidler, "Angiogenetic heterogeneity: regulation of neoplastic angiogenesis by the organ microenvironment," J. Natl. Cancer Inst. (2001) 93:1040-1041.
Ali, et al., "Estrogen receptor-alpha in the inhibition of cancer growth and angiogenesis," Cancer Res. (2000) 60:7094-7098.
Nokihara, et al., "Natural killer cell-dependent suppression of systemic spread of human lung adenocarcinoma cells by monocyte chemoattractant protein-1 gene transfection in severe combined immunodeficient mice," Cancer Res. (2000) 60:7002-7007.
Lindahl, et al., "Pericyte loss and microaneurysm formation in PDGF-B-deficient mice," Science (1997) 277:242-245.
Gengrinovitch, et al., "Glypican-1 is a VEGF165 binding proteoglycan that acts as an extracellular chaperone for VEGF165," J. Biol. Chem. (1999) 274:10816-10822.
Li, et al., "Increased responsiveness of hypoxic endothelial cells to FGF2 is mediated by HIF-1alpha-dependent regulation of enzymes involved in synthesis of heparan sulfate FGF2-binding sites," J. Cell Sci. (2002) 115:1951-1959.
Neufeld, et al., "Vascular endothelial growth factor (VEGF) and its receptors," FASEB J. (1999) 13:9-22.
Park, et al., "The vascular endothelial growth factor (VEGF) isoforms: differential deposition into the subepithelial extracellular matrix and bioactivity of extracellular matrix-bound VEGF," Mol. Biol. Cell (1993) 4:1317-1326.
Pepper, et al., "Transforming growth factor-beta: vasculogenesis, angiogenesis, and vessel wall integrity," Cytokine Growth Factor Rev. (1997) 8:21-43.
Xu and Yu, "E-cadherin negatively regulates CD44-hyaluronan interaction and CD44-mediated tumor invasion and branching morphogenesis," J. Biol. Chem. (2003) 278:8661-8668.
Poltorak, et al., "VEGF145, a secreted vascular endothelial growth factor isoform that binds to extracellular matrix," J. Biol. Chem. (1997) 272-7151-7158.
Robinson and Stringer, "The splice variants of vascular endothelial growth factor (VEGF) and their receptors," J. Cell Sci. (2001) 114:853-865.
Ruhrberg, "Endogenous inhibitors of angiogenesis," J. Cell Sci. (2001) 114:3215-3216.
Saaristo, et al., "Mechanisms of angiogenesis and their use in the inhibition of tumor growth and metastasis," Oncogene (2000) 19:6122-6129.
Maeshima, et al., "Tumstatin, and endothelial cell-specific inhibitor of protein synthesis," Science (2002) 295:140-143.
O'Reilly, et al., "Angiostatin: a novel angiogenesis inhibitor that mediates the suppression of metastases by a Lewis lung carcinoma," Cell (1994) 79:315-328.
O'Reilly, et al., "Antiangiogenic activity of the cleaved conformation of the serpin antithrombin," Science (1999) 285:1926-1928.
Yi and Ruoslahti, "A fibronectin fragment inhibits tumor growth, angiogenesis, and metastasis," Proc. Natl. Acad. Sci. USA (2001) 98:620-624.
Vu, et al., "MMP-9/gelatinase-B is a key regulator of growth plate angiogenesis and apoptosis of hypertrophic chondrocytes," Cell (1998) 93:411-422.
Vajkoczy, et al., "Microtumor growth initiates angiogenic sprouting with angiogenic sprouting with simultaneous expression of VEGF, VEGF receptor-2, and angiopoietin-2," J. Clin. Investig. (2002) 109:777-785.
Bloemendal, et al., "New strategies in anti-vascular cancer therapy," Eur. J. Clin. Investig. (1999) 29:802-809.
Harfouche, et al., "Mechanisms which mediate the antiapoptotic effects of angiopoietin-1 on endothelial cells," Microvasc. Res. (2002) 64:135-147.
Hiraoka, et al., "Matrix metalloproteinases regulate neovascularization by acting as pericellular fibrinolysins," Cell (1998) 95:365-377.
Bergers, et al., "Matrix metalloproteinase-9 triggers the angiogenic switch during carcinogenesis," Nature Cell Biol. (2000) 2:737-744.
Fang, et al., "Matrix metalloproteinase-2 is required for the switch to the angiogenic phenotype in a tumor model," Proc. Natl. Acad. Sci. USA (2000) 97:3884-3889.
Pfeifer, et al., "Suppression of angiogenesis by lentiviral delivery of PEX, a noncatalytic fragment of matrix metalloproteinase 2," Proc. Natl. Acad. Sci. USA (2000) 97:12227-12232.
Sternlicht and Werb, "How matrix metalloproteinases regulate cell behavior," Ann. Rev. Cell Dev. Biol. (2001) 17:463-516.
Silletti, et al., "Disruption of matrix metalloproteinase 2 binding to integrin alphavbeta3 by an organic molecule inhibits angiogenesis and tumor growth in vivo," Proc. Natl. Acad. Sci. USA (2001) 98:119-124.

Sipes, et al., "Cooperation between thrombospondin-1 type 1 repeat peptides and alphavbeta3 integrin ligands to promote melanoma cell spreading and focal adhesion kinase phosphorylation," J. Biol. Chem. (1999) 274:22755-22762.

Visconti, et al., "Orchestration of angiogenesis and arteriovenous contribution by angiopoietins and vascular endothelial groth factor (VEGF)," Proc. Natl. Acad. Sci. USA (2002) 99:8219-8224.

Uemura, et al., "Recombinant angiopoietin-1 restores higher-order architecture of growing blood vessels in mice in the absence of mural cells," J. Clin. Invest. (2002) 110:1619-1628.

Yu and Stmenkovic, "Cell surface-localized matrix metalloproteinase-9 protelytically activates TGF-beta and promotes tumor invasion and angiogenesis," Genes Dev. (2000) 14:163-176.

McFall and Rapraeger, "Characterization of the high affinity cell-binding domain in the cell surface proteoglycan syndecan-4," J. Biol. Chem. (1998) 273:28270-28276.

Olson, et al., "High affinity binding of latent matrix metalloproteinase-9 to the alpha2(IV) chain of collagen IV," J. Biol. Chem. (1998) 273:10672-10681.

Brooks, et al., "Localization of matrix metalloproteinase MMP-2 to the surface of invasive sells by interaction with integrin alphavbeta3," Cell (1996) 85:683-693.

Moyon, et al., "Selective expression of angiopoietin 1and 2 in mesenchymal cells surrounding veins and arteries of the avian embryo," Mechs. Devel. (2001) 106:133-136.

Wong, et al., "Tie2 expression and phosphorylation in angiogenic and quiescent adult tissues," Circ. Res. (1997) 81:567-574.

Shim, et al., "Inhibition of angiopoietin-1 expression in tumor cells by an antisense RNA approach inhibited xenograft tumor growth in immunodeficient mice," Int. J. Cancer (2001) 94:6-15.

Shim, et al., "Angiopoietin 1 promotes tumor angiogenesis and tumor vessel plasticity of human cervical cancer in mice," Exp. Cell Res. (2002) 279:299-309.

Joussen, et al., "Suppression of diabetic retinopathy with angiopoietin-1," Am. J. Pathol. (2002) 160:1683-1693.

Hattori, et al., "Vascular endothelial growth factor and angiopoietin-1 stimulate postnatal hematopoiesis by recruitment of vasculogenic and hematopoietic stem cells," J. Exp. Med. (2001) 193:1005-1014.

Davis, et al., "Angiopoietins have distinct modular domains essential for receptor binding, dimerization and superclustering," Nature Struct. Biol. (2002) 10:38-44.

Kovesdi et al., Database GenCore, Accession No. AAE32344, Oct. 24, 2002, Gene Sequence.

International Search Report Dated Jan. 14, 2005 for International Application No. PCT/US04/06101.

* cited by examiner

Cell culture media

ECM materials

SEQUENCE LISTING

```
<160> NUMBER OF SEQ ID NOS: 36

<210> SEQ ID NO 1
<211> LENGTH: 20
<212> TYPE: PRT
<213> ORGANISM: Homo sapiens

<400> SEQUENCE: 1

Leu Cys Thr Lys Glu Gly Val Leu Leu Lys Gly Gly Lys Arg Glu Glu
1               5                   10                  15

Glu Lys Pro Phe
            20

<210> SEQ ID NO 2
<211> LENGTH: 20
<212> TYPE: PRT
<213> ORGANISM: mouse

<400> SEQUENCE: 2

Leu Cys Thr Lys Glu Gly Val Leu Leu Lys Gly Gly Lys Arg Glu Glu
1               5                   10                  15

Glu Lys Pro Phe
            20

<210> SEQ ID NO 3
<211> LENGTH: 42
<212> TYPE: PRT
<213> ORGANISM: Homo sapiens

<400> SEQUENCE: 3

Asn Gln Arg Arg Ser Pro Glu Asn Ser Gly Arg Arg Tyr Asn Arg Ile
1               5                   10                  15

Gln His Gly Gln Cys Ala Tyr Thr Phe Ile Leu Pro Glu His Asp Gly
            20                  25                  30

Asn Cys Arg Glu Ser Thr Thr Asp Gln Tyr
        35                  40

<210> SEQ ID NO 4
<211> LENGTH: 42
<212> TYPE: PRT
<213> ORGANISM: mouse
```

-continued

```
<400> SEQUENCE: 4

Asn Gln Arg Arg Asn Pro Glu Asn Gly Gly Arg Arg Tyr Asn Arg Ile
1               5                   10                  15

Gln His Gly Gln Cys Ala Tyr Thr Phe Ile Leu Pro Glu His Asp Gly
            20                  25                  30

Asn Cys Arg Glu Ser Ala Thr Glu Gln Tyr
        35                  40

<210> SEQ ID NO 5
<211> LENGTH: 471
<212> TYPE: PRT
<213> ORGANISM: Homo sapiens

<400> SEQUENCE: 5

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Arg Asp Cys Ala Asp Val Tyr Gln Ala Gly Phe Asn Lys Ser Gly
            260                 265                 270

Ile Tyr Thr Ile Tyr Ile Asn Asn Met Pro Glu Pro Lys Lys Val Phe
        275                 280                 285

Cys Asn Met Asp Val Asn Gly Gly Gly Trp Thr Val Ile Gln His Arg
    290                 295                 300

Glu Asp Gly Ser Leu Asp Phe Gln Arg Gly Trp Lys Glu Tyr Lys Met
305                 310                 315                 320
```

```
Gly Phe Gly Asn Pro Ser Gly Glu Tyr Trp Leu Gly Asn Glu Phe Ile
            325                 330                 335

Phe Ala Ile Thr Ser Gln Arg Gln Tyr Met Leu Arg Ile Glu Leu Met
            340                 345                 350

Asp Trp Glu Gly Asn Arg Ala Tyr Ser Gln Tyr Asp Arg Phe His Ile
            355                 360                 365

Gly Asn Glu Lys Gln Asn Tyr Arg Leu Tyr Leu Lys Gly His Thr Gly
            370                 375                 380

Thr Ala Gly Lys Gln Ser Ser Leu Ile Leu His Gly Ala Asp Phe Ser
385                 390                 395                 400

Thr Lys Asp Ala Asp Asn Asp Asn Cys Met Cys Lys Cys Ala Leu Met
            405                 410                 415

Leu Thr Gly Gly Trp Phe Asp Ala Cys Gly Pro Ser Asn Leu Asn Gly
            420                 425                 430

Met Phe Tyr Thr Ala Gly Gln Asn His Gly Lys Leu Asn Gly Ile Lys
            435                 440                 445

Trp His Tyr Phe Lys Gly Pro Ser Tyr Ser Leu Arg Ser Thr Thr Met
            450                 455                 460

Met Ile Arg Pro Leu Asp Phe
465                 470

<210> SEQ ID NO 6
<211> LENGTH: 472
<212> TYPE: PRT
<213> ORGANISM: mouse

<400> SEQUENCE: 6

Met Thr Val Phe Leu Ser Phe Ala Phe Phe Ala Ala Ile Leu Thr His
1               5                   10                  15

Ile Gly Cys Ser Asn Gln Arg Arg Asn Pro Glu Asn Gly Gly Arg Arg
            20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Ala Thr Glu Gln Tyr Asn Thr
50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
            85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
            130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
            165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Ser
210                 215                 220
```

-continued

```
Arg Gln Thr Phe Ile Ile Gln Glu Leu Glu Lys Gln Leu Ser Arg Ala
225                 230                 235                 240

Thr Asn Asn Ser Ile Leu Gln Lys Gln Gln Leu Glu Leu Met Asp
            245                 250                 255

Thr Arg Asp Cys Ala Asp Val Tyr Gln Ala Gly Phe Asn Lys Ser Gly
                260                 265                 270

Ile Tyr Thr Ile Tyr Phe Asn Asn Met Pro Glu Pro Lys Lys Val Phe
            275                 280                 285

Cys Asn Met Asp Val Asn Gly Gly Trp Thr Val Ile Gln His Arg
    290                 295                 300

Glu Asp Gly Ser Leu Asp Phe Gln Arg Gly Trp Lys Glu Tyr Lys Met
305                 310                 315                 320

Gly Phe Gly Asn Pro Ser Gly Glu Tyr Trp Leu Gly Asn Glu Phe Ile
                325                 330                 335

Phe Ala Ile Thr Ser Gln Arg Gln Tyr Met Leu Arg Ile Glu Leu Met
            340                 345                 350

Asp Trp Glu Gly Asn Arg Ala Tyr Ser Gln Tyr Asp Arg Phe His Ile
            355                 360                 365

Gly Asn Glu Lys Gln Asn Tyr Arg Leu Tyr Leu Lys Gly His Thr Gly
            370                 375                 380

Thr Ala Gly Lys Gln Ser Ser Leu Ile Leu His Gly Ala Asp Phe Ser
385                 390                 395                 400

Thr Lys Asp Ala Asp Asn Asp Asn Cys Met Cys Lys Cys Ala Leu Met
                405                 410                 415

Leu Thr Gly Gly Trp Trp Phe Asp Ala Cys Gly Pro Ser Asn Leu Asn
            420                 425                 430

Gly Met Phe Tyr Thr Ala Gly Gln Asn His Gly Lys Leu Asn Gly Ile
            435                 440                 445

Lys Trp His Tyr Phe Lys Gly Pro Ser Tyr Ser Leu Arg Ser Thr Thr
            450                 455                 460

Met Met Ile Arg Pro Leu Asp Phe
465                 470

<210> SEQ ID NO 7
<211> LENGTH: 456
<212> TYPE: PRT
<213> ORGANISM: Homo sapiens

<400> SEQUENCE: 7

Met Thr Val Phe Leu Ser Phe Ala Phe Leu Ala Ala Ile Leu Thr His
1               5                   10                  15

Ile Gly Cys Ser Asn Thr Asn Ala Leu Gln Arg Asp Ala Pro His Val
            20                  25                  30

Glu Pro Asp Phe Ser Ser Gln Lys Leu Gln His Leu Glu His Val Met
        35                  40                  45

Glu Asn Tyr Thr Gln Trp Leu Gln Lys Leu Glu Asn Tyr Ile Val Glu
    50                  55                  60

Asn Met Lys Ser Glu Met Ala Gln Ile Gln Gln Asn Ala Val Gln Asn
65                  70                  75                  80

His Thr Ala Thr Met Leu Glu Ile Gly Thr Ser Leu Leu Ser Gln Thr
                85                  90                  95

Ala Glu Gln Thr Arg Lys Leu Thr Asp Val Glu Thr Gln Val Leu Asn
            100                 105                 110

Gln Thr Ser Arg Leu Glu Ile Gln Leu Leu Glu Asn Ser Leu Ser Thr
```

```
                115                 120                 125
Tyr Lys Leu Glu Lys Gln Leu Leu Gln Gln Thr Asn Glu Ile Leu Lys
    130                 135                 140

Ile His Glu Lys Asn Ser Leu Leu Glu His Lys Ile Leu Glu Met Glu
145                 150                 155                 160

Gly Lys His Lys Glu Glu Leu Asp Thr Leu Lys Glu Lys Glu Asn
                165                 170                 175

Leu Gln Gly Leu Val Thr Arg Gln Thr Tyr Ile Ile Gln Glu Leu Glu
            180                 185                 190

Lys Gln Leu Asn Arg Ala Thr Thr Asn Asn Ser Val Leu Gln Lys Gln
        195                 200                 205

Gln Leu Glu Leu Met Asp Thr Val His Asn Leu Val Asn Leu Cys Thr
    210                 215                 220

Lys Glu Gly Val Leu Leu Lys Gly Gly Lys Arg Glu Glu Lys Pro
225                 230                 235                 240

Phe Arg Asp Cys Ala Asp Val Tyr Gln Ala Gly Phe Asn Lys Ser Gly
                245                 250                 255

Ile Tyr Thr Ile Tyr Ile Asn Asn Met Pro Glu Pro Lys Lys Val Phe
            260                 265                 270

Cys Asn Met Asp Val Asn Gly Gly Gly Trp Thr Val Ile Gln His Arg
        275                 280                 285

Glu Asp Gly Ser Leu Asp Phe Gln Arg Gly Trp Lys Glu Tyr Lys Met
    290                 295                 300

Gly Phe Gly Asn Pro Ser Gly Glu Tyr Trp Leu Gly Asn Glu Phe Ile
305                 310                 315                 320

Phe Ala Ile Thr Ser Gln Arg Gln Tyr Met Leu Arg Ile Glu Leu Met
                325                 330                 335

Asp Trp Glu Gly Asn Arg Ala Tyr Ser Gln Tyr Asp Arg Phe His Ile
            340                 345                 350

Gly Asn Glu Lys Gln Asn Tyr Arg Leu Tyr Leu Lys Gly His Thr Gly
        355                 360                 365

Thr Ala Gly Lys Gln Ser Ser Leu Ile Leu His Gly Ala Asp Phe Ser
    370                 375                 380

Thr Lys Asp Ala Asp Asn Asp Asn Cys Met Cys Lys Cys Ala Leu Met
385                 390                 395                 400

Leu Thr Gly Gly Trp Trp Phe Asp Ala Cys Gly Pro Ser Asn Leu Asn
                405                 410                 415

Gly Met Phe Tyr Thr Ala Gly Gln Asn His Gly Lys Leu Asn Gly Ile
            420                 425                 430

Lys Trp His Tyr Phe Lys Gly Pro Ser Tyr Ser Leu Arg Ser Thr Thr
        435                 440                 445

Met Met Ile Arg Pro Leu Asp Phe
    450                 455

<210> SEQ ID NO 8
<211> LENGTH: 456
<212> TYPE: PRT
<213> ORGANISM: mouse

<400> SEQUENCE: 8

Met Thr Val Phe Leu Ser Phe Ala Phe Phe Ala Ala Ile Leu Thr His
1               5                   10                  15

Ile Gly Cys Ser Asn Thr Asn Ala Leu Gln Arg Asp Ala Pro His Val
            20                  25                  30
```

-continued

Glu Pro Asp Phe Ser Ser Gln Lys Leu Gln His Leu Glu His Val Met
            35                  40                  45

Glu Asn Tyr Thr Gln Trp Leu Gln Lys Leu Glu Asn Tyr Ile Val Glu
 50                  55                  60

Asn Met Lys Ser Glu Met Ala Gln Ile Gln Gln Asn Ala Val Gln Asn
 65                  70                  75                  80

His Thr Ala Thr Met Leu Glu Ile Gly Thr Ser Leu Leu Ser Gln Thr
                85                  90                  95

Ala Glu Gln Thr Arg Lys Leu Thr Asp Val Glu Thr Gln Val Leu Asn
            100                 105                 110

Gln Thr Ser Arg Leu Glu Ile Gln Leu Leu Glu Asn Ser Leu Ser Thr
            115                 120                 125

Tyr Lys Leu Glu Lys Gln Leu Leu Gln Gln Thr Asn Glu Ile Leu Lys
            130                 135                 140

Ile His Glu Lys Asn Ser Leu Leu Glu His Lys Ile Leu Glu Met Glu
145                 150                 155                 160

Gly Lys His Lys Glu Glu Leu Asp Thr Leu Lys Glu Glu Lys Glu Asn
                165                 170                 175

Leu Gln Gly Leu Val Ser Arg Gln Thr Phe Ile Ile Gln Glu Leu Glu
            180                 185                 190

Lys Gln Leu Ser Arg Ala Thr Asn Asn Asn Ser Ile Leu Gln Lys Gln
            195                 200                 205

Gln Leu Glu Leu Met Asp Thr Val His Asn Leu Val Ser Leu Cys Thr
            210                 215                 220

Lys Glu Gly Val Leu Leu Lys Gly Gly Lys Arg Glu Glu Glu Lys Pro
225                 230                 235                 240

Phe Arg Asp Cys Ala Asp Val Tyr Gln Ala Gly Phe Asn Lys Ser Gly
                245                 250                 255

Ile Tyr Thr Ile Tyr Phe Asn Asn Met Pro Glu Pro Lys Lys Val Phe
                260                 265                 270

Cys Asn Met Asp Val Asn Gly Gly Gly Trp Thr Val Ile Gln His Arg
            275                 280                 285

Glu Asp Gly Ser Leu Asp Phe Gln Arg Gly Trp Lys Glu Tyr Lys Met
            290                 295                 300

Gly Phe Gly Asn Pro Ser Gly Glu Tyr Trp Leu Gly Asn Glu Phe Ile
305                 310                 315                 320

Phe Ala Ile Thr Ser Gln Arg Gln Tyr Met Leu Arg Ile Glu Leu Met
                325                 330                 335

Asp Trp Glu Gly Asn Arg Ala Tyr Ser Gln Tyr Asp Arg Phe His Ile
            340                 345                 350

Gly Asn Glu Lys Gln Asn Tyr Arg Leu Tyr Leu Lys Gly His Thr Gly
            355                 360                 365

Thr Ala Gly Lys Gln Ser Ser Leu Ile Leu His Gly Ala Asp Phe Ser
 370                 375                 380

Thr Lys Asp Ala Asp Asn Asp Asn Cys Met Cys Lys Cys Ala Leu Met
385                 390                 395                 400

Leu Thr Gly Gly Trp Trp Phe Asp Ala Cys Gly Pro Ser Asn Leu Asn
                405                 410                 415

Gly Met Phe Tyr Thr Ala Gly Gln Asn His Gly Lys Leu Asn Gly Ile
            420                 425                 430

Lys Trp His Tyr Phe Lys Gly Pro Ser Tyr Ser Leu Arg Ser Thr Thr
            435                 440                 445

Met Met Ile Arg Pro Leu Asp Phe 450 455

<210> SEQ ID NO 9
<211> LENGTH: 430
<212> TYPE: PRT
<213> ORGANISM: Homo sapiens

<400> SEQUENCE: 9

```
Met Thr Val Phe Leu Ser Phe Ala Phe Leu Ala Ala Ile Leu Thr His
1               5                   10                  15

Ile Gly Cys Ser Asn Thr Asn Ala Leu Gln Arg Asp Ala Pro His Val
            20                  25                  30

Glu Pro Asp Phe Ser Ser Gln Lys Leu Gln His Leu Glu His Val Met
        35                  40                  45

Glu Asn Tyr Thr Gln Trp Leu Gln Lys Leu Glu Asn Tyr Ile Val Glu
    50                  55                  60

Asn Met Lys Ser Glu Met Ala Gln Ile Gln Gln Asn Ala Val Gln Asn
65                  70                  75                  80

His Thr Ala Thr Met Leu Glu Ile Gly Thr Ser Leu Leu Ser Gln Thr
                85                  90                  95

Ala Glu Gln Thr Arg Lys Leu Thr Asp Val Glu Thr Gln Val Leu Asn
            100                 105                 110

Gln Thr Ser Arg Leu Glu Ile Gln Leu Leu Glu Asn Ser Leu Ser Thr
        115                 120                 125

Tyr Lys Leu Glu Lys Gln Leu Leu Gln Gln Thr Asn Glu Ile Leu Lys
    130                 135                 140

Ile His Glu Lys Asn Ser Leu Leu Glu His Lys Ile Leu Glu Met Glu
145                 150                 155                 160

Gly Lys His Lys Glu Glu Leu Asp Thr Leu Lys Glu Glu Lys Glu Asn
                165                 170                 175

Leu Gln Gly Leu Val Thr Arg Gln Thr Tyr Ile Ile Gln Glu Leu Glu
            180                 185                 190

Lys Gln Leu Asn Arg Ala Thr Thr Asn Asn Ser Val Leu Gln Lys Gln
        195                 200                 205

Gln Leu Glu Leu Met Asp Thr Arg Asp Cys Ala Asp Val Tyr Gln Ala
    210                 215                 220

Gly Phe Asn Lys Ser Gly Ile Tyr Thr Ile Tyr Ile Asn Asn Met Pro
225                 230                 235                 240

Glu Pro Lys Lys Val Phe Cys Asn Met Asp Val Asn Gly Gly Gly Trp
                245                 250                 255

Thr Val Ile Gln His Arg Glu Asp Gly Ser Leu Asp Phe Gln Arg Gly
            260                 265                 270

Trp Lys Glu Tyr Lys Met Gly Phe Gly Asn Pro Ser Gly Glu Tyr Trp
        275                 280                 285

Leu Gly Asn Glu Phe Ile Phe Ala Ile Thr Ser Gln Arg Gln Tyr Met
    290                 295                 300

Leu Arg Ile Glu Leu Met Asp Trp Glu Gly Asn Arg Ala Tyr Ser Gln
305                 310                 315                 320

Tyr Asp Arg Phe His Ile Gly Asn Glu Lys Gln Asn Tyr Arg Leu Tyr
                325                 330                 335

Leu Lys Gly His Thr Gly Thr Ala Gly Lys Gln Ser Ser Leu Ile Leu
            340                 345                 350

His Gly Ala Asp Phe Ser Thr Lys Asp Ala Asp Asn Asp Asn Cys Met
        355                 360                 365
```

```
Cys Lys Cys Ala Leu Met Leu Thr Gly Gly Trp Trp Phe Asp Ala Cys
        370                 375                 380

Gly Pro Ser Asn Leu Asn Gly Met Phe Tyr Thr Ala Gly Gln Asn His
385                 390                 395                 400

Gly Lys Leu Asn Gly Ile Lys Trp His Tyr Phe Lys Gly Pro Ser Tyr
                405                 410                 415

Ser Leu Arg Ser Thr Thr Met Met Ile Arg Pro Leu Asp Phe
        420                 425                 430

<210> SEQ ID NO 10
<211> LENGTH: 430
<212> TYPE: PRT
<213> ORGANISM: mouse

<400> SEQUENCE: 10

Met Thr Val Phe Leu Ser Phe Ala Phe Phe Ala Ala Ile Leu Thr His
1               5                   10                  15

Ile Gly Cys Ser Asn Thr Asn Ala Leu Gln Arg Asp Ala Pro His Val
                20                  25                  30

Glu Pro Asp Phe Ser Ser Gln Lys Leu Gln His Leu Glu His Val Met
            35                  40                  45

Glu Asn Tyr Thr Gln Trp Leu Gln Lys Leu Glu Asn Tyr Ile Val Glu
    50                  55                  60

Asn Met Lys Ser Glu Met Ala Gln Ile Gln Gln Asn Ala Val Gln Asn
65                  70                  75                  80

His Thr Ala Thr Met Leu Glu Ile Gly Thr Ser Leu Leu Ser Gln Thr
                85                  90                  95

Ala Glu Gln Thr Arg Lys Leu Thr Asp Val Glu Thr Gln Val Leu Asn
            100                 105                 110

Gln Thr Ser Arg Leu Glu Ile Gln Leu Leu Glu Asn Ser Leu Ser Thr
        115                 120                 125

Tyr Lys Leu Glu Lys Gln Leu Leu Gln Gln Thr Asn Glu Ile Leu Lys
    130                 135                 140

Ile His Glu Lys Asn Ser Leu Leu Glu His Lys Ile Leu Glu Met Glu
145                 150                 155                 160

Gly Lys His Lys Glu Glu Leu Asp Thr Leu Lys Glu Glu Lys Glu Asn
                165                 170                 175

Leu Gln Gly Leu Val Ser Arg Gln Thr Phe Ile Ile Gln Glu Leu Glu
            180                 185                 190

Lys Gln Leu Ser Arg Ala Thr Asn Asn Asn Ser Ile Leu Gln Lys Gln
        195                 200                 205

Gln Leu Glu Leu Met Asp Thr Arg Asp Cys Ala Asp Val Tyr Gln Ala
    210                 215                 220

Gly Phe Asn Lys Ser Gly Ile Tyr Thr Ile Tyr Phe Asn Asn Met Pro
225                 230                 235                 240

Glu Pro Lys Lys Val Phe Cys Asn Met Asp Val Asn Gly Gly Gly Trp
                245                 250                 255

Thr Val Ile Gln His Arg Glu Asp Gly Ser Leu Asp Phe Gln Arg Gly
            260                 265                 270

Trp Lys Glu Tyr Lys Met Gly Phe Gly Asn Pro Ser Gly Glu Tyr Trp
        275                 280                 285

Leu Gly Asn Glu Phe Ile Phe Ala Ile Thr Ser Gln Arg Gln Tyr Met
    290                 295                 300

Leu Arg Ile Glu Leu Met Asp Trp Glu Gly Asn Arg Ala Tyr Ser Gln
305                 310                 315                 320
```

```
Tyr Asp Arg Phe His Ile Gly Asn Glu Lys Gln Asn Tyr Arg Leu Tyr
                325                 330                 335

Leu Lys Gly His Thr Gly Thr Ala Gly Lys Gln Ser Ser Leu Ile Leu
            340                 345                 350

His Gly Ala Asp Phe Ser Thr Lys Asp Ala Asp Asn Asp Asn Cys Met
        355                 360                 365

Cys Lys Cys Ala Leu Met Leu Thr Gly Gly Trp Trp Phe Asp Ala Cys
    370                 375                 380

Gly Pro Ser Asn Leu Asn Gly Met Phe Tyr Thr Ala Gly Gln Asn His
385                 390                 395                 400

Gly Lys Leu Asn Gly Ile Lys Trp His Tyr Phe Lys Gly Pro Ser Tyr
                405                 410                 415

Ser Leu Arg Ser Thr Thr Met Met Ile Arg Pro Leu Asp Phe
            420                 425                 430

<210> SEQ ID NO 11
<211> LENGTH: 235
<212> TYPE: PRT
<213> ORGANISM: Homo sapiens

<400> SEQUENCE: 11

Met Thr Val Phe Leu Ser Phe Ala Phe Leu Ala Ala Ile Leu Thr His
1               5                   10                  15

Ile Gly Cys Ser Arg Asp Cys Ala Asp Val Tyr Gln Ala Gly Phe Asn
            20                  25                  30

Lys Ser Gly Ile Tyr Thr Ile Tyr Ile Asn Asn Met Pro Glu Pro Lys
        35                  40                  45

Lys Val Phe Cys Asn Met Asp Val Asn Gly Gly Gly Trp Thr Val Ile
    50                  55                  60

Gln His Arg Glu Asp Gly Ser Leu Asp Phe Gln Arg Gly Trp Lys Glu
65                  70                  75                  80

Tyr Lys Met Gly Phe Gly Asn Pro Ser Gly Glu Tyr Trp Leu Gly Asn
                85                  90                  95

Glu Phe Ile Phe Ala Ile Thr Ser Gln Arg Gln Tyr Met Leu Arg Ile
            100                 105                 110

Glu Leu Met Asp Trp Glu Gly Asn Arg Ala Tyr Ser Gln Tyr Asp Arg
        115                 120                 125

Phe His Ile Gly Asn Glu Lys Gln Asn Tyr Arg Leu Tyr Leu Lys Gly
    130                 135                 140

His Thr Gly Thr Ala Gly Lys Gln Ser Ser Leu Ile Leu His Gly Ala
145                 150                 155                 160

Asp Phe Ser Thr Lys Asp Ala Asp Asn Asp Asn Cys Met Cys Lys Cys
                165                 170                 175

Ala Leu Met Leu Thr Gly Gly Trp Trp Phe Asp Ala Cys Gly Pro Ser
            180                 185                 190

Asn Leu Asn Gly Met Phe Tyr Thr Ala Gly Gln Asn His Gly Lys Leu
        195                 200                 205

Asn Gly Ile Lys Trp His Tyr Phe Lys Gly Pro Ser Tyr Ser Leu Arg
    210                 215                 220

Ser Thr Thr Met Met Ile Arg Pro Leu Asp Phe
225                 230                 235

<210> SEQ ID NO 12
<211> LENGTH: 235
<212> TYPE: PRT
```

<213> ORGANISM: mouse

<400> SEQUENCE: 12

Met Thr Val Phe Leu Ser Phe Ala Phe Phe Ala Ala Ile Leu Thr His
1               5                   10                  15

Ile Gly Cys Ser Arg Asp Cys Ala Asp Val Tyr Gln Ala Gly Phe Asn
            20                  25                  30

Lys Ser Gly Ile Tyr Thr Ile Tyr Phe Asn Asn Met Pro Glu Pro Lys
        35                  40                  45

Lys Val Phe Cys Asn Met Asp Val Asn Gly Gly Gly Trp Thr Val Ile
50                  55                  60

Gln His Arg Glu Asp Gly Ser Leu Asp Phe Gln Arg Gly Trp Lys Glu
65                  70                  75                  80

Tyr Lys Met Gly Phe Gly Asn Pro Ser Gly Glu Tyr Trp Leu Gly Asn
                85                  90                  95

Glu Phe Ile Phe Ala Ile Thr Ser Gln Arg Gln Tyr Met Leu Arg Ile
            100                 105                 110

Glu Leu Met Asp Trp Glu Gly Asn Arg Ala Tyr Ser Gln Tyr Asp Arg
        115                 120                 125

Phe His Ile Gly Asn Glu Lys Gln Asn Tyr Arg Leu Tyr Leu Lys Gly
130                 135                 140

His Thr Gly Thr Ala Gly Lys Gln Ser Ser Leu Ile Leu His Gly Ala
145                 150                 155                 160

Asp Phe Ser Thr Lys Asp Ala Asp Asn Asp Asn Cys Met Cys Lys Cys
                165                 170                 175

Ala Leu Met Leu Thr Gly Gly Trp Trp Phe Asp Ala Cys Gly Pro Ser
            180                 185                 190

Asn Leu Asn Gly Met Phe Tyr Thr Ala Gly Gln Asn His Gly Lys Leu
        195                 200                 205

Asn Gly Ile Lys Trp His Tyr Phe Lys Gly Pro Ser Tyr Ser Leu Arg
210                 215                 220

Ser Thr Thr Met Met Ile Arg Pro Leu Asp Phe
225                 230                 235

<210> SEQ ID NO 13
<211> LENGTH: 498
<212> TYPE: PRT
<213> ORGANISM: Homo sapiens

<400> SEQUENCE: 13

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu

-continued

```
            115                 120                 125
Glu Ile Gly Thr Ser Leu Leu Ser Gln Thr Ala Glu Gln Thr Arg Lys
            130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
            165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
            290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 14
<211> LENGTH: 498
<212> TYPE: PRT
<213> ORGANISM: mouse
```

<400> SEQUENCE: 14

```
Met Thr Val Phe Leu Ser Phe Ala Phe Ala Ala Ile Leu Thr His
1               5                   10                  15

Ile Gly Cys Ser Asn Gln Arg Arg Asn Pro Glu Asn Gly Gly Arg Arg
                20                  25                  30

Tyr Asn Arg Ile Gln His Gly Gln Cys Ala Tyr Thr Phe Ile Leu Pro
                35                  40                  45

Glu His Asp Gly Asn Cys Arg Glu Ser Ala Thr Glu Gln Tyr Asn Thr
            50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
                115                 120                 125

Glu Ile Gly Thr Ser Leu Leu Ser Gln Thr Ala Glu Gln Thr Arg Lys
            130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
                180                 185                 190

Leu Leu Glu His Lys Ile Leu Glu Met Glu Gly Lys His Lys Glu Glu
                195                 200                 205

Leu Asp Thr Leu Lys Glu Glu Lys Glu Asn Leu Gln Gly Leu Val Ser
            210                 215                 220

Arg Gln Thr Phe Ile Ile Gln Glu Leu Glu Lys Gln Leu Ser Arg Ala
225                 230                 235                 240

Thr Asn Asn Asn Ser Ile Leu Gln Lys Gln Gln Leu Glu Leu Met Asp
                245                 250                 255

Thr Val His Asn Leu Val Ser Leu Cys Thr Lys Glu Gly Val Leu Leu
                260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Phe
            290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
                340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
        370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415
```

```
Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 15
<211> LENGTH: 496
<212> TYPE: PRT
<213> ORGANISM: Homo sapiens

<400> SEQUENCE: 15

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285
```

```
Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 16
<211> LENGTH: 496
<212> TYPE: PRT
<213> ORGANISM: mouse

<400> SEQUENCE: 16

Met Trp Gln Ile Ile Phe Leu Thr Phe Gly Trp Asp Leu Val Leu Ala
1               5                   10                  15

Ser Ala Tyr Ser Asn Phe Arg Lys Ser Val Asp Ser Thr Gly Arg Arg
            20                  25                  30

Gln Tyr Gln Val Gln Asn Gly Pro Cys Ser Tyr Thr Phe Leu Leu Pro
        35                  40                  45

Glu Thr Asp Ser Cys Arg Ser Ser Ser Pro Tyr Met Ser Asn Ala
    50                  55                  60

Val Gln Arg Asp Ala Pro Leu Asp Tyr Asp Ser Val Gln Arg Leu
65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Val Val Gln Asn Gln Thr Ala Val Met Ile Glu Ile Gly
        115                 120                 125

Thr Ser Leu Leu Asn Gln Thr Ala Ala Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
```

```
                165                 170                 175
Gln Thr Ser Glu Ile Asn Lys Leu Gln Asn Lys Asn Ser Phe Leu Glu
            180                 185                 190

Gln Lys Val Leu Asp Met Glu Gly Lys His Ser Glu Gln Leu Gln Ser
        195                 200                 205

Met Lys Glu Gln Lys Asp Glu Leu Gln Val Leu Val Ser Lys Gln Ser
    210                 215                 220

Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Glu Thr Val Asn
            245                 250                 255

Ser Leu Leu Thr Met Met Ser Ser Pro Asn Ser Lys Ser Ser Val Ala
        260                 265                 270

Ile Arg Lys Glu Glu Gln Thr Thr Phe Arg Asp Cys Ala Glu Ile Phe
    275                 280                 285

Lys Ser Gly Leu Thr Thr Ser Gly Ile Tyr Thr Leu Thr Phe Pro Asn
290                 295                 300

Ser Thr Glu Glu Ile Lys Ala Tyr Cys Asp Met Asp Val Gly Gly Gly
305                 310                 315                 320

Gly Trp Thr Val Ile Gln His Arg Glu Asp Gly Ser Val Asp Phe Gln
            325                 330                 335

Arg Thr Trp Lys Glu Tyr Lys Glu Gly Phe Gly Asn Pro Leu Gly Glu
        340                 345                 350

Tyr Trp Leu Gly Asn Glu Phe Val Ser Gln Leu Thr Gly Gln His Arg
    355                 360                 365

Tyr Val Leu Lys Ile Gln Leu Lys Asp Trp Glu Gly Asn Glu Ala His
    370                 375                 380

Ser Leu Tyr Asp His Phe Tyr Leu Ala Gly Glu Glu Ser Asn Tyr Arg
385                 390                 395                 400

Ile His Leu Thr Gly Leu Thr Gly Thr Ala Ala Lys Ile Ser Ser Ile
            405                 410                 415

Ser Gln Pro Gly Ser Asp Phe Ser Thr Lys Asp Ser Asp Asn Asp Lys
        420                 425                 430

Cys Ile Cys Lys Cys Ser Gln Met Leu Ser Gly Gly Trp Trp Phe Asp
    435                 440                 445

Ala Cys Gly Pro Ser Asn Leu Asn Gly Gln Tyr Tyr Pro Gln Lys Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
            485                 490                 495

<210> SEQ ID NO 17
<211> LENGTH: 503
<212> TYPE: PRT
<213> ORGANISM: Homo sapiens

<400> SEQUENCE: 17

Met Leu Ser Gln Leu Ala Met Leu Gln Gly Ser Leu Leu Leu Val Val
1               5                   10                  15

Ala Thr Met Ser Val Ala Gln Gln Thr Arg Gln Glu Ala Asp Arg Gly
            20                  25                  30

Cys Glu Thr Leu Val Val Gln His Gly His Cys Ser Tyr Thr Phe Leu
        35                  40                  45
```

-continued

```
Leu Pro Lys Ser Glu Pro Cys Pro Gly Pro Glu Val Ser Arg Asp
 50                  55                  60

Ser Asn Thr Leu Gln Arg Glu Ser Leu Ala Asn Pro Leu His Leu Gly
 65                  70                  75                  80

Lys Leu Pro Thr Gln Gln Val Lys Gln Leu Glu Gln Ala Leu Gln Asn
                 85                  90                  95

Asn Thr Gln Trp Leu Lys Lys Leu Glu Arg Ala Ile Lys Thr Ile Leu
                100                 105                 110

Arg Ser Lys Leu Glu Gln Val Gln Gln Gln Met Ala Gln Asn Gln Thr
                115                 120                 125

Ala Pro Met Leu Glu Leu Gly Thr Ser Leu Leu Asn Gln Thr Thr Ala
            130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
                180                 185                 190

Gly Gln Asn Ser Ala Leu Glu Lys Arg Leu Gln Ala Leu Glu Thr Lys
                195                 200                 205

Gln Gln Glu Glu Leu Ala Ser Ile Leu Ser Lys Ala Lys Leu Leu
210                 215                 220

Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln Gln His
                245                 250                 255

Ser Leu Arg Gln Leu Leu Val Leu Leu Arg His Leu Val Gln Glu Arg
                260                 265                 270

Ala Asn Ala Ser Ala Pro Ala Phe Ile Met Ala Gly Glu Gln Val Phe
            275                 280                 285

Gln Asp Cys Ala Glu Ile Gln Arg Ser Gly Ala Ser Ala Ser Gly Val
290                 295                 300

Tyr Thr Ile Gln Val Ser Asn Ala Thr Lys Pro Arg Lys Val Phe Cys
305                 310                 315                 320

Asp Leu Gln Ser Ser Gly Gly Arg Trp Thr Leu Ile Gln Arg Arg Glu
                325                 330                 335

Asn Gly Thr Val Asn Phe Gln Arg Asn Trp Lys Asp Tyr Lys Gln Gly
                340                 345                 350

Phe Gly Asp Pro Ala Gly Glu His Trp Leu Gly Asn Glu Val Val His
            355                 360                 365

Gln Leu Thr Arg Arg Ala Ala Tyr Ser Leu Arg Val Glu Leu Gln Asp
            370                 375                 380

Trp Glu Gly His Glu Ala Tyr Ala Gln Tyr Glu His Phe His Leu Gly
385                 390                 395                 400

Ser Glu Asn Gln Leu Tyr Arg Leu Ser Val Val Gly Tyr Ser Gly Ser
                405                 410                 415

Ala Gly Arg Gln Ser Ser Leu Val Leu Gln Asn Thr Ser Phe Ser Thr
            420                 425                 430

Leu Asp Ser Asp Asn Asp His Cys Leu Cys Lys Cys Ala Gln Val Met
            435                 440                 445

Ser Gly Gly Trp Trp Phe Asp Ala Cys Gly Leu Ser Asn Leu Asn Gly
            450                 455                 460

Val Tyr Tyr His Ala Pro Asp Asn Lys Tyr Lys Met Asp Gly Ile Arg
```

```
                465                 470                 475                 480
Trp His Tyr Phe Lys Gly Pro Ser Tyr Ser Leu Arg Ala Ser Arg Met
                    485                 490                 495

Met Ile Arg Pro Leu Asp Ile
            500

<210> SEQ ID NO 18
<211> LENGTH: 509
<212> TYPE: PRT
<213> ORGANISM: mouse

<400> SEQUENCE: 18

Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly His Arg
            20                  25                  30

Gln Ile His Gln Val Arg Arg Gly Gln Cys Ser Tyr Thr Phe Val Val
        35                  40                  45

Pro Glu Pro Asp Ile Cys Gln Leu Ala Pro Thr Ala Ala Pro Glu Ala
    50                  55                  60

Leu Gly Gly Ser Asn Ser Leu Gln Arg Asp Leu Pro Ala Ser Arg Leu
65                  70                  75                  80

His Leu Thr Asp Trp Arg Ala Gly Arg Ala Gln Arg Ala Gln Arg Val
                85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
        115                 120                 125

Gln Gln Asp Thr Ile Gln Asn Gln Thr Thr Met Leu Ala Leu Gly
    130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190

Gln Ser Arg Glu Leu Gln Arg Leu Gln Gly Arg Asn Arg Ala Leu Glu
        195                 200                 205

Thr Arg Leu Gln Ala Leu Glu Ala Gln His Gln Ala Gln Leu Asn Ser
    210                 215                 220

Leu Gln Glu Lys Arg Glu Gln Leu His Ser Leu Leu Gly His Gln Thr
225                 230                 235                 240

Gly Thr Leu Ala Asn Leu Lys His Asn Leu His Ala Leu Ser Ser Asn
                245                 250                 255

Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
    290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Gly Trp Thr
                325                 330                 335
```

```
Leu Ile Gln His Arg Glu Asp Gly Ser Val Asn Phe Gln Arg Thr Trp
            340                 345                 350
Glu Glu Tyr Lys Glu Gly Phe Gly Asn Val Ala Arg Glu His Trp Leu
        355                 360                 365
Gly Asn Glu Ala Val His Arg Leu Thr Ser Arg Thr Ala Tyr Leu Leu
    370                 375                 380
Arg Val Glu Leu His Asp Trp Glu Gly Arg Gln Thr Ser Ile Gln Tyr
385                 390                 395                 400
Glu Asn Phe Gln Leu Gly Ser Glu Arg Gln Arg Tyr Ser Leu Ser Val
                405                 410                 415
Asn Asp Ser Ser Ser Ala Gly Arg Lys Asn Ser Leu Ala Pro Gln
            420                 425                 430
Gly Thr Lys Phe Ser Thr Lys Asp Met Asp Asn Asp Asn Cys Met Cys
        435                 440                 445
Lys Cys Ala Gln Met Leu Ser Gly Gly Trp Trp Phe Asp Ala Cys Gly
    450                 455                 460
Leu Ser Asn Leu Asn Gly Ile Tyr Tyr Ser Val His Gln His Leu His
465                 470                 475                 480
Lys Ile Asn Gly Ile Arg Trp His Tyr Phe Arg Gly Pro Ser Tyr Ser
                485                 490                 495
Leu His Gly Thr Arg Met Met Leu Arg Pro Met Gly Ala
            500                 505

<210> SEQ ID NO 19
<211> LENGTH: 60
<212> TYPE: DNA
<213> ORGANISM: Homo sapiens

<400> SEQUENCE: 19
ctttgcacta agaaggtgt tttactaaag ggaggaaaaa gagaggaaga gaaaccattt    60

<210> SEQ ID NO 20
<211> LENGTH: 60
<212> TYPE: DNA
<213> ORGANISM: mouse

<400> SEQUENCE: 20
ctttgcacta agaaggtgt tttgctaaag ggaggaaaaa gagaagaaga gaaaccattt    60

<210> SEQ ID NO 21
<211> LENGTH: 126
<212> TYPE: DNA
<213> ORGANISM: Homo sapiens

<400> SEQUENCE: 21
aatcagcgcc gaagtccaga aaacagtggg agaagatata accggattca acatgggcaa    60
tgtgcctaca ctttcattct tccagaacac gatggcaact gtcgtgagag tacgacagac   120
cagtac                                                              126

<210> SEQ ID NO 22
<211> LENGTH: 126
<212> TYPE: DNA
<213> ORGANISM: mouse

<400> SEQUENCE: 22
aaccagcgcc gaaatccaga aaacggaggg agaagatata accggattca acatgggcaa    60
tgtgcctaca ctttcattct tccagaacac gacgggaact gccgtgagag tgcgacagag   120
```

<210> SEQ ID NO 23
<211> LENGTH: 1419
<212> TYPE: DNA
<213> ORGANISM: Homo sapiens

<400> SEQUENCE: 23

```
cagtac                                                               126 atgacagttt tcctttcctt tgctttcctc gctgccattc tgactcacat agggtgcagc     60
aatcagcgcc gaagtccaga aaacagtggg agaagatata accggattca acatgggcaa   120
tgtgcctaca ctttcattct tccagaacac gatggcaact gtcgtgagag tacgacagac   180
cagtacaaca caaacgctct gcagagagat gctccacacg tggaaccgga tttctcttcc   240
cagaaacttc aacatctgga acatgtgatg gaaaattata ctcagtggct gcaaaaactt   300
gagaattaca ttgtggaaaa catgaagtcg gagatggccc agatacagca gaatgcagtt   360
cagaaccaca cggctaccat gctggagata ggaaccagcc tcctctctca gactgcagag   420
cagaccagaa agctgacaga tgttgagacc caggtactaa atcaaacttc tcgacttgag   480
atacagctgc tggagaattc attatccacc tacaagctag agaagcaact tcttcaacag   540
acaaatgaaa tcttgaagat ccatgaaaaa acagtttat tagaacataa atcttagaa       600
atggaaggaa acacaagga agagttggac accttaaagg aagagaaaga gaaccttcaa     660
ggcttggtta ctcgtcaaac atatataatc caggagctgg aaaagcaatt aaacagagct   720
accaccaaca cagtgtcct tcagaagcag caactggagc tgatggacac aagagactgt     780
gcagatgtat atcaagctgg ttttaataaa agtggaatct cactatttta tattaataat   840
atgccagaac ccaaaaaggt gttttgcaat atggatgtca atggggagg ttggactgta      900
atacaacatc gtgaagatgg aagtctagat ttccaaagag gctggaagga atataaaatg   960
ggttttggaa atccctccgg tgaatattgg ctgggaatg agtttatttt tgccattacc     1020
agtcagaggc agtacatgct aagaattgag ttaatggact gggaagggaa ccgagcctat   1080
tcacagtatg acagattcca cataggaaat gaaaagcaaa actataggtt gtatttaaaa   1140
ggtcacactg gacagcagg aaaacagagc agcctgatct tacacggtgc tgatttcagc   1200
actaaagatg ctgataatga caactgtatg tgcaaatgtg ccctcatgtt aacaggagga   1260
tggtggtttg atgcttgtgg cccctccaat ctaaatgaa tgttctatac tgcgggacaa   1320
aaccatggaa aactgaatgg gataaagtgg cactacttca aagggcccag ttactcctta   1380
cgttccacaa ctatgatgat tcgaccttta gattttga                           1419
```

<210> SEQ ID NO 24
<211> LENGTH: 1419
<212> TYPE: DNA
<213> ORGANISM: mouse

<400> SEQUENCE: 24

```
atgacagttt tcctttcctt tgcattcttc gctgccattc tgactcacat agggtgcagc     60
aaccagcgcc gaaatccaga aaacggaggg agaagatata accggattca acatgggcaa   120
tgtgcctaca ctttcattct tccagaacac gacgggaact gccgtgagag tgcgacagag   180
cagtacaaca ccaacgctct gcaagggat gctccacacg tggagccgga tttctcttcc      240
cagaaacttc agcatctgga gcatgtgatg gaaaattata ctcagtggct gcaaaaactt   300
gagaattaca ttgtggaaaa tatgaagtcg gagatggccc agatacaaca gaatgctgtt   360
caaaaccaca cggccaccat gcttgagata ggaaccagtc tcttatctca gactgcagag   420
```

| | | |
|---|---|---|
| cagacccgaa agctgacaga tgttgagacc caggtactaa atcaaacatc ccgacttgaa | 480 | |
| atacaactgc tagagaattc attatcaaca tacaagctag agaagcaact tctccaacag | 540 | |
| acaaatgaaa ttctgaagat tcacgaaaaa acagtttac tagagcacaa aatcttagaa | 600 | |
| atggagggaa acacaaaga agaattggac accttgaagg aggagaaaga aaaccttcaa | 660 | |
| ggcttggttt ctcgtcagac attcatcatc caggagttgg agaagcaact tagtagagct | 720 | |
| accaacaaca acagcatcct gcagaagcaa caactggagc tcatggacac acgagactgt | 780 | |
| gcagatgtat atcaagctgg ttttaataaa agtggaatct acactattta ttttaataat | 840 | |
| atgccagaac ccaaaaaggt attttgcaat atggatgtga atgggggagg ttggacagta | 900 | |
| atacaacacc gggaagatgg aagcctggat ttccagaggg gctggaagga gtataaaatg | 960 | |
| ggttttggga atccctctgg tgaatattgg ctcgggaacg agttcatttt tgcaataacc | 1020 | |
| agtcagaggc agtacatgct gaggattgag ctgatggact gggaagggaa ccgagcctac | 1080 | |
| tcacagtacg acagattcca cataggaaat gaaaagcaga actataggtt atatttaaaa | 1140 | |
| ggtcacacag gacagcagg caaacagagc agcttgatct tacacggtgc tgatttcagc | 1200 | |
| acgaaggatg ctgataacga caactgtatg tgcaaatgcg ctctcatgct aacaggaggt | 1260 | |
| tggtggttcg atgcctgtgg cccttccaat ctaaatggaa tgttctacac tgcgggacaa | 1320 | |
| aatcatggaa aactgaatgg gataaagtgg cactacttca aagggcccag ttactcctta | 1380 | |
| cgttccacca ccatgatgat ccggcccttg gacttttga | 1419 | |

<210> SEQ ID NO 25
<211> LENGTH: 1371
<212> TYPE: DNA
<213> ORGANISM: homo sapiens

<400> SEQUENCE: 25

| | | |
|---|---|---|
| atgacagttt tcctttcctt tgctttcctc gctgccattc tgactcacat agggtgcagc | 60 | |
| aacacaaacg ctctgcagag agatgctcca cacgtggaac cggatttctc ttcccagaaa | 120 | |
| cttcaacatc tggaacatgt gatggaaaat tatactcagt ggctgcaaaa acttgagaat | 180 | |
| tacattgtgg aaaacatgaa gtcggagatg cccagatac agcagaatgc agttcagaac | 240 | |
| cacacggcta ccatgctgga gataggaacc agcctcctct ctcagactgc agagcagacc | 300 | |
| agaaagctga cagatgttga gacccaggta ctaaatcaaa cttctcgact tgagatacag | 360 | |
| ctgctggaga attcattatc cacctacaag ctagagaaga acttcttca acagacaaat | 420 | |
| gaaatcttga agatccatga aaaaacagt ttattagaac ataaaatctt agaaatggaa | 480 | |
| ggaaaacaca aggaagagtt ggacacctta aggaagaga aagagaacct tcaaggcttg | 540 | |
| gttactcgtc aaacatatat aatccaggag ctggaaaagc aattaaacag agctaccacc | 600 | |
| aacaacagtg tccttcagaa gcagcaactg gagctgatgg acacagtcca caaccttgtc | 660 | |
| aatctttgca ctaaagaagg tgttttacta aagggaggaa aagagagga agagaaacca | 720 | |
| tttagagact gtgcagatgt atatcaagct ggttttaata aaagtggaat ctacactatt | 780 | |
| tatattaata atatgccaga acccaaaaag gtgttttgca atatggatgt caatggggga | 840 | |
| ggttggactg taatacaaca tcgtgaagat ggaagtctag atttccaaag aggctggaag | 900 | |
| gaatataaaa tgggttttgg aaatccctcc ggtgaatatt ggctgggaa tgagtttatt | 960 | |
| tttgccatta ccagtcagag gcagtacatg ctaagaattg agttaatgga ctggaaggg | 1020 | |
| aaccgagcct attcacagta tgacagattc cacataggaa atgaaaagca aaactatagg | 1080 | |

```
ttgtatttaa aaggtcacac tgggacagca ggaaaacaga gcagcctgat cttacacggt    1140
gctgatttca gcactaaaga tgctgataat gacaactgta tgtgcaaatg tgccctcatg    1200
ttaacaggag gatggtggtt tgatgcttgt ggcccctcca atctaaatgg aatgttctat    1260
actgcgggac aaaaccatgg aaaactgaat gggataaagt ggcactactt caaagggccc    1320
agttactcct tacgttccac aactatgatg attcgacctt tagatttttg a             1371
```

<210> SEQ ID NO 26
<211> LENGTH: 1371
<212> TYPE: DNA
<213> ORGANISM: mouse

<400> SEQUENCE: 26

```
atgacagttt tcctttcctt tgcattcttc gctgccattc tgactcacat agggtgcagc      60
aacaccaacg ctctgcaaag ggatgctcca cacgtggagc cggatttctc ttcccagaaa    120
cttcagcatc tggagcatgt gatggaaaat tatactcagt ggctgcaaaa acttgagaat    180
tacattgtgg aaaatatgaa gtcggagatg cccagatac aacagaatgc tgttcaaaac    240
cacacggcca ccatgcttga gataggaacc agtctcttat ctcagactgc agagcagacc    300
cgaaagctga cagatgttga cccaggta ctaaatcaaa catcccgact tgaaatacaa      360
ctgctagaga attcattatc aacatacaag ctagagaaga aacttctcca acagacaaat    420
gaaattctga gattcacga aaaaaacagt ttactagagc acaaaatctt agaaatggag    480
ggaaaacaca agaagaatt ggacaccttg aaggaggaga agaaaaacct tcaaggcttg    540
gtttctcgtc agacattcat catccaggag ttggagaagc aacttagtag agctaccaac    600
aacaacagca tcctgcagaa gcaacaactg gagctcatgg acacagttca taaccttgtc    660
agcctttgca ctaaagaagg tgttttgcta aagggaggaa aagagaaga agagaaacca    720 tttcgagact gtgcagatgt atatcaagct ggttttaata aaagtggaat ctacactatt    780
tattttaata atatgccaga acccaaaaag gtattttgca atatggatgt gaatggggga    840
ggttggacag taatacaaca ccgggaagat ggaagcctgg atttccagag gggctggaag    900
gagtataaaa tgggttttgg gaatccctct ggtgaatatt ggctcgggaa cgagttcatt    960
tttgcaataa ccagtcagag gcagtacatg ctgaggattg agctgatgga ctgggaaggg    1020
aaccgagcct actcacagta cgacagattc cacataggaa atgaaaagca gaactatagg    1080
ttatatttaa aggtcacac agggacagca ggcaaacaga gcagcttgat cttacacggt    1140
gctgatttca gcacgaagga tgctgataac gacaactgta tgtgcaaatg cgctctcatg    1200
ctaacaggag gttggtggtt cgatgcctgt ggcccttcca atctaaatgg aatgttctac    1260
actgcgggac aaaatcatgg aaaactgaat gggataaagt ggcactactt caaagggccc    1320
agttactcct tacgttccac caccatgatg atccggccct ggacttttg a               1371
```

<210> SEQ ID NO 27
<211> LENGTH: 1293
<212> TYPE: DNA
<213> ORGANISM: Homo sapiens

<400> SEQUENCE: 27

```
atgacagttt tcctttcctt tgctttcctc gctgccattc tgactcacat agggtgcagc      60
aacacaaacg ctctgcagag agatgctcca cacgtggaac cggatttctc ttcccagaaa    120
cttcaacatc tggaacatgt gatggaaaat tatactcagt ggctgcaaaa acttgagaat    180
tacattgtgg aaaacatgaa gtcggagatg cccagatac agcagaatgc agttcagaac    240
```

| | |
|---|---|
| cacacggcta ccatgctgga gataggaacc agcctcctct ctcagactgc agagcagacc | 300 |
| agaaagctga cagatgttga gacccaggta ctaaatcaaa cttctcgact tgagatacag | 360 |
| ctgctggaga attcattatc cacctacaag ctagagaagc aacttcttca acagacaaat | 420 |
| gaaatcttga agatccatga aaaaaacagt ttattagaac ataaaatctt agaaatggaa | 480 |
| ggaaaacaca aggaagagtt ggacacccta aggaagaga aagagaacct tcaaggcttg | 540 |
| gttactcgtc aaacatatat aatccaggag ctggaaaagc aattaaacag agctaccacc | 600 |
| aacaacagtg tccttcagaa gcagcaactg gagctgatgg acacaagaga ctgtgcagat | 660 |
| gtatatcaag ctggttttaa taaaagtgga atctacacta tttatattaa taatatgcca | 720 |
| gaacccaaaa aggtgttttg caatatggat gtcaatgggg gaggttggac tgtaatacaa | 780 |
| catcgtgaag atggaagtct agatttccaa agaggctgga aggaatataa aatgggtttt | 840 |
| ggaaatccct ccggtgaata ttggctgggg aatgagttta ttttttgccat taccagtcag | 900 |
| aggcagtaca tgctaagaat tgagttaatg gactgggaag ggaaccgagc ctattcacag | 960 |
| tatgacagat ccacatagg aaatgaaaag caaaactata ggttgtattt aaaaggtcac | 1020 |
| actgggacag caggaaaaca gagcagcctg atcttacacg gtgctgattt cagcactaaa | 1080 |
| gatgctgata atgacaactg tatgtgcaaa tgtgccctca tgttaacagg aggatggtgg | 1140 |
| tttgatgctt gtggcccctc caatctaaat ggaatgttct atactgcggg acaaaaccat | 1200 |
| ggaaaactga atgggataaa gtggcactac ttcaaagggc ccagttactc cttacgttcc | 1260 |
| acaactatga tgattcgacc tttagatttt tga | 1293 |

<210> SEQ ID NO 28
<211> LENGTH: 1293
<212> TYPE: DNA
<213> ORGANISM: mouse

<400> SEQUENCE: 28

| | |
|---|---|
| atgacagttt tcctttcctt tgcattcttc gctgccattc tgactcacat agggtgcagc | 60 |
| aacaccaacg ctctgcaaag ggatgctcca cacgtggagc cggatttctc ttcccagaaa | 120 |
| cttcagcatc tggagcatgt gatggaaaat tatactcagt ggctgcaaaa acttgagaat | 180 |
| tacattgtgg aaaatatgaa gtcggagatg gcccagatac aacagaatgc tgttcaaaac | 240 |
| cacacggcca ccatgcttga gataggaacc agtctcttat ctcagactgc agagcagacc | 300 |
| cgaaagctga cagatgttga gacccaggta ctaaatcaaa catcccgact tgaaatacaa | 360 |
| ctgctagaga attcattatc aacatacaag ctagagaagc aacttctcca acagacaaat | 420 |
| gaaattctga agattcacga aaaaaacagt ttactagagc acaaaatctt agaaatggag | 480 |
| ggaaaacaca agaagaatt ggacaccttg aaggaggaga agaaaacct tcaaggcttg | 540 |
| gtttctcgtc agacattcat catccaggag ttggagaagc aacttagtag agctaccaac | 600 |
| aacaacagca tcctgcagaa gcaacaactg gagctcatgg acacacgaga ctgtgcagat | 660 |
| gtatatcaag ctggttttaa taaaagtgga atctacacta tttattttaa taatatgcca | 720 |
| gaacccaaaa aggtattttg caatatggat gtgaatgggg gaggttggac agtaatacaa | 780 |
| caccgggaag atggaagcct ggatttccag aggggctgga aggagtataa aatgggtttt | 840 |
| gggaatccct ctggtgaata ttggctcggg aacgagttca ttttttgcaat aaccagtcag | 900 |
| aggcagtaca tgctgaggat tgagctgatg gactgggaag ggaaccgagc ctactcacag | 960 |
| tacgacagat ccacatagg aaatgaaaag cagaactata ggttatattt aaaaggtcac | 1020 |

-continued

```
acagggacag caggcaaaca gagcagcttg atcttacacg gtgctgattt cagcacgaag    1080
gatgctgata acgacaactg tatgtgcaaa tgcgctctca tgctaacagg aggttggtgg    1140
ttcgatgcct gtggcccttc caatctaaat ggaatgttct acactgcggg acaaaatcat    1200
ggaaaactga atgggataaa gtggcactac ttcaaagggc ccagttactc cttacgttcc    1260
accaccatga tgatccggcc cttggacttt tga                                 1293
```

<210> SEQ ID NO 29
<211> LENGTH: 708
<212> TYPE: DNA
<213> ORGANISM: Homo sapiens

<400> SEQUENCE: 29

```
atgacagttt cctttccttt gctttcctc gctgccattc tgactcacat agggtgcagc     60
agagactgtg cagatgtata tcaagctggt tttaataaaa gtggaatcta cactatttat    120
attaataata tgccagaacc caaaaaggtg ttttgcaata tggatgtcaa tgggggaggt    180
tggactgtaa tacaacatcg tgaagatgga agtctagatt ccaaagagg ctggaaggaa     240 tataaaatgg gttttgggaaa tccctccggt gaatattggc tggggaatga gtttattttt    300
gccattacca gtcagaggca gtacatgcta agaattgagt taatggactg ggaagggaac    360
cgagcctatt cacagtatga cagattccac ataggaaatg aaaagcaaaa ctataggttg    420
tatttaaaag gtcacactgg gacagcagga aaacagagca gcctgatctt acacggtgct    480
gatttcagca ctaaagatgc tgataatgac aactgtatgt gcaaatgtgc cctcatgtta    540
acaggaggat ggtggtttga tgcttgtggc ccctccaatc taaatggaat gttctatact    600 gcggacaaa accatggaaa actgaatggg ataaagtggc actacttcaa agggcccagt    660
tactccttac gttccacaac tatgatgatt cgacctttag attttga                  708
```

<210> SEQ ID NO 30
<211> LENGTH: 708
<212> TYPE: DNA
<213> ORGANISM: mouse

<400> SEQUENCE: 30

```
atgacagttt cctttccttt gcattcttc gctgccattc tgactcacat agggtgcagc     60
cgagactgtg cagatgtata tcaagctggt tttaataaaa gtggaatcta cactatttat    120
tttaataata tgccagaacc caaaaaggta ttttgcaata tggatgtgaa tgggggaggt    180
tggacagtaa tacaacaccg ggaagatgga agcctggatt ccagagggg ctggaaggag    240 tataaaatgg gttttgggaa tccctctggt gaatattggc tcgggaacga gttcattttt    300
gcaataacca gtcagaggca gtacatgctg aggattgagt tgatggactg ggaagggaac    360
cgagcctact cacagtacga cagattccac ataggaaatg aaaagcagaa ctataggtta    420
tatttaaaag gtcacacagg gacagcaggc aaacagagca gcttgatctt acacggtgct    480
gatttcagca cgaaggatgc tgataacgac aactgtatgt gcaaatgcgc tctcatgcta    540
acaggaggtt ggtggttcga tgcctgtggc ccttccaatc taaatggaat gttctacact    600 gcggacaaa atcatggaaa actgaatggg ataaagtggc actacttcaa agggcccagt    660
tactccttac gttccaccac catgatgatc cggcccttgg acttttga                 708
```

<210> SEQ ID NO 31
<211> LENGTH: 2149
<212> TYPE: DNA
<213> ORGANISM: Homo sapiens

<400> SEQUENCE: 31

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300
ggcagtacaa tgacagtttt cctttccttt gctttcctcg ctgccattct gactcacata     360
gggtgcagca atcagcgccg aagtccagaa acagtggga gaagatataa ccggattcaa      420
catgggcaat gtgcctacac tttcattctt ccagaacacg atggcaactg tcgtgagagt     480
acgacagacc agtacaacac aaacgctctg cagagagatg ctccacacgt ggaaccggat     540
ttctcttccc agaaacttca acatctggaa catgtgatgg aaaattatac tcagtggctg     600
caaaaacttg agaattacat tgtggaaaac atgaagtcgg agatggccca gatacagcag     660
aatgcagttc agaaccacac ggctaccatg ctggagatag aaccagcct cctctctcag      720
actgcagagc agaccagaaa gctgacagat gttgagaccc aggtactaaa tcaaacttct     780
cgacttgaga tacagctgct ggagaattca ttatccacct acaagctaga gaagcaactt     840
cttcaacaga caaatgaaat cttgaagatc catgaaaaaa acagtttatt agaacataaa     900
atcttagaaa tggaaggaaa acacaaggaa gagttggaca ccttaaagga agagaaagag     960
aaccttcaag gcttggttac tcgtcaaaca tatataatcc aggagctgga aaagcaatta    1020
aacagagcta ccaccaacaa cagtgtcctt cagaagcagc aactggagct gatggacaca    1080
gtccacaacc ttgtcaatct ttgcactaaa gaaggtgttt tactaaaggg aggaaaagaa    1140
gaggaagaga aaccatttag agactgtgca gatgtatatc aagctggttt taataaaagt    1200
ggaatctaca ctatttatat taataatatg ccagaaccca aaaaggtgtt ttgcaatatg    1260
gatgtcaatg ggggaggttg gactgtaata caacatcgtg aagatggaag tctagatttc    1320
caaagaggct ggaaggaata taaaatgggt tttggaaatc cctccggtga atattggctg    1380
gggaatgagt ttattttgc cattaccagt cagaggcagt acatgctaag aattgagtta    1440
atggactggg aagggaaccg agcctattca cagtatgaca gattccacat aggaaatgaa    1500
aagcaaaact ataggttgta tttaaaaggt cacactggga cagcaggaaa acagagcagc    1560
ctgatcttac acggtgctga tttcagcact aaagatgctg ataatgacaa ctgtatgtgc    1620
aaatgtgccc tcatgttaac aggaggatgg tggtttgatg cttgtggccc ctccaatcta    1680
aatgaatgt tctatactgc gggacaaaac catggaaaac tgaatgggat aaagtggcac    1740
tacttcaaag ggcccagtta ctccttacgt tccacaacta tgatgattcg accttttagat    1800
ttttgaaagc gcaatgtcag aagcgattat gaaagcaaca aagaaatccg agaagctgc    1860
caggtgagaa actgtttgaa aacttcagaa gcaaacaata ttgtctccct tccagcaata    1920
agtggtagtt atgtgaagtc accaaggttc ttgaccgtga atctggagcc gtttgagttc    1980
acaagagtct ctacttgggg tgacagtgct cacgtggctc gactatagaa aactccactg    2040
actgtcgggc tttaaaaagg gaagaaactg ctgagcttgc tgtgcttcaa actactactg    2100
gaccttattt tggaactatg gtagccagat gataaatatg gttaatttc                2149
```

<210> SEQ ID NO 32
<211> LENGTH: 2044
<212> TYPE: DNA

<213> ORGANISM: mouse

<400> SEQUENCE: 32

```
ctgacgcggg caggctccac gctgaacggt tacacagaga ggaaacaata aatctaagct    60
actattgcaa taaatatctc aagttttaac gaaggaaact atcattacag ttaaaatttt   120
ttaaagtaac gctttttag aacaaagcta acaaatggct agttttctgt ggatcttctt   180
caaacgcttt ctttaacggg gaaagagtca acaagcagt tttacctgaa ataaagaact   240
agtttaaagg tcagaagaga agagcaagct tgcaggagg cacggaaggc aagcgctggc   300
agtacaatga cagttttcct ttcctttgca ttcttcgctg ccattctgac tcacataggg   360
tgcagcaacc agcgccgaaa tccagaaaac ggagggagaa gatataaccg gattcaacat   420
gggcaatgtg cctacacttt cattcttcca gaacacgacg ggaactgccg tgagagtgcg   480
acagagcagt acaacaccaa cgctctgcaa agggatgctc cacacgtgga gccggatttc   540
tcttcccaga aacttcagca tctggagcat gtgatggaaa attatactca gtggctgcaa   600
aaacttgaga attacattgt ggaaaatatg aagtcggaga tggcccagat acaacagaat   660
gctgttcaaa accacacggc caccatgctt gagataggaa ccagtctctt atctcagact   720
gcagagcaga cccgaaagct gacagatgtt gagacccagg tactaaatca aacatcccga   780
cttgaaatac aactgctaga gaattcatta tcaacataca agctagagaa gcaacttctc   840
caacagacaa atgaaattct gaagattcac gaaaaaaaca gtttactaga gcacaaaatc   900
ttagaaatgg agggaaaaca caaagaagaa ttggacacct tgaaggagga gaaagaaaac   960
cttcaaggct tggtttctcg tcagacattc atcatccagg agttggagaa gcaacttagt  1020
agagctacca acaacaacag catcctgcag aagcaacaac tggagctcat ggacacagtt  1080
cataaccttg tcagcctttg cactaaagaa ggtgttttgc taagggagg aaaaagagaa  1140
gaagagaaac catttcgaga ctgtgcagat gtatatcaag ctggttttaa taaaagtgga  1200
atctacacta tttatttaa taatatgcca gaacccaaaa aggtattttg caatatggat  1260
gtgaatgggg gaggttggac agtaatacaa caccgggaag atggaagcct ggatttccag  1320
aggggctgga aggagtataa aatgggtttt gggaatccct ctggtgaata ttggctcggg  1380
aacgagttca tttttgcaat aaccagtcag aggcagtaca tgctgaggat tgagctgatg  1440
gactgggaag ggaaccgagc ctactcacag tacgacagat tccacatagg aaatgaaaag  1500
cagaactata ggttatattt aaaaggtcac acagggacag caggcaaaca gagcagcttg  1560
atcttacacg gtgctgattt cagcacgaag gatgctgata cgacaactg tatgtgcaaa  1620
tgcgctctca tgctaacagg aggttggtgg ttcgatgcct gtggcccttc caatctaaat  1680
ggaatgttct acactgcggg acaaaatcat ggaaactga atgggataaa gtggcactac  1740
ttcaaagggc ccagttactc cttacgttcc accaccatga tgatccggcc cttggacttt  1800
tgaaggtgct atgccagtat tagaaagctg caaagaaagc tgggcatgtt cccagatgag  1860
aagctagtca gaggcttcag aaacaaccaa cattgtctcc gttccagcag caagtggtta  1920
tgtcatgtca cctgggtact taacaatgga tttgagcctt ctgaggtca acagaatcgc  1980
cacttgggtc cagagaatgc cactcacaat catgtttaaa agggaagaaa cttctcagct  2040
tgct                                                              2044
```

<210> SEQ ID NO 33
<211> LENGTH: 2269
<212> TYPE: DNA
<213> ORGANISM: Homo sapiens

<400> SEQUENCE: 33

```
tgggttggtg tttatctcct cccagccttg agggagggaa caacactgta ggatctgggg      60
agagaggaac aaaggaccgt gaaagctgct ctgtaaaagc tgacacagcc ctcccaagtg     120
agcaggactg ttcttcccac tgcaatctga cagtttactg catgcctgga gagaacacag     180
cagtaaaaac caggtttgct actggaaaaa gaggaaagaa aagactttca ttgacggacc     240
cagccatggc agcgtagcag ccctgcgttt cagacggcag cagctcggga ctctggacgt     300
gtgtttgccc tcaagtttgc taagctgctg gtttattact gaagaaagaa tgtggcagat     360
tgttttcttt actctgagct gtgatcttgt cttggccgca gcctataaca actttcggaa     420
gagcatggac agcataggaa agaagcaata tcaggtccag catgggtcct gcagctacac     480
tttcctcctg ccagagatgg acaactgccg ctcttcctcc agcccctacg tgtccaatgc     540
tgtgcagagg gacgcgccgc tcgaatacga tgactcggtg cagaggctgc aagtgctgga     600
gaacatcatg gaaacaacaa ctcagtggct aatgaagctt gagaattata tccaggacaa     660
catgaagaaa gaaatggtag agatacagca gaatgcagta cagaaccaga cggctgtgat     720
gatagaaata gggacaaacc tgttaaacca aacagctgag caaacgcgga agttaactga     780
tgtggaagcc caagtattaa atcagaccac gagacttgaa cttcagctct tggaacactc     840
cctctcgaca aacaaattgg aaaaacagat tttggaccag accagtgaaa taaacaaatt     900
gcaagataag aacagtttcc tagaaaagaa ggtgctagct atggaagaca agcacatcat     960
ccaactacag tcaataaaag aagagaaaga tcagctacag gtgttagtat ccaagcaaaa    1020
ttccatcatt gaagaactag aaaaaaaaat agtgactgcc acggtgaata attcagttct    1080
tcaaaagcag caacatgatc tcatggagac agttaataac ttactgacta tgatgtccac    1140
atcaaactca gctaaggacc ccactgttgc taaagaagaa caaatcagct tcagagactg    1200
tgctgaagta ttcaaatcag gacacaccac aaatggcatc tacacgttaa cattccctaa    1260
ttctacagaa gagatcaagg cctactgtga catggaagct ggaggaggcg ggtggacaat    1320
tattcagcga cgtgaggatg gcagcgttga ttttcagagg acttggaaag aatataaagt    1380
gggatttggt aacccttcag gagaatattg gctgggaaat gagtttgttt cgcaactgac    1440
taatcagcaa cgctatgtgc ttaaaataca ccttaaagac tgggaaggga atgaggctta    1500
ctcattgtat gaacatttct atctctcaag tgaagaactc aattatagga ttcaccttaa    1560
aggacttaca gggacagccg gcaaaataag cagcatcagc caaccaggaa atgattttag    1620
cacaaaggat ggagacaacg acaaatgtat ttgcaaatgt tcacaaatgc taacaggagg    1680
ctggtggttt gatgcatgtg gtccttccaa cttgaacgga atgtactatc cacagaggca    1740
gaacacaaat aagttcaacg gcattaaatg gtactactgg aaaggctcag gctattcgct    1800
caaggccaca accatgatga tccgaccagc agatttctaa acatcccagt ccacctgagg    1860
aactgtctcg aactattttc aaagacttaa gcccagtgca ctgaaagtca cggctgcgca    1920
ctgtgtcctc ttccaccaca gagggcgtgt gctcggtgct gacgggaccc acatgctcca    1980
gattagagcc tgtaaacttt atcacttaaa cttgcatcac ttaacggacc aaagcaagac    2040
cctaaacatc cataattgtg attagacaga acacctatgc aaagatgaac ccgaggctga    2100
gaatcagact gacagtttac agacgctgct gtcacaacca agaatgttat gtgcaagttt    2160
atcagtaaat aactgaaaaa cagaacactt atgttataca atacagatca tcttggaact    2220
gcattcttct gagcactgtt tatacactgt gtaaatacccc atatgtcct               2269
```

<210> SEQ ID NO 34
<211> LENGTH: 2424
<212> TYPE: DNA
<213> ORGANISM: mouse
<220> FEATURE:
<221> NAME/KEY: misc_feature
<222> LOCATION: (2308)..(2308)
<223> OTHER INFORMATION: n is a, c, g, or t

<400> SEQUENCE: 34

```
ggctgctcct tcctctcagg acagctccga gtgtgccggg gagaagagaa gagaagagac      60
aggcactggg aaagagcctg ctgcgggacg gagaaggctc tcactgatgg acttattcac     120
acggcacagc cctgtgcctt agacagcagc tgagagctca ggacgcaagt ttgctgaact     180
cacagtttag aacccaaaaa gagagagaga atgtggcaga tcattttcct aactttggc     240
tgggatcttg tcttggcctc agcctacagt aactttagga gagcgtgga cagcacaggc     300
agaaggcagt accaggtcca gaacggaccc tgcagctaca cgttcctgct gccggagacc     360
gacagctgcc gatcttcctc cagcccctac atgtccaatg ccgtgcagag ggatgcaccc     420
ctcgactacg acgactcagt gcaaaggctg caggtgctgg agaacattct agagaacaac     480
acacagtggc tgatgaagct ggagaattac attcaggaca catgaagaa ggagatggtg     540
gagatccaac agaatgtggt gcagaaccag acagctgtga tgatagagat tggaaccagc     600
ttgctgaacc agacagcagc acaaactcgg aaactgactg atgtggaagc ccaagtacta     660
aaccagcga caagactcga gctgcagctt ctccaacatt ctatttctac caacaaattg     720
gaaaagcaga ttttggatca gaccagtgaa ataaacaagc tacaaaataa gaacagcttc     780
ctagaacaga aagttctgga catggagggc aagcacagcg agcagctaca gtccatgaag     840
gagcagaagg acgagctcca ggtgctggtg tccaagcaga gctctgtcat tgacgagctg     900
gagaagaagc tggtgacagc cacggtcaac aactcgctcc ttcagaagca gcagcatgac     960
ctaatggaga ccgtcaacag cttgctgacc atgatgtcat cacccaactc caagagctcg    1020
gttgctatcc gtaaagaaga gcaaaccacc ttcagagact gtgcggaaat cttcaagtca    1080
ggactcacca ccagtggcat ctacacactg accttcccca ctccacaga ggagatcaag    1140
gcctactgtg acatggacgt gggtggagga gggtggacag tcatccaaca ccgagaagat    1200
ggcagtgtgg acttccagag gacgtggaaa gaatacaaag agggcttcgg gaaccctctg    1260
ggagagtact ggctgggcaa tgagtttgtc tcccagctga ccggtcagca ccgctacgtg    1320
cttaagatcc agctgaagga ctgggaaggc aacgaggcgc attcgctgta tgatcacttc    1380
tacctcgctg gtgaagagtc caactacagg attcacctta caggactcac ggggaccgcg    1440
gccaaaataa gtagcatcag ccaaccagga agtgatttta gcacaaagga ttcggacaat    1500
gacaaatgca tctgcaagtg ttcccagatg ctctcaggag ctggtggtt tgacgcatgt    1560
ggtccttcca acttgaatgg acagtactac ccacaaaaac agaatacaaa taagtttaac    1620
ggtatcaagt ggtactactg gaaggggtcc ggctactcgc tcaaggccac aaccatgatg    1680
atccggccag cagatttcta aatgcctgcc tacactacca gaagaacttg ctgcatccaa    1740
agattaactc caaggcactg agagacacca gtgcatagca gcccctttcc acatcaggaa    1800
gtgctcctgg gggtggggag ggtctgtgtg taccagactg aagcgcatca cttaagcctg    1860
caccgctaac caaccaaagg cactgcagtc tggagaaaca cttctgggaa ggttgtggct    1920
gaggatcaga aggacagcgt gcagactctg tcacaaggaa gaatgttccg tgggagttca    1980
gcagtaaata actggaaaac agaacactta gatggtgcag ataaatcttg ggaccacatt    2040
```

```
cctctaagca cggtttctag agtgaataca ttcacagctc ggctgtcaca atgcaaggc      2100 cgtgtcctcg cactgtggca gccagtatcc agggacttct aagtggtggg cacaggctat     2160
catctggaga agcacacatt cattgttttc ctcttgggtg cttaacatgt tcatttgaaa     2220
acaacacatt tacctatctt gatggcttag tttttaatgg ctggctacta tttactatat    2280
ggcaaaaatg cccacatctc tggaatancc accaaataag cgccatgttg gtgaatgcgg    2340
aggctgtact attttgtttt cttcctggct ggtaaatatg aaggtatttt tagtaattaa    2400
atataagtta ttagttgaaa gacc                                            2424

<210> SEQ ID NO 35
<211> LENGTH: 1957
<212> TYPE: DNA
<213> ORGANISM: Homo sapiens
<220> FEATURE:
<221> NAME/KEY: misc_feature
<222> LOCATION: (1497)..(1497)
<223> OTHER INFORMATION: n is a, c, g, or t

<400> SEQUENCE: 35
ggtgcagctg caggcaagcc tggccactgt tggctgcagc aggacatccc aggcacagcc       60
cctagggctc tgagcagaca tccctcgcca ttgacacatc ttcagatgct ctcccaacta     120
gccatgctgc agggcagcct cctccttgtg gttgccacca tgtctgtggc tcaacagaca     180
aggcaggagg cggatagggg ctgcgagaca cttgtagtcc agcacggcca ctgtagctac     240
accttcttgc tgcccaagtc tgagccctgc cctccggggc tgaggtctc cagggactcc      300 aacaccctcc agagagaatc actggccaac ccactgcacc tggggaagtt gcccacccag     360
caggtgaaac agctggagca ggcactgcag aacaacacgc agtggctgaa gaagctagag     420
agggccatca gacgatcttt gaggtcgaag ctggagcagg tccagcagca aatggcccag     480
aatcagacgg cccccatgct agagctgggc accagcctcc tgaaccagac cactgcccag     540
atccgcaagc tgaccgacat ggaggctcag ctcctgaacc agacatcaag aatggatgcc     600
cagatgccag agacctttct gtccaccaac aagctggaga accagctgct gctacagagg     660
cagaagctcc agcagcttca gggccaaaac agcgcgctcg agaagcggtt gcaggccctg     720
gagaccaagc agcaggagga gctggccagc atcctcagca agaaggcgaa gctgctgaac     780
acgctgagcc gccagagcgc cgccctcacc aacatcgagc gcggcctgcg cggtgtcagg     840
cacaactcca gcctcctgca ggaccagcag cacagcctgc gccagctgct ggtgttgttg     900
cggcacctgg tgcaagaaag ggctaacgcc tcggccccgg ccttcataat ggcaggtgag     960
caggtgttcc aggactgtgc agagatccag cgctctgggg ccagtgccag tggtgtgtac    1020
accatccagg tgtccaatgc aacgaagccc aggaaggtgt tctgtgacct gcagagcagt    1080
ggaggcaggt ggaccctcat ccagcgccgt gagaatggca ccgtgaattt tcagcggaac    1140
tggaaggatt acaaacaggg cttcggagac ccagctgggg agcactggct gggcaatgaa    1200
gtggtgcacc agctcaccag aagggcagcc tactctctgc gtgtggagct gcaagactgg    1260
gaaggccacg aggcctatgc ccagtacgaa catttccacc tgggcagtga gaaccagcta    1320
tacaggcttt ctgtggtcgg gtacagcggc tcagcagggc gccagagcag cctggtcctg    1380
cagaacacca gctttagcac ccttgactca gacaacgacc actgtctctg caagtgtgcc    1440
caagtgatgt ctggagggtg gtggtttgac gcctgtggcc tgtcaaacct caacggngtc    1500
tactaccacg ctcccgacaa caagtacaag atggacggca tccgctggca ctacttcaag    1560
```

| | | | | |
|---|---|---|---|---|
| ggccccagct | actcactgcg | tgcctctcgc | atgatgatac | ggcctttgga catctaacga | 1620 |
| gcagctgtgc | cagaggctgg | accacacagg | agaagctcgg | acttggcact cctggacaac | 1680 |
| ctggacccag | atgcaagaca | ctgtgccacc | gccttccctg | cacccctggg cttcctgagc | 1740 |
| cagccctcct | tgacccagaa | gtccagaagg | gtcatctgcc | ccccactcc cctccgtctg | 1800 |
| tgacatggag | ggtgttcggg | cccatccct | ctgatgtagt | cctcgcccct cttctctccc | 1860 |
| tccccttca | ggggctccct | gcctgagggt | cacagtacct | tgaatgggct gagaacagac | 1920 |
| caaaaaaaa | aaaaaaaaa | aaaaaaaaa | aaaaaa | | 1957 |

<210> SEQ ID NO 36
<211> LENGTH: 1530
<212> TYPE: DNA
<213> ORGANISM: mouse

<400> SEQUENCE: 36

| | | | | | |
|---|---|---|---|---|---|
| atgctctgcc | agccagctat | gctactagat | ggcctcctcc | tgctggccac catggctgca | 60 |
| gcccagcaca | gagggccaga | agccggtggg | caccgccaga | ttcaccaggt ccggcgtggc | 120 |
| cagtgcagct | acacctttgt | ggtgccggag | cctgatatct | gccagctggc gccgacagcg | 180 |
| gcgcctgagg | ctttgggggg | ctccaatagc | ctccagaggg | acttgcctgc ctcgaggctg | 240 |
| cacctaacag | actggcgagc | cagagggcc | cagcgggccc | agcgtgtgag ccagctggag | 300 |
| aagatactag | agaataacac | tcagtggctg | ctgaagctgg | agcagtccat caaggtgaac | 360 |
| ttgaggtcac | acctggtgca | ggcccagcag | gacacaatcc | agaaccagac aactaccatg | 420 |
| ctggcactgg | gtgccaacct | catgaaccag | accaaagctc | agacccacaa gctgactgct | 480 |
| gtggaggcac | aggtcctaaa | ccagacattg | cacatgaaga | cccaaatgct ggagaactca | 540 |
| ctgtccacca | caagctgga | gcggcagatg | ctgatgcaga | ccgagagct gcagcggctg | 600 |
| cagggtcgca | cagggccct | ggagaccagg | ctgcaggcac | tggaagcaca acatcaggcc | 660 |
| cagcttaaca | gcctccaaga | gaagagggaa | caactgcaca | gtctcctggg ccatcagacc | 720 |
| gggaccctgg | ctaacctgaa | gcacaatctg | cacgctctca | gcagcaattc cagctccctg | 780 |
| cagcagcagc | agcagcaact | gacggagttt | gtacagcgcc | tggtacggat gtagcccag | 840 |
| gaccagcatc | cggtttcctt | aaagacacct | aagccagtgt | tccaggactg tgcagagatc | 900 |
| aagcgctccg | ggttaatac | cagcggtgtc | tataccatct | atgagaccaa catgacaaag | 960 |
| cctctcaagg | tgttctgtga | catggagact | gatggaggtg | gctggaccct catccagcac | 1020 |
| cgggaggatg | gaagcgtaaa | tttccagagg | acctgggaag | aatacaaaga gggttttggt | 1080 |
| aatgtggcca | gagagcactg | gctgggcaat | gaggctgtgc | accgcctcac cagcagaacg | 1140 |
| gcctacttgc | tacgcgtgga | actgcatgac | tgggaaggcc | gccagacctc catccagtat | 1200 |
| gagaacttcc | agctgggcag | cgagaggcag | cggtacagcc | tctctgtgaa tgacagcagc | 1260 |
| agttcagcag | ggcgcaagaa | cagcctggct | cctcagggca | ccaagttcag caccaaagac | 1320 |
| atggacaatg | ataactgcat | gtgtaaatgt | gctcagatgc | tgtctggagg tggtggttt | 1380 |
| gatgcctgtg | gcctctccaa | cctcaatggc | atctactatt | cagttcatca gcacttgcac | 1440 |
| aagatcaatg | gcatccgctg | gcactacttc | cgaggcccca | gctactcact gcacggcaca | 1500 |
| cgcatgatgc | tgaggccaat | gggtgcctga | | | 1530 |

COMPOSITIONS OF ANGIOPOIETIN, FRAGMENTS, MUTANTS AND ANALOGS THEREOF AND USES OF THE SAME

CROSS REFERENCE TO RELATED APPLICATIONS

This application claims priority to U.S. Provisional Ser. No. 60/450,582 filed Feb. 27, 2003, which is incorporated herein by reference.

GOVERNMENT SUPPORT

This invention was made with U.S. Government support (NIH Grant No. 1RO1HL074117) and the U.S. Government may therefore have certain rights in the invention.

FIELD OF THE INVENTION

The present invention relates activities of Angiopoietin-1 (Ang-1) and Angiopoietin-2 (Ang-2) and to uses of compounds having such activities to treat diseases and disorders and find additional compounds.

BACKGROUND OF THE INVENTION

Angiogenesis plays an important role in embryogenesis and tumorigenesis. It is a complicated multistep process, which includes the dynamic changes of cell-cell and cell-matrix interactions, endothelial cell proliferation and migration, recruitment of the peri-vascular supporting cells, and the maturation process. Numerous molecules are involved in those processes, including growth factors and their receptors, proteases, adhesion receptors, and the ECM1 components. VEGF and angiopoietin families play special roles in angiogenesis due to the restricted expression of their receptors.

Ang-1 and Ang-2 are approximately 70 kDa proteins with considerable sequence homology that consist of a signal peptide, an N-terminal coiled-coil domain, a short linker peptide region, and a C-terminal fibrinogen homology domain (FHD). The coiled-coil region is responsible for dimerization/multimerization of angiopoietins, and the fibrinogen homology domain binds to Tie-2 receptor. Both Ang-1 and Ang-2 form dimers and oligomers.

Ang-1 and Ang-2 have antagonistic roles. Ang-1 induces tyrosine phosphorylation of Tie-2 receptor and promotes recruitment of the pericytes and smooth muscle cells, thereby playing a role in establishing and maintaining the vascular integrity. As an antagonist of Tie-2 receptor, Ang-2 competes with Ang-1 for the binding of Tie-2, Ang-2 blocks the phosphorylation of Tie-2 receptors induced by Ang-1, and Ang-2 loosens the interactions between endothelial and peri-vascular support cells and ECM.

Targeted disruption of Ang-1 and Tie-2 and overexpression of Ang-2 resulted in embryonic death with the similar vascular defects. These mice have normal primary vascular development, but the remodeling and maturation of the vasculature are defective. The transgenic mice overexpressing Ang-1 displayed increased vascularization and decreased adult vasculature leakage. Together, these results indicated that Ang-1 plays an indispensable role in the formation of blood vessels during mouse development by recruiting and maintaining peri-endothelial support cells.

Several studies have offered possible mechanisms for the pro-angiogenic effect of Ang-1. Although Ang-1 does not stimulate the proliferation of endothelial cells, it stimulates endothelial cell migration, induces the capillary-like tubule formation, and promotes survival of endothelial cells. Ang-1 inhibits apoptosis of endothelial cells via the phosphatidylinositol 3-kinase/Akt pathway.

Angiogenesis is regulated by the precise balance between pro- and anti-angiogenic factors. Ang-2 expression is often induced in the endothelia undergoing active remodeling or regression, by hypoxia, and several growth factors, including VEGF. Ang-2 destabilizes the vasculature. Thus, Ang-2 initiates angiogenesis in the presence of VEGF, which supplies endothelial cells with necessary survival and proliferation signals, or induces apoptosis of endothelial cells in the absence of the pro-angiogenic factors.

SUMMARY OF THE INVENTION

One aspect of the present invention relates to pharmaceutical compositions that comprise a pharmaceutically acceptable carrier and either a therapeutically effective amount of an ECM-binding fragment of Ang-1 protein that comprises SEQ ID NO:1, SEQ ID NO: 2, SEQ ID NO:3, and/or SEQ ID NO:4 or a homologous peptide thereof.

Another aspect of the invention relates to pharmaceutical compositions that comprise a pharmaceutically acceptable carrier and a therapeutically effective amount of a non-ECM binding fragment of Ang-1 protein that comprises a modification in an ECM-binding domain of Ang-1, wherein said modification reduces the binding of Ang-1 to an extracellular matrix (ECM) and/or a vector comprising a nucleic acid molecule that comprises the nucleotide sequence that encodes a non-ECM binding fragment of Ang-1 protein that comprises a modification in an ECM-binding domain of Ang-1, wherein said modification reduces the binding of Ang-1 to the ECM.

Another aspect of the invention relates to pharmaceutical compositions that comprise a pharmaceutically acceptable carrier and a therapeutically effective amount of a proteolytic resistant fragment of Ang-1 protein that comprises a modification in a proteolytic domain of Ang-1, wherein said modification inhibits the proteolysis of Ang-1 and/or a vector comprising a nucleic acid molecule that comprises the nucleotide sequence that encodes a proteolytic resistant fragment of Ang-1 protein that comprises a modification in a proteolytic domain of Ang-1, wherein said modification inhibits the proteolysis of Ang-1.

Another aspect of the present invention relates to pharmaceutical compositions that comprise a pharmaceutically acceptable carrier and a vector comprising a nucleic acid molecule that comprises a nucleotide sequence that encodes an ECM-binding fragment of Ang-1 protein that comprises SEQ ID NO:1, SEQ ID NO: 2, SEQ ID NO:3, and/or SEQ ID NO:4 or a homologous peptide thereof.

One aspect of the present invention relates to pharmaceutical compositions that comprise a pharmaceutically acceptable carrier and either a therapeutically effective amount of a mutant Ang-1 which retains their angiogenesis promoting activity but which have reduced or inactive ECM binding or a homologous peptide thereof or mutant versions of Ang-1.

Another aspect of the present invention relates to pharmaceutical compositions that comprise a pharmaceutically acceptable carrier and a vector comprising a nucleic acid molecule that comprises a nucleotide sequence that encodes a mutant Ang-1 which retains their angiogenesis promoting activity but which have reduced or inactive ECM binding or a homologous peptide thereof.

One aspect of the present invention relates to pharmaceutical compositions that comprise a pharmaceutically acceptable carrier and either a therapeutically effective amount of a mutant Ang-1 which retain their angiogenesis promoting activity but which is not cleaved into a antagonist fragment or a homologous peptide thereof.

Another aspect of the present invention relates to pharmaceutical compositions that comprise a pharmaceutically acceptable carrier and a vector comprising a nucleic acid molecule that comprises the nucleotide sequence that encodes a mutant Ang-1 which retain their angiogenesis promoting activity but which is not cleaved into a antagonist fragment or a homologous peptide thereof.

An aspect of the invention relates to methods of treating an individual suspected of having coronary artery disease, vascular disease, hemorrhage or a condition involving ischemia. Another aspect of the invention provides methods of promoting angiogenesis, endothelial survival and maintaining vascular integrity in an individual A further aspect of the present invention provides methods to effectively promote angiogenesis in the patients with the diseases related to lack of blood vessels such as ischemia in hearts and limbs.

The present invention provides methods to reduce stroke, heart attack, blood vessel blockage, hemorrhage, artherosclerosis risk by maintain the health and integrity of blood vessels (by reduce the loss the endothelial monolayer integrity and attachment of blood cells on vessel walls).

The present invention provides methods to assist the recovery of the patients who had stroke and the angioplasty procedure by promoting the growth/survival of endothelial cells and establish endothelial monolayer and inhibit excessive inflammation, hemorrhage (by blocking influx of blood and immune cells), and proliferation of vascular smooth muscle.

The present invention provides methods to treat patients with restenosis by inhibiting re-closure of blood vessel after inserting stents into blood vessels.

The present invention provide methods to make stable and functional artificial blood vessels.

In some embodiments, the methods comprise the step of administering to the individual a pharmaceutical composition that comprises a therapeutically effective amount of an ECM-binding fragment of Ang-1 protein that comprises SEQ ID NO:1, SEQ ID NO: 2, SEQ ID NO:3, and/or SEQ ID NO:4 or a homologous peptide thereof. In some embodiments, the methods comprise the step of administering to the individual pharmaceutical compositions that comprises a vector comprising a nucleic acid molecule that comprises the nucleotide sequence that encodes an ECM-binding fragment of Ang-1 protein that comprises SEQ ID NO:1, SEQ ID NO: 2, SEQ ID NO:3, and/or SEQ ID NO:4 or a homologous peptide thereof.

In some embodiments, the methods comprise the step of administering to the individual a pharmaceutical composition that comprises a therapeutically effective amount of a mutant Ang-1 which retain their angiogenesis promoting activity but which have reduced ECM biding activity, or a homologous peptide thereof. In some embodiments, the methods comprise the step of administering to the individual pharmaceutical compositions that comprises a vector comprising a nucleic acid molecule that comprises the nucleotide sequence that encodes a mutant Ang-1 which retain their angiogenesis promoting activity but which have reduced ECM biding activity or a homologous peptide thereof.

In some embodiments, the methods comprise the step of administering to the individual a pharmaceutical composition that comprises a therapeutically effective amount of a mutant Ang-1 which retain their angiogenesis promoting activity but which has is not cleaved into a antagonist fragment or a homologous peptide thereof, or a homologous peptide thereof. In some embodiments, the methods comprise the step of administering to the individual pharmaceutical compositions that comprises a vector comprising a nucleic acid molecule that comprises the nucleotide sequence that encodes a mutant Ang-1 which retain their angiogenesis promoting activity but which has is not cleaved into a antagonist fragment or a homologous peptide thereof.

According to some other aspects of the invention, methods are provided to identify compounds that modulates binding of Ang-1 to ECM. The methods comprise performing a test assay that comprises the steps of contacting a protein that comprises at least an ECM-binding fragment of Ang-1 protein that comprises SEQ ID NO:1, SEQ ID NO: 2, SEQ ID NO:3, and/or SEQ ID NO:4 with ECM material in the presence of a test compound, then measuring the level of binding of the protein that comprises at least an ECM-binding fragment of Ang-1 protein that comprises SEQ ID NO:1, SEQ ID NO: 2, SEQ ID NO:3, and/or SEQ ID NO:4 with the ECM; and then comparing the level with the level of binding of protein that comprises at least an ECM-binding fragment of Ang-1 protein that comprises SEQ ID NO:1, SEQ ID NO: 2, SEQ ID NO:3, and/or SEQ ID NO:4 with ECM material in the absence of the test compound. When the level of binding of the protein that comprises at least an ECM-binding fragment of Ang-1 protein that comprises SEQ ID NO:1, SEQ ID NO: 2, SEQ ID NO:3, and/or SEQ ID NO:4 with the ECM in the presence of the test compound is less than the level of binding of the protein that comprises at least an ECM-binding fragment of Ang-1 protein that comprises SEQ ID NO:1, SEQ ID NO: 2, SEQ ID NO:3, and/or SEQ ID NO:4 with the ECM in the absence of the test compound results indicate that the test compound modulates binding of Ang-1 to ECM by inhibiting the binding. When the level of binding of the protein that comprises at least an ECM-binding fragment of Ang-1 protein that comprises SEQ ID NO:1, SEQ ID NO: 2, SEQ ID NO:3, and/or SEQ ID NO:4 with the ECM in the presence of the test compound is more than the level of binding of the protein that comprises at least an ECM-binding fragment of Ang-1 protein that comprises SEQ ID NO:1, SEQ ID NO: 2, SEQ ID NO:3, and/or SEQ ID NO:4 with the ECM in the absence of the test compound results indicate that the test compound modulates binding of Ang-1 to ECM by enhancing the binding.

A further aspect of the invention provides pharmaceutical compositions which comprise a therapeutically effective amount of an Ang-1 fragment with antagonist activity or a homologous peptide thereof and/or a vector comprising a nucleic acid molecule that comprises the nucleotide coding sequence of an Ang-1 fragment with antagonist activity or a homologous peptide thereof, in each case with our without a therapeutically effective amount of Ang-2 protein activity or a homologous peptide thereof and/or a vector comprising a nucleic acid molecule that comprises the nucleotide coding sequence of Ang-2 activity or a homologous peptide thereof.

Additional aspects of the invention provide for methods of treating an individual suspected of having cancer. The methods comprise the step of administering to the individual a pharmaceutical compositions which comprise a therapeutically effective amount of an Ang-1 fragment with antagonist activity or a homologous peptide thereof and/or a vector comprising a nucleic acid molecule that comprises the nucleotide coding sequence of an Ang-1 fragment with antagonist activity or a homologous peptide thereof, in each case with our without a therapeutically effective amount of Ang-2 protein activity or a homologous peptide thereof and/or a vector comprising a nucleic acid molecule that comprises the nucleotide coding sequence of Ang-2 activity or a homologous peptide thereof. In some embodiments, the methods comprise administering the pharmaceutical composition in conjunction with removal or elimination of a tumor.

Additional aspects of the invention provides for methods of treating an individual to inhibit arthritis and diabetes, particularly those identified as being at an elevated risk for such conditions. The methods comprise the step of administering to the individual a pharmaceutical compositions which comprise a therapeutically effective amount of an Ang-1 fragment with antagonist activity or a homologous peptide thereof and/or a vector comprising a nucleic acid molecule that comprises the nucleotide coding sequence of an Ang-1 fragment with antagonist activity or a homologous peptide thereof and/or a therapeutically effective amount of Ang-2 protein activity or a homologous peptide thereof and/or a vector comprising a nucleic acid molecule that comprises the nucleotide coding sequence of Ang-2 activity or a homologous peptide thereof.

Another aspect of the invention relates to improved proteins which comprise at least one of ECM binding motif comprising SEQ ID NO:1, SEQ ID NO: 2, SEQ ID NO:3, and/or SEQ ID NO:4 and/or ECM binding motifs comprising at least one modifications in a sequence comprising SEQ ID NO:1, SEQ ID NO: 2, SEQ ID NO:3, and/or SEQ ID NO:4. Such proteins are useful as pharmaceuticals because the presence of the motif in the proteins results in the protein being retained locally at the intended sites rather than diffusing to other areas. The linker peptide region and/or the coiled-coil ECM-binding region of Ang-1 that anchors Ang-1 to the ECM can be thus used as "the ECM anchor motif" to generate fusion proteins by fusing one or more of the linker peptide and/or the coiled-coil ECM-binding region to the intended proteins to make these proteins bound to the ECM and retained at sites of application.

Another aspect of the invention involves diagnostic methods to detect the serum concentration of Ang-2 and/or c-Ang-1 (antagonist fragment of Ang-1) as an indicator for the need for post surgery use of Ang-2 and/or c-Ang-1 to inhibit progression of metastasis by blocking the transformation of micrometastases to life-threatening macrometastases.

Another aspect of the invention involves diagnostic methods to detect the serum concentration of Ang-1 as an diagnostic and prognosis marker for aggressive malignant cancers.

Another aspect of the invention relates to methods of inhibiting Erk1/2 phosphorylation in a cell comprising administering a composition comprising administering an effective amount of a phosphorylation inhibition fragment of Ang-1 to said cell.

Another aspect of the invention relates to methods of inhibiting tumor angiogenesis in an animal comprising administering a therapeutically effective amount of a pharmaceutical composition comprising an angiogenesis inhibiting fragment of Ang-1.

Another aspect of the invention relates to fusion proteins comprising SEQ ID NOs: 1, 2, 3, 4, 5, 6, 7, 8, 9, 10, 11, and/or 12 and non-Ang-1 protein.

The present invention also relates to a nucleic acid molecule encoding a fusion protein comprising SEQ ID NOs: 1, 2, 3, 4, 5, 6, 7, 8, 9, 10, 11, and/or 12 and non-Ang-1 protein.

DETAILED DESCRIPTION OF PREFERRED EMBODIMENTS

Figure 1:
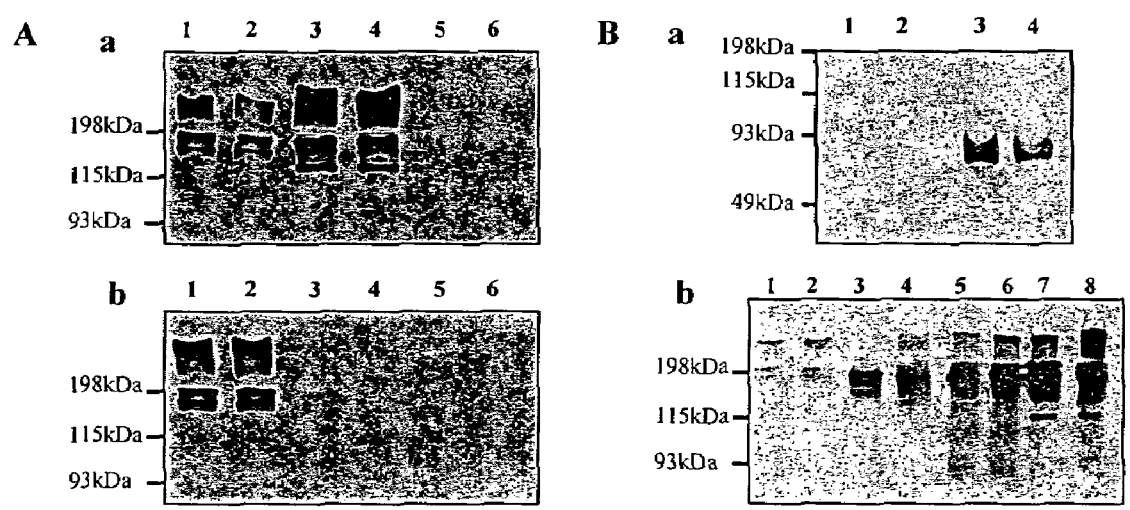
FIG. 1: Ang-1 and Ang-2 displayed different capacity to bind to the ECM and to disseminate from their production sites in vivo. A. Ang-1$_{human}$ is incorporated into the ECM. The distribution of Ang-1$_{human}$ and Ang-2 human in cell culture supernatants (A-a) and the ECM (A-b) of the transiently transfected Cos-7 cells were determined by Western blotting with anti-v5 mAb (Invitrogen). The ECM materials deposited on the culture dishes by the transfected cells were extracted by 2×SDS buffer. The Western blotting was performed under non-reducing conditions using the proteins derived from two independently transfected Cos-7 cells with Ang-1$_{human}$ (lanes 1-2), Ang-2$_{human}$ (lanes 3-4), or the expression vectors alone (lane 5-6). B. The ECM-binding blocks dissemination of Ang-1 form its production site in vivo. The presence of Ang-1v5 and Ang-2v5 proteins in two independent blood samples (a) and solid tumors (b) are shown. Immunoprecipitation was performed with anti-v5-agarose beads using the blood samples derived from the mice bearing the subcutaneous solid tumors of LLCAng-1 (B-a, lanes 1-2) or LLCAng-2 cells (B-a, lanes 3-4). The immunoprecipitated proteins were analyzed by Western blotting with anti-v5 mAb under reducing conditions. The solid tumors were derived from LLCAng-1 (B-b, lanes 1-4) or LLCAng-2 (B-b, lanes 5-9) and extracted with the phosphate buffer (B-b, lanes 1-2, and 5-6), then with 3M urea (B-b, lanes 3-4, and 7-8).

As used herein, the term "ECM" refers to the extracellular matrix. The extracellular matrix (ECM) is a complex structural entity surrounding and supporting cells that are found within mammalian tissues. The ECM comprises structural proteins (collagen and elastin), specialized proteins (e.g. fibrillin, fibronectin, and laminin), and proteoglycans. Proteoglycans are composed of a protein core to which is attached long chains of repeating disaccharide units termed of glycosaminoglycans (GAGs) forming extremely complex high molecular weight components of the ECM.

Although the specific procedures and methods described herein are exemplified using several specific peptides derived from Angiopoietin-1 and -2, they are merely illustrative for the practice of the invention. Analogous procedures and techniques, as well as functionally equivalent peptides and peptide homologues, as will be apparent to those of skill in the art based on the detailed disclosure provided herein are also encompassed by the invention.

Aspects of the present invention arises from the discovery that angiopoietin-1 (Ang-1) associates with extracellular matrix (ECM), and the function of Ang-1 is regulated by the association with the ECM. Thus, while Ang-1 promotes angiogenesis when not associated with the ECM, it is inhibited from promoting angiogenesis while associated with the ECM.

The amino acid sequence of angiopoietin-1, angiopoietin-2 (Ang-2), and angiopoietin-3 (Ang-3) and the nucleotide sequences encoding them are well known in the art. In some embodiments the amino acid sequence of Ang-1 comprises SEQ ID NOs: 13 or 14 and is encoded by a nucleotide sequence comprising SEQ ID NOs: 31 or 32. In some embodiments the amino acid sequence of Ang-2 comprises SEQ ID NOs: 15 or 16 and is encoded by a nucleotide sequence comprising SEQ ID NOs: 33 or 34. In some embodiments the amino acid sequence of Ang-3 comprises SEQ ID NOs: 17 or 18 and is encoded by a nucleotide sequence comprising SEQ ID NOs: 35 or 36.

According to some embodiments the present invention provides for pharmaceutical compositions comprising a pharmaceutically acceptable carrier and a therapeutically effective amount of an ECM-binding fragment of the Ang-1 protein and/or a vector comprising a nucleic acid molecule that comprises the nucleotide sequence that encodes an ECM-binding fragment of Ang-1 protein.

As used herein, the term "ECM-binding fragment of Ang-1 protein" refers to any peptide sequence that comprises a peptide fragment from Ang-1 that can bind to the ECM. In some embodiments the ECM-binding fragment of Ang-1 protein comprises SEQ ID NOs: 1, 2, 3, or 4. In some embodiments, the ECM-binding fragment of Ang-1 may include one or more ECM-binding fragments. In some embodiments, an ECM-binding fragment comprises only one ECM binding fragment. The fragment may be the entire Ang-1 protein or it may be a fragment of the Ang-1 protein. In some embodiments, the ECM-binding fragment of Ang-1 protein may be a part of a fusion protein that comprises Ang-1 protein sequence and non-Ang-1 protein sequence. In some embodiments the ECM-binding fragment of Ang-1 protein is at least 20, at least 50, at least 75, at least 100, at least 500, at least 1000 amino acid residues long.

As used herein, the term "coiled-coil ECM-binding region" refers to an Ang-1 coiled-coil region which is capable of binding to the ECM. In some embodiments, the coiled-coil ECM-binding region comprises an amino acid sequence comprising SEQ ID NOs: 3 or 4 or is encoded by a nucleotide sequence comprises SEQ ID NOs: 21 or 22.

As used herein, the term "linker peptide region", "linker sequence" or "linker protein" refers the sequence present in Ang-1 and/or Ang-2 that is between the N-terminal coiled-coil domain and the C-terminal fibrinogen homology domain (FHD). In some embodiments, the linker peptide region comprises SEQ ID NO:1 and/or SEQ ID NO: 2 or is encoded by a nucleic acid molecule comprising a nucleotide sequence comprising SEQ ID NO: 19 and/or 20.

As used herein, the term "non-ECM-binding fragment of Ang-1 protein" refers to any peptide sequence that comprises a peptide fragment from Ang-1 that cannot bind to the ECM or has reduced binding to the ECM. In some embodiments, a non-ECM binding fragment of Ang-1 comprises SEQ ID NOs: 5, 6, 7, 8, 9, and/or 10. In some embodiments, a non-ECM binding fragment of Ang-1 is encoded by a nucleic acid molecule comprising a nucleotide sequence comprising SEQ ID NOs: 23, 24, 25, 26, 27, or 28.

In some embodiments, a non-ECM binding fragment of Ang-1 protein refers to a protein that has a modification within an ECM-binding fragment or domain of Ang-1 protein. In some embodiments, the modification is a substitution, deletion, or insertion. In some embodiments the modification occurs within the ECM binding domains of Ang-1. In some embodiments, a non-ECM binding fragment of Ang-1 comprises a modification in a sequence comprising SEQ ID NOs: 1, 2, 3, and/or 4. In some embodiments, a non-ECM binding fragment of Ang-1 protein comprises a modification in a nucleotide sequence encoding a polypeptide comprising a sequence of SEQ ID NOs: 1, 2, 3, and/or 4. In some embodiments, the nucleotide sequence comprising the modification comprises SEQ ID NOs:19, 20, 21, and/or 22.

As used herein the term "ECM binding domain of Ang-1" refers to the sequences that bind to the ECM or are needed for the Ang-1 protein to bind to the ECM. In some embodiments, an ECM binding domain of Ang-1 comprises SEQ ID NOs: 1, 2, 3, or 4.

As used herein, the term "reduced" can refer the reduction of a value or activity of a protein, molecule, or compound, such as, for example, a protein binding to another protein or molecule. In some embodiments, the value or activity that is reduced is reduced completely or 100%. In some embodiments, the value or activity that is reduced is reduced by at least at least 5%, at least 10%, at least 20%, at least 30%, at least 40%, at least 50%, at least 60%, at least 70%, at least 80%, at least 90%, at least 95%, at least 96%, at least 97%, at least 98%, or at least 99%.

As used herein, "reduced binding to the ECM" refers to the ability of a protein to bind to the ECM when compared to the wild-type or fill-length version of the protein. In some embodiments, the reduction in binding to the ECM is at least 5%, at least 10%, at least 20%, at least 30%, at least 40%, at least 50%, at least 60%, at least 70%, at least 80%, at least 90%, at least 95%, at least 96%, at least 97%, at least 98%, at least 99%, or at least 100%. To determine how to determine if the binding of a protein is reduced is well known to one of ordinary skill in the art and can be determined using assays, such as, but not limited to, ELISA, western blot, immunopurification, immunofluorescence, antibody staining, and the like.

As used herein, a "fragment" of a protein is at least 5, at least 10, at least 20, at least 30, at least 40, at least 50, at least 75, at least 100, at least 200, at least 500, at least 1000 amino residues long.

As used herein, the term "a mutant Ang-1 which retain their angiogenesis promoting activity but which have reduced or inactive ECM binding" refers to any peptide sequence that comprises a peptide fragment from Ang-1 that cannot bind to the ECM or binds at a lower affinity than normal Ang-1 but which can still bind to Tie-2 as an agonist. In some embodiments the mutant Ang-1 which retains their angiogenesis promoting activity but which has reduced or inactive ECM binding is missing the linker domain of Ang-1. In some embodiments, the mutant Ang-1 is missing the N-terminal coiled-coil region. In some embodiments the mutant Ang-1 which retains their angiogenesis promoting activity but which has reduced or inactive ECM binding has substitutions and/or deletions and/or additions in the ECM anchor motif of Ang-1 protein. In some embodiments the mutant Ang-1 which retains their angiogenesis promoting activity but which has reduced or inactive ECM binding has substitutions and/or deletions and/or additions in the ECM anchor motif of Ang-1 protein wherein the cysteine at 265 is replaced with a serine. In some embodiments, the mutant may be a part of a fusion protein that comprises Ang-1 protein sequence and non-Ang-1 protein sequence. In some embodiments, "a mutant Ang-1 which retain their angiogenesis promoting activity but which have reduced or inactive ECM binding" comprises SEQ ID NOs: 5, 6, 7, 8, 9, and/or 10.

As used herein, the term "proteolytic resistant fragment of Ang-1 protein" refers to a Ang-1 protein that is resistant to cleavage or wherein the cleavage of Ang-1 is reduced. In some embodiments, the Ang-1 comprises a modification in a proteolytic domain of Ang-1, wherein the modification inhibits the proteolysis of Ang-1. In some embodiments, the proteolytic domain comprises SEQ ID NOs: 1 and/or 2. In some embodiments, a proteolytic resistant fragment of Ang-1 protein comprises a modification in a sequence comprising SEQ ID NO:1 and/or SEQ ID NO:2.

As used herein, the term "modification" refers to a protein or nucleic acid molecule substitution, insertion, or deletion. In the case of substitution, one amino acid residue or nucleobase is replaced by another. In the case of insertion, at least one amino acid residue or nucleobase is inserted into a protein or a nucleic acid molecule. In the case of deletion at least one amino acid residue or nucleobase is removed from a protein or a nucleic acid molecule. In some embodiments, at least 1, at least 2, at least 5, at least 10, at least 20, at least 30, at least 40, at least 50, at least 100, at least 500, at least 1000, or at least 2000 nucleobases are substituted, inserted, or deleted in a nucleic acid molecule. In some embodiments, at least 1, at least 2, at least 5, at least 10, at least 20, at least 30, at least 40, at least 50, at least 100, at least 200, at least 300, or at least 400 amino acid residues are substituted, inserted, or deleted in a protein or polypeptide.

As used herein, the term "a mutant Ang-1 which retain their angiogenesis promoting activity but which has is not cleaved into a antagonist fragment" refers to any peptide sequence that comprises a peptide fragment from Ang-1 that can still bind to Tie-2 as an agonist and has some deletion, addition or substitution to eliminate a protease cleavage site that when processed by a native protease yields an antagonist fragment. Ang-1 is normally cleaved within or nearby the linker peptide region to generate a C-terminal fragment, c-Ang-1, which has a similar molecular weight as that of the fibrinogen homology domain (FHD) fragment of Ang-1. Mutant Ang-1s which are engineered to eliminate the protease cleavage site are more effective as angiogenic substances in that they have a longer half life and do not produce an antagonist. In some embodiments a mutant Ang-1 which is engineered to eliminate the protease cleavage site comprises SEQ ID NOs: 5, 6, 9, and/or 10. In some embodiments, the mutant may be a part of a fusion protein that comprises Ang-1 protein sequence and non-Ang-1 protein sequence.

The c-Ang-1 doesn't bind to the ECM but binds to Tie-2-Fc fusion proteins. However, c-Ang-1 doesn't induce phosphorylation of Tie-2 on endothelial cells (HUVECs). Thus, c-Ang-1 may be used as a inhibitor of tumor angiogenesis to block tumor growth and metastasis. c-Ang-1 can inhibit the activation of Erk1/2 kinase. Thus, c-Ang-1 may also be used as an inhibitor of Erk1/2 kinase activity. In some embodiments the sequence of c-Ang-1 comprises SEQ ID NOs: 11 or 12 and can be encoded by a nucleotide sequence comprising SEQ ID NOs: 29 or 30.

As used herein, the term "phosphorylation inhibition fragment of Ang-1" refers to a fragment of Ang-1 that inhibits the phosphorylation of Erk1/2 or the activation of Erk1/2. In some embodiments, the phosphorylation inhibition fragment of Ang-1 comprises SEQ ID NOs: 11 or 12 or is an protein that comprises a polypeptide encoded by SEQ ID NOs: 29 or 30.

As used herein, the term "homologous peptide" refers to a peptide that has at least 50% similarity to the peptide being referred to. In some embodiments the peptide has at least 60%, at least 70%, at least 80%, at least 90%, at least 95%, at least 96%, at least 97%, at least 98%, at least 99%, or at least 100% to the peptide being referred to. In some embodiments the peptide has at least 60%, at least 70%, at least 80%, at least 90%, at least 95%, at least 96%, at least 97%, at least 98%, at least 99%, or at least 100% similarity to the ECM-binding fragment of Ang-1 protein and can bind to the ECM. In some embodiments the homologous peptide has at least 60%, at least 70%, at least 80%, at least 90%, at least 95%, at least 96%, at least 97%, at least 98%, at least 99%, or at least 100% similarity to SEQ ID NO:1, SEQ ID NO:2, SEQ ID NO:3, SEQ ID NO:4, SEQ ID NO:13, and/or SEQ ID NO:14. The homologous peptide may be isolated or incorporated into another protein so that a fusion protein is created. In some embodiments the peptide has at least 60%, at least 70%, at least 80%, at least 90%, at least 95%, at least 96%, at least 97%, at least 98%, at least 99%, or at least 100% similarity to the non-ECM-binding fragment of Ang-1 protein and can either not bind to the ECM or has reduced binding to the ECM. In some embodiments the homologous peptide has at least 60%, at least 70%, at least 80%, at least 90%, at least 95%, at least 96%, at least 97%, at least 98%, at least 99%, or at least 100% similarity to SEQ ID NO:5, SEQ ID NO:6, SEQ ID NO:7, SEQ ID NO:8, SEQ ID NO:9, and/or SEQ ID NO:10

According to some embodiments a homologous peptide refers to a peptide that has conservative substitutions. A conservative substitution is recognized in the art as a substitution of one amino acid for another amino acid that has similar properties. In some embodiments examples of conservative substitutions are those that are described in Table I.

TABLE I

| Amino Acid | Conservative Changes |
|---|---|
| Alanine (A) | Glycine (G), Serine (S) |
| Aspartic Acid (D) | Glutamic Acid (E) |
| Glutamic Acid (E) | Aspartic Acid (D) |
| Phenylalanine (F) | Tryptophan (W), Tyrosine (Y) |
| Glycine (G) | Alanine (A) |
| Histidine (H) | Tyrosine (Y) |
| Isoleucine (I) | Leucine (L), Methionine (M), Valine (V) |
| Lysine (K) | Arginine (R) |
| Leucine (L) | Isoleucine (1), Methionine (M) Valine (V) |
| Methionine (M) | Isoleucine (1), Leucine (L), Valine (V) |
| Asparagine (N) | Glutamine (Q) |
| Glutamine (Q) | Asparagine (N) |
| Arginine (R) | Lysine (K) |
| Serine (S) | Alanine (A), Threonine (T) |
| Threonine (T) | Serine (S) |
| Valine (V) | Isoleucine (I), Methionine (M) Valine (V) |
| Tryptophan (W) | Phenylalanine (F), Tyrosine (Y) |
| Tyrosine (Y) | Phenylalanine (F) Histidine (H) Tryptophan (W) |

As used herein, the phrase "homologous", "homologous peptide", "homologous peptide thereof" or variations thereof, refers to sequences characterized by a homology, at the nucleotide level or amino acid level, of at least a specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity.

Percent homology, similarity, or identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology between the probe and target is between about 50% to about 60%. In some embodiments, nucleic acids have nucleotides that are about 60%, preferably about 70%, more preferably about 80%, more preferably about 85%, more preferably about 90%, more preferably about 92%, more preferably about 94%, more preferably about 95%, more preferably about 97%, more preferably about 98%, more preferably about 99% and most preferably about 100% homologous to nucleotide sequences disclosed herein.

Homology may also be at the polypeptide level. In some embodiments, polypeptides are about 50%, about 60%, preferably about 70%, more preferably about 80%, more preferably about 85%, more preferably about 90%, more preferably about 92%, more preferably about 94%, more preferably about 95%, more preferably about 97%, more preferably about 98%, more preferably about 99% and most preferably about 100% homologous to the polypeptide sequences disclosed herein.

As used herein, the term "fusion protein" refers to a protein that comprises amino acids that are from at least two different proteins. As an example, a fusion protein may comprise the ECM-binding fragment of Ang-1 protein and kinase domain of another protein. This example would be considered a fusion protein. A fusion protein may also comprise a tag protein that may facilitate identification and/or purification. Examples of tag protein include, but are not limited, 6-Hisitidine Tag, HA-tag, GST-tag, v5 epitope, myc tag, and the like. The fusion of two protein sequences can be in any orientation. The tag protein can be placed at either the N-terminus or at the C-terminus of any fusion protein. In some embodiments, the tag protein is placed internally in the fusion protein. The ECM-binding fragment may be placed at the N-terminus of a fusion protein or at the C-terminus of a fusion protein. In some embodiments, the ECM-binding fragment of Ang-1 protein may be placed in the middle of a protein. In some embodiments, the "the ECM anchor motif" is combined with a biologically active protein which is desired to be retained locally as opposed to diffusing away for the site of administration. In some cases, the diffusion may cause side effects while in others, the desire for local retention is to maintain a high level of biologically active material at a site. In either case, the linker peptide region of Ang-1 or the N-terminal coiled-coil region that anchors Ang-1 to the ECM may be used as "the ECM anchor motif" to generate fusion proteins by fusing one or more of these regions to the intended proteins to make these proteins bound to the ECM and retained at sites of application. In some embodiments the "ECM anchor motif" comprises SEQ ID NOs: 1, 2, 3, and/or 4.

As used herein, the term "homologous peptide thereof" refers to a peptide that is a homologous peptide, as defined above, to the ECM-binding fragment of Ang-1 protein, non-ECM-binding fragment of Ang-1 protein, or to c-Ang-1. The homologous peptide thereof may be fusion protein, the entire Ang-1 protein, or a fragment thereof.

As used herein, the term "nucleotide sequence that encodes an ECM-binding fragment of Ang-1 protein" refers to a nucleotide sequence that when transcribed and translated would comprise an ECM-binding fragment of Ang-1 protein. According to some embodiments of the present invention, the nucleotide sequence may be the entire sequence of Ang-1. In some embodiments the nucleotide sequence may comprise a fragment of the nucleotide sequence of Ang-1. The nucleotide sequence of Ang-1 is well known to one of ordinary skill in the art. In some embodiments the nucleotide sequence that encodes an ECM-binding fragment of Ang-1 protein comprises SEQ ID NOs: 19, 20, 21, 22, 31, and/or 32.

As used herein, the term "nucleotide sequence that encodes a non-ECM-binding fragment of Ang-1 protein" refers to a nucleotide sequence that when transcribed and translated would comprise an non-ECM-binding fragment of Ang-1 protein. In some embodiments a nucleotide sequence that encodes a non-ECM-binding fragment of Ang-1 protein comprises SEQ ID NOs:23, 24, 25, 26, 27, and/or 28.

As used herein, the term "pharmaceutical composition" refers to compositions according to the invention including delivery components in combination with nucleic acid molecules and/or peptide molecules which further comprise a pharmaceutically acceptable carriers or vehicles, such as, for example, saline. Any medium may be used which allows for successful delivery of the peptide and/or nucleic acid. One skilled in the art would readily comprehend the multitude of pharmaceutically acceptable media that may be used in the present invention.

Pharmaceutical compositions may be formulated by one having ordinary skill in the art with compositions selected depending upon the chosen mode of administration. Suitable pharmaceutical carriers are described in Remington's Pharmaceutical Sciences, A. Osol, a standard reference text in this field, which is incorporated herein by reference.

The pharmaceutical compositions of the present invention may be administered by any means that enables the active agent to reach the agent's site of action in the body of an individual. Pharmaceutical compositions may be administered parenterally, i.e., intratumor, intravenous, subcutaneous, intramuscular. Intravenous and intratumor administration are preferred routes. Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

As used herein, the term "vector" refers to a delivery vehicle that is capable of delivering a nucleic acid to a cell. In some embodiments, the vector is a viral vector. In general, viral vectors may be DNA viruses such as recombinant adenoviruses and recombinant vaccinia viruses or RNA viruses such as recombinant retroviruses. Other recombinant vectors include recombinant prokaryotes that can infect cells and express recombinant genes. In addition to recombinant vectors, other vectors are also contemplated such as encapsulation in liposomes, lipofectin-mediated transfection, transferrin-mediated transfection and other receptor-mediated means. In some embodiments the vector is a DNA plasmid. The invention is intended to include such other forms of expression vectors and other suitable delivery means which serve equivalent functions and which become known in the art subsequently hereto.

Examples of recombinant adenoviral vectors include those which have the E1a region deleted and which carry a temperature-sensitive mutation in E2a (Engelhardt et al., Hum Gene Ther 5:1217-1229, 1994, which is incorporated herein by reference). Other examples of recombinant adenoviral vectors useful to deliver nucleic acid sequence of the present invention are described in U.S. Pat. Nos. 5,756,283 and 5,707, 618, which are each incorporated herein by reference.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

In another preferred embodiment of the present invention, nucleic acid is delivered through the use of lipofectin-mediated DNA transfer. LipofectAMINE™ liposome reagent (Life Technologies, Gaithersburg Md.) is a commercially available liposome encapsulation reagent which can be used for encapsulating cells following manufacturer's instructions. LipofectAMINE™ liposome reagent encapsulated nucleic acid molecules may be delivered to a host cell using liposome formulation administration methods.

In another preferred embodiment of the present invention, nucleic acid is delivered through the use of cationic lipid-mediated DNA transfer such as that which is described in U.S. Pat. No. 5,703,055, which is incorporated herein by reference.

In another preferred embodiment of the present invention, nucleic acid is delivered through the use of liposome-mediated DNA transfer such as that which is described in U.S. Pat. Nos. 4,235,871, 4,241,046 and 4,394,448, which are each incorporated herein by reference.

In some embodiments the compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and/or nucleotides of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

According to some embodiments of the present invention the pharmaceutical composition is administered in an amount that is therapeutically effective. As used herein, the term "therapeutically effective" refers to an amount effective to achieve the intended purpose. In some embodiments the intended purpose is to treat coronary artery disease, vascular disease, a condition involving ischemia, cancer, diabetes or arthritis. In some embodiments the intended purpose is to effectively promote angiogenesis in the patients with the diseases related to lack of blood vessels such as ischemia in hearts and limbs. In some embodiments the intended purpose is to reduce stroke, heart attack, blood vessel blockage, hemorrhage, artherosclerosis risk by maintain the health and integrity of blood vessels (by reduce the loss the endothelial monolayer integrity and attachment of blood cells on vessel walls). In some embodiments the intended purpose is to assist the recovery of the patients who had stroke and the angioplasty procedure by promoting the growth/survival of endothelial cells and establish endothelial monolayer and inhibit excessive inflammation, hemorrhage, and proliferation of vascular smooth muscle. In some embodiments the intended purpose is to treat patients with restenosis by inhibiting reclosure of blood vessel after inserting stents into blood vessels. In some embodiments the intended purpose is to make stable and functional artificial blood vessels. In some embodiments a therapeutically effective amount refers to an amount effective to ameliorate or prevent the symptoms, or prolong the survival of, the patient being treated. Therapeutically effective amounts are typically determined by the effect they have compared to the effect observed when a composition which includes no active ingredient is administered to a similarly situated individual The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician. Determination of a therapeutically effective amount is well within the capabilities of those skilled in the art, especially in light of the detailed disclosure provided herein.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

According to some embodiments, the present invention provides for methods of promoting angiogenesis, endothelial survival, and/or maintaining vascular integrity As used herein, the term "angiogenesis" refers to the growth of blood vessels. In some embodiments the promotion of angiogenesis promotes the growth of new blood vessels, while in some embodiments existing blood vessels are promoted to grow. Angiogenesis is a term well understood by those of ordinary skill in the art. In some embodiments endothelial survival refers to the process of preventing endothelial cells from dying. In some embodiments endothelial survival refers to the promoting the growth of endothelial cells.

In some embodiments "maintaining vascular integrity" refers to the process by which the a vascular system viability and functions are kept at specific level. In some embodiments the vascular system may be located throughout the individual. In some embodiments the vascular system may be localized to a specific region of the individual. For example, if a person has a poor vascular system in the foot, the pharmaceutical composition may be administered in a therapeutically effective amount to promote and maintain vascular integrity in that foot, while the rest of the vascular system may be unaffected. However, in other embodiments a therapeutically effective amount may promote angiogenesis, endothelial survival, and maintaining vascular integrity throughout the individual.

According to some embodiments, the present invention provides for methods for identifying compounds that modulates the binding of Ang-1 to ECM comprising performing a test assay that comprises the steps of contacting a protein that comprises at least an ECM-binding fragment of Ang-1 protein that comprises SEQ ID NO:1, SEQ ID NO:2, SEQ ID NO:3 and/or SEQ ID NO:4 or a homologous peptide thereof with ECM material in the presence of a test compound and measuring the level of binding of the protein that comprises at least an ECM binding fragment of Ang-1 protein that comprise SEQ ID NO:1, SEQ ID NO:2, SEQ ID NO:3 and/or SEQ ID NO:4 or a homologous peptide thereof with the ECM. In some embodiments the method further comprises comparing the level with the level of binding of the protein that comprises at least an ECM-binding fragment of Ang-1 protein that comprises SEQ ID NO:1, SEQ ID NO:2, SEQ ID NO:3 and/or SEQ ID NO:4 or a homologous peptide thereof with ECM material in the absence of said test compound. In some embodiments when the level of binding of the protein that comprises at least an ECM-binding fragment of Ang-1 protein that comprises SEQ ID NO:1, SEQ ID NO:2, SEQ ID NO:3 and/or SEQ ID NO:4 or a homologous peptide thereof with the ECM in the presence of the test compound is less than the level of binding of the protein that comprises at least an ECM-binding fragment of Ang-1 protein that comprises SEQ ID NO:1, SEQ ID NO:2, SEQ ID NO:3 and/or SEQ ID NO:4 or a homologous peptide thereof with the ECM in the absence of the test compound results indicate that the test compound modulates binding of Ang-1 to ECM by inhibiting the binding.

In some embodiments when the level of binding of the protein that comprises at least an ECM-binding fragment of Ang-1 protein that comprises SEQ ID NO:1, SEQ ID NO:2, SEQ ID NO:3 and/or SEQ ID NO:4 with the ECM in the presence of the test compound is more than the level of binding of the protein that comprises at least an ECM-binding fragment of Ang-1 protein that comprises SEQ ID NO:1, SEQ ID NO:2, SEQ ID NO:3 and/or SEQ ID NO:4 with the ECM in the absence of the test compound results indicate that the test compound modulates binding of Ang-1 to ECM by enhancing the binding.

As used herein, the term "modulates" refers to an increase or a decrease. In some embodiments, the modulation is at least 10%, at least 20%, at least 30%, at least 40%, at least 50%, at least 60%, at least 70%, at least 80%, at least 90%, at least 95%, or at least 100% In some embodiments the test compound increases the level of Ang-1 protein binding to the ECM. In some embodiments the test compound decreases the level of Ang-1 protein binding to the ECM. In some embodiments, the compound is a peptide. In some embodiments, the peptide comprises a fragment of SEQ ID NO:1, SEQ ID NO:2, SEQ ID NO:3 and/or SEQ ID NO:4. In some embodiments the peptide is comprises about 2, about 3, about 4, about 5, about 6, about 7, about 8, about 9, about 10, about 11, about 12, about 13, about 14, about 15, about 5-15, at 20, at least 30, at least 40, at least 45 amino acid residues.

As used herein, the term "at least an ECM-binding fragment of Ang-1 protein" refers to a protein that comprises a fragment of Ang-1 that can bind to ECM. In some embodiments this refers to SEQ ID NO:1, SEQ ID NO:2, SEQ ID NO:3 and/or SEQ ID NO:4. In some embodiments, this refers to protein that comprises a section of the protein that is homologous to an ECM-binding fragment of Ang-1 protein. In some embodiments, the protein can be the full-length Ang-1 protein or a fragment thereof. In some embodiments the "at least an ECM-binding fragment of Ang-1 protein" comprises SEQ ID NOs:1, 2, 3, 4, 13, and/or 14. In some embodiments, the protein can be a fusion protein that comprises Ang-1 protein sequence and non-Ang-1 protein sequence. In some embodiments, a protein comprising at least an ECM-binding fragment of Ang-1 protein comprises a peptide sequence that has at least 50%, at least 60%, at least 70%, at least 80%, at least 90%, at least 95%, at least 96%, at least 97%, at least 98%, at least 99%, at least 100% similarity to an ECM-binding fragment of Ang-1. In some embodiments a protein comprising at least an ECM-binding fragment of Ang-1 protein comprises a peptide sequence that has at least 50%, at least 60%, at least 70%, at least 80%, at least 90%, at least 95%, at least 96%, at least 97%, at least 98%, or at least 100% similarity to SEQ ID NOs:1, 2, 3, 4, 13, and/or 14. In some embodiments a protein comprising at least an ECM-binding fragment of Ang-1 protein comprises a peptide sequence that has at least 50%, at least 60%, at least 70%, at least 80%, at least 90%, at least 95%, at least 96%, at least 97%, at least 98%, at least 99%, or at least 100% similarity to SEQ ID NOs:1, 2, 3, and/or 4.

According to some embodiments "ECM material" refers to a compound or material that is found in the extracellular matrix that can bind to an ECM-binding fragment of Ang-1 protein. According to some embodiments the "ECM material" refers to a composition comprising fibronection, laminin, type I collagen, type IV collagen, vitronectin, fibrinogen, matrigel, LLC carcinoma ECM, BSA, heparin, chondroitin sulfate, or hyaluronic acid.

In some embodiments the ECM material is produced by culturing cells on a substrate for a sufficient time for the cells to produce the ECM material on the substrate and then removing the cells from the substrate without removing the ECM material. In some embodiments the cells that are used to produce the ECM material are Lewis Lung carcinoma cells or TA3 murine mammary carcinoma cells. As used herein, the term "substrate" refers to any vessel or container that is capable of culturing cells. Examples of substrates include, but are not limited to, petri dishes, 6-well plates, 96-well plates, 384-well plates, and the like. Removing cells from the substrate without removing the ECM material is well within the skill of one of ordinary skill in the art. An example of how to remove the cells without removing the ECM includes contacting the cells with a chelator such as EDTA or EGTA for a sufficient time to remove the cells without effecting the ECM material. There are other methods that can performed the same function as contacting the cells with EDTA or EGTA and are within the scope of the current invention.

According to some embodiments the protein that comprises at least an ECM-binding fragment of Ang-1 comprising a detectable label. As used herein, the term "detectable label" refers to any molecule that can be detected with methods that are well known to those of ordinary skill in the art. Molecules with detectable labels include without limitation proteins, protein fragments, antibodies, fluorescent labels, radioactive labels, chromophores, chemilluminescent probes, and the like. In some embodiments the detectable label is used to measure the level of binding of the protein that comprises at least an ECM-binding fragment of Ang-1 protein on the ECM.

In some embodiments the method of identifying compound that modulates the binding of Ang-1 to ECM further comprises multiple test assays that are identical except that the amount of the test compound used differs. To aid in determining the effective amount of a test agent multiple assays are preformed using different amounts of the test compound. In some embodiments at least 2 assays are performed. In some other embodiments at least 3, at least 4, at least 5, at least 6, at least 7, at least 8, at least 9, at least 10, at least 15, at least 20, least 40, at least 50, at least 100 assays are performed using different amounts of the test compound.

According to some embodiments the methods of identifying a compound that modulates the binding of Ang-1 to ECM further comprises determining the level of binding of a protein that comprises at least an ECM-binding fragment of Ang-1 protein that comprises SEQ ID NO:1, SEQ ID NO:2, SEQ ID NO:3 and/or SEQ ID NO:4 with ECM material in the absence of the test compound by performing a control assay wherein the control assay comprises the steps of contacting a protein that comprises at least an ECM-binding fragment of Ang-1 protein that comprises SEQ ID NO:1, SEQ ID NO:2, SEQ ID NO:3 and/or SEQ ID NO:4 with ECM material in the absence of a test compound and measuring the level of binding of the protein that comprises at least an ECM binding fragment of Ang-1 protein that comprises SEQ ID NO:1, SEQ ID NO:2, SEQ ID NO:3 and/or SEQ ID NO:4 with the ECM.

Assays that can be used for the methods to identify compounds that modulates the binding of Ang-1 to ECM are well known to those of ordinary skill in the art and require only routine experimentation. Examples of assays that are well known to those of ordinary skill in the art include ELISA, Sandwich Assays, flow cytometry, immunoprecipitation, and the like.

According to some embodiments the present invention provides for pharmaceutical compositions comprising a pharmaceutically acceptable carrier and a therapeutically effective amount of Ang-2 protein and/or a vector comprising a nucleic acid molecule that comprises the nucleotide coding sequence of Ang-2. According to some embodiments the present invention provides for pharmaceutical compositions comprising a pharmaceutically acceptable carrier and a therapeutically effective amount of Ang-3 protein and/or a vector comprising a nucleic acid molecule that comprises the nucleotide coding sequence of Ang-3

As used herein, the term "Ang-2" refers to the protein or nucleic acid encoding the protein or fragment thereof of Angiopoietin-2. In some embodiments the Ang-2 is mammalian Ang-2. In some embodiments, the Ang-2 is human, mouse, rat, dog, cat, pig, or horse. In some embodiments the Ang-2 protein comprises SEQ ID NO:15 and/or SEQ ID NO:16. In some embodiments the Ang-2 nucleotide coding sequence comprises SEQ ID NO 33 and/or SEQ ID NO:34. In some embodiments, the Ang-2 protein or the nucleic acid that encodes Ang-2 is a fragment of the Ang-2 protein or the nucleotide coding sequence of Ang-2. In some embodiments the Ang-2 protein comprises a fragment of SEQ ID NO:15 and/or SEQ ID NO:16. In some embodiments, "Ang-2" refers to a fusion protein comprising non-Ang-2 protein sequence and Ang-2 protein sequence. According to some embodiments, "Ang-2" refers to a protein that has at least 50%, at least 60%, at least 70%, at least 80%, at least 90%, at least 95%, at least 96%, at least 97%, at least 98%, at least 99%, at least 100% similarity to SEQ ID NO:15 and/or SEQ ID NO:16. In some embodiments the nucleotide coding sequence comprises a nucleotide coding sequence that is at least 50%, at least 60%, at least 70%, at least 80%, at least 90%, at least 95%, at least 96%, at least 97%, at least 98%, at least 99%, at least 100% identical to SEQ ID NO:33 and/or SEQ ID NO:34.

As used herein, the term "Ang-3" refers to the protein or nucleic acid encoding the protein or fragment thereof of Angiopoietin-3. In some embodiments the Ang-3 is mammalian Ang-3. In some embodiments, the Ang-3 is human, mouse, rat, dog, cat, pig, or horse. In some embodiments the Ang-3 protein comprises SEQ ID NO:17 and/or SEQ ID NO:18. In some embodiments the Ang-3 nucleotide coding sequence comprises SEQ ID NO: 35 and/or SEQ ID NO: 36. In some embodiments, the Ang-3 protein or the nucleic acid that encodes Ang-3 is a fragment of the Ang-3 protein or the nucleotide coding sequence of Ang-3. In some embodiments the Ang-3 protein comprises a fragment of SEQ ID NO: 17 and/or SEQ ID NO: 18. In some embodiments, "Ang-3" refers to a fusion protein comprising non-Ang-3 protein sequence and Ang-3 protein sequence. According to some embodiments, "Ang-3" refers to a protein that has at least 50%, at least 60%, at least 70%, at least 80%, at least 90%, at least 95%, at least 96%, at least 97%, at least 98%, at least 99%, at least 100% similarity to SEQ ID NO: 17 and/or SEQ ID NO: 18. In some embodiments the nucleotide coding sequence comprises a nucleotide coding sequence that is at least 50%, at least 60%, at least 70%, at least 80%, at least 90%, at least 95%, at least 96%, at least 97%, at least 98%, at least 99%, at least 100% identical to SEQ ID NO 35 and/or SEQ ID NO: 36.

According to some embodiments the present invention provides for methods of treating an individual, or an individual in need thereof, suspected of having cancer comprising the step of administering to the individual a pharmaceutical composition comprising a pharmaceutically acceptable carrier and a therapeutically effective amount of c-Ang-1 protein, and/or Ang-2 protein, and/or Ang-3 protein and/or a vector comprising a nucleic acid molecule that comprises the nucleotide coding sequence of c-Ang-1, and/or a vector comprising a nucleic acid molecule that comprises the nucleotide coding sequence of Ang-2, and/or a vector comprising a nucleic acid molecule that comprises the nucleotide coding sequence of Ang-3. According to some embodiments the present invention provides for methods of treating an individual, or an individual in need thereof, suspected of having cancer comprising the step of administering to the individual a pharmaceutical composition comprising a pharmaceutically acceptable carrier and a therapeutically effective amount of Ang-3 protein and/or vector comprising a nucleic acid molecule that comprises the nucleotide coding sequence of Ang-3 protein. The methods of administration are defined above as well as what is meant by a therapeutically effective amount. In some embodiments, a c-Ang-1 protein comprises SEQ ID NO: 11 and/or SEQ ID NO: 12. In some embodiments a vector comprising a nucleic acid molecule that comprises the coding sequence of c-Ang-1 comprises SEQ ID NO: 29 and/or SEQ ID NO:30.

The cancers that can be treated are not limited to any cancer described herein and can include cancers of the bladder, cancers of the brain, cancers of the breast, cancers of the colon, hodgkin's disease, cancers of the kidney, cancers of the lung, melanoma, non-hodgkin's lymphoma, oral cancer, ovarian cancer, prostate cancer, uterine/cervical cancer, leukemia, cancers of the pancreas, testicular cancer, solid tumors, and the like. In some preferred embodiments, the method is performed in conjunction with the removal or elimination of a primary tumor. Such methods prevent micrometastasis from becoming macromaetastatic disease.

According to some embodiments the present invention provides for methods of preventing an individual arthritis and/or diabetes, particular one who is suspected of being at an elevated risk of developing either. The methods comprise the step of administering to the individual a pharmaceutical composition comprising a pharmaceutically acceptable carrier and a therapeutically effective amount of c-Ang-1 protein, and/or Ang-2 protein, and/or Ang-3 protein and/or a vector comprising a nucleic acid molecule that comprises the nucleotide coding sequence of c-Ang-1 and/or a vector comprising a nucleic acid molecule that comprises the nucleotide coding sequence of Ang-2, and/or a vector comprising a nucleic acid molecule that comprises the nucleotide coding sequence of Ang-3. In some embodiments the pharmaceutical composition comprises a therapeutically effective amount of Ang-3 and/or a vector comprising a nucleic acid molecule that comprises the nucleotide coding sequence of Ang-3.

In some embodiments, pharmaceutical compositions comprising a therapeutically effective amount of c-Ang-1, Ang-2, and/or Ang-3 are administered after the removal of the primary tumor. In some embodiments, pharmaceutical compositions comprising a therapeutically effective amount of c-Ang-1, Ang-2, and/or Ang-3 are administered to prevent, reduce, or treat metastasis of a cancer and/or tumor.

The methods of administration are defined above as well as what is meant by a therapeutically effective amount.

EXAMPLES

Example 1

Unlike Angiopoietin-2 (Ang-2), which is primarily secreted, Angiopoietin-1 (Ang-1) binds to the extracellular matrix (ECM) via its linker peptide region (26 amino acid long). Furthermore the binding of Ang-1 to the ECM blocks the binding between Ang-1 and its receptor, Tie-2 receptor tyrosine kinase. The ECM binding of Ang-1 negatively regulates the availability and the pro-angiogenesis activity of Ang-1.

Two Ang-I mutants have been established in which either the linker peptide region of Ang-I ($_{258}$VHNLVSL$_{265}$CTKEGVLLKGGKREEBKPF$_{283}$) (SEQ ID NO. 37) was deleted (Ang-1$_{minuslinker}$) or the Cys265 residue in the region was mutated to Ser (Ang-1$_{cys265ser}$).

Ang-1$_{minuslinker}$ and to a less extent Ang-1$_{cys265ser}$ displayed dramatically reduced binding to the ECM and altered aggregation pattern. Thus, it is expected they display higher pro-angiogenic activity.

When expressed by tumor cells, Lewis lung carcinoma (LLC) cells, Ang-1$_{minuslinker}$ and to a less extent Ang-1$_{cys265ser}$ promotes spontaneous pulmonary metastasis much more efficiently than the wild type Ang-1 by promoting tumor angiogenesis and transformation of micrometastases to life-threatening macrometastases. This result supports the hypothesis that the ECM binding negatively regulates the pro-angiogenic activity of Ang-1.

We discovered for the first time that Ang-1 is cleaved within or nearby the linker peptide region to generate a C-terminal fragment, c-Ang-1, which has a similar molecular weight as that of the fibrinogen homology domain (FHD) fragment of Ang-1.

c-Ang-1 doesn't bind to the ECM but binds to Tie-2-Fc fusion proteins. However, c-Ang-1 doesn't induce phosphorylation of Tie-2 on endothelial cells (HUVECs), indicating strongly that c-Ang-1 acts as a dominant regulator of full-length Ang-1 and may be used as a inhibitor of tumor angiogenesis to block tumor growth and metastasis in the future.

It was found that Ang-1$_{minuslinker}$, in which the linker peptide region was deleted, resists the cleavage that occurs in the wild type Ang-1, whereas Ang-1$_{cys265ser}$ behaves similar to the wild type Ang-1 and is cleaved to generate a similar C-terminal fragment. This finding has a tremendous potential important. According to this result, wild type human Ang-1 and hAng-1$_{cys265ser}$ are likely sensitive to the cleavage, which will occur in vivo, if human Ang-1 and hAng-1$_{cys265ser}$ proteins were used for any clinical trails. This means that human Ang-1 and hAng-1cys265ser proteins may not be as effective as the cleavage resistant version of Ang-1, Ang-1$_{minuslinker}$. Ang-1$_{minuslinker}$ will not only not bind to the ECM, but also be resistant to cleavage. The spontaneous tumor metastasis results support this conclusion.

To confirm that Ang-2 is secreted and Ang-1 binds to the ECM in vivo, the in vivo distribution of Ang-1 and Ang-2 proteins was analyzed by growing subcutaneous solid tumors derived from LLC cells expressing v5-epitope tagged Ang-1 or Ang-2. The results demonstrated that Ang-2 but not Ang-1 is detected in the serum samples of the experiment mice. In addition, Ang-2 proteins were extracted by PBS buffer from the solid tumors, while Ang-1 proteins can only be extracted by 2M urea buffer. These results indicated that Ang-1 is bound to the ECM in vivo and retained to promote angiogenesis only in local environment where it is produced; whereas Ang-2 can diffuse away from it production site to keep its local concentration low and meanwhile inhibit angiogenesis at distant metastatic sites in vivo.

Overexpression of Ang-2 blocks spontaneous pulmonary metastasis of LLC cells. Coupled with the results described herein the ECM-binding of Ang-1 is an essential mechanism to establish and maintain the activity ratio between Ang-1 and Ang-2 at local and distant sites, which plays important role in regulating dormancy of micrometastases. Release Ang-1 from the ECM may be an effective mechanism to switch dormant micrometastases to macrometastases.

A peptide, L$_{265}$CTKEGVLLKGGKREEEKPF$_{283}$ (SEQ ID NO. 38), derived from the linker peptide region was found to inhibit the incorporation of Ang-1 proteins to the ECM in cell culture condition. This result suggests that the linker peptide or its derivatives (peptides and small molecules) can potentially be used to modulate the ECM binding of Ang-1, therefore the bioactivity and availability of Ang-1.

Because of high sequence homology between human and mouse Ang-1. All the results obtained using mouse Ang-1 should apply to human Ang-1 as well. Indeed, we have found that human Ang-2 is secreted and human Ang-1 is bound to the ECM just like their mouse counterparts. This should be true for the in vivo results we obtained using mouse Ang-2.

Two Ang-1 mutants (in the forms of proteins and gene therapy), Ang-1$_{minuslinker}$ and Ang-1$_{cys265ser}$, which were established based on their reduced binding to the ECM, displayed increased activity in promoting spontaneous pulmonary metastasis of a subline of Lewis lung carcinoma cell by promoting tumor angiogenesis and transformation of micrometastases to macrometastases, may be used in effectively promoting angiogenesis in following areas:

To effectively promote angiogenesis in the patients with the diseases related to lack of blood vessels such as ischemia in hearts and limbs.

To reduce stroke, heart attack, blood vessel blockage, hemorrhage, artherosclerosis risk by maintain the health and integrity of blood vessels (by reduce the loss the endothelial monolayer integrity and attachment of blood cells on vessel walls).

To assist the recovery of the patients who had stroke and the angioplasty procedure by promoting the growth/survival of endothelial cells and establish endothelial monolayer and inhibit excessive inflammation, hemorrhage, and proliferation of vascular smooth muscle.

To treat patients with restenosis by inhibiting re-closure of blood vessel after inserting stents into blood vessels.

To make stable and functional artificial blood vessels.

The peptides derived from the linker peptide region and small molecular derivatives that can reduce the binding of Ang-1 to the ECM may be used to activate the ECM-bound Ang-1 in vivo using in the areas as described above.

Many clinical trails have reported problem in retaining their test proteins at the intended sites due to diffusion of their proteins. The linker peptide region of Ang-1 anchors Ang-1 to the ECM. So, it may be used as "the ECM anchor motif" to generate fusion proteins by fusing the linker peptide region to the intended proteins to make these proteins bound to the ECM and retained at sites of application.

A screening system has been established that can be used to identify the small molecules that are capable of blocking Ang-1 and the ECM interaction.

Using Ang-2 and c-Ang-1 (proteins and expression vectors in gene therapy) to block tumor metastasis, especially after surgically removal of the primary tumors.

It was observed that some primary tumors inhibit the development of metastasis, including LLC cells. The factors generated by local primary tumors and involved in establishing and maintaining dormancy of micrometastases likely have one of the following characteristics. First, a pair of agonist/antagonist on angiogenesis (or two factors have opposite functions) has different ECM- or cell-binding capacity. Thus, the pro-angiogenic agonist binds to the ECM or cells, therefore retains in the local environment; whereas the anti-angiogenic antagonist can diffuse away to keep its local concentration low and meanwhile inhibit angiogenesis at distant metastatic sites. Second, the full-length factor and its cleavage product display opposite functions on angiogenesis and different capacity to bind to the ECM- or cells; so that the pro-angiogenic activity of the full-length factor retains at local site and the anti-angiogenic cleavage fragment can diffuse to inhibit angiogenesis at distant metastatic sites. Ang-2 fits the first characteristics, and c-Ang-1 fits the second characteristics.

Thus, both Ang-2 and c-Ang-1 or in the combination of both have strong potential to be used to effectively block angiogenesis occurred not only in tumor growth and metastasis but also in other pathologic situations.

Ang-2 and c-Ang-1 (proteins and gene therapy) can also be used to inhibit arthritis and diabetes.

The serum concentration of Ang-2 and c-Ang-1 may be used as an indicator for the need for post surgery use of Ang-2 and/or c-Ang-1 to inhibit progression of metastasis by blocking the transformation of micrometastases to life-threatening macrometastases.

The serum concentration of Ang-1 may be used as an important diagnosis and prognosis marker for aggressive malignant cancers.

Example 2

Blood vessels form via two distinct processes, vasculogenesis and angiogenesis. Vasculogenesis is establishment of a primitive vascular network by a de novo formation of endothelial cells from their precursors. In contrast, angiogenesis is the formation of new blood vessels by sprouting from pre-existing ones. Angiogenesis plays important roles in embryonic organogenesis and postnatal tissue repair, female reproductive function, arthritis, diabetes, tumor growth and metastasis (1, 2, 3, 4, 5, 6, 7, 8, 9). Angiogenesis is a complex multistep process, which includes dynamic changes of cell-cell and cell-matrix adhesion, degradation of the extracellular matrix (ECM), endothelial cell proliferation, migration, differentiation into tubular structure, recruitment of the perivascular supporting cells, and the maturation process (4, 10, 11, 12, 13). Numerous molecules are involved in these processes, including many pro- and anti-angiogenic factors (4, 7, 8, 10, 12) and their receptors, proteases, adhesion and ECM receptors, and the ECM components. Vascular endothelial growth factors (VEGFs) and angiopoietins play especially important roles in angiogenesis) due to the primarily restricted expression of their receptors on endothelial cells (ECs, reviews see 4, 7, 8, 10, 11, 12).

Angiopoietin-1-Tie-2 Pathway is Indispensable and Essential for Embryonic Angiogenesis Tie-2 is a member of the Tie (tyrosine kinase with immunoglobulin and epidermal growth factor homology domains) family of receptor tyrosine kinases that consists of two members, Tie-I and Tie-2. Tie-2 is expressed in endothelial cells and their precursors, as well as some hematopoietic cell lineages (20, 21, 22, 24, 25, 26), and is required for embryonic vascular development (23, 25, 26, 27). There are three Tie-2 ligands identified so far (18, 19, 55), Angiopoietin-1, -2, and -3/4(Ang-1, Ang-2, and Ang-3/4), which bind to their receptors with similar affinity and are approximate 80 kilodalton (kDa) in molecular weight. Ang-3 and Ang-4 are orthologs between mouse and human (55). Angiopoietins have a similar protein structure, which consists of a signal peptide, an amino terminal coiled-coil domain, a short linker peptide region, and a carboxyl terminal fibrinogen homology domain (FHD, 18, 19, 55). The coiled-coil region is responsible for dimerization/mulimerization of angiopoietins, whereas the FHD binds to Tie-2 receptor (19, 30, 55). All three angiopoietins form dimers and oligomers (18, 19, 30, 31, 32).

Studies of the knockout mice indicated that VEGFs and Ang-1 play critical and distinct roles in different aspects and at different stages of vascular development. VEGFs play an essential role in early vascular development to establish the initial vascular plexus (14, 17, 33, 57, 58). Targeted disruption of Ang-1 or Tie-2 gene, or overexpression of Ang-2 resulted in embryonic death with similar vascular defects (19, 23, 27, 34), suggesting that Ang-1 is an agonist, whereas Ang-2 is an antagonist of Tie-2. These knockout and transgenic mice displayed normal VEGF-dependent early vascular development; however, they have profound defects in the later stages of vascular development, which are the remodeling, organization, and stabilization of the primitive vasculature (23, 27, 34, 35).

On the contrary to Ang-1 knockout mouse, Ang-2 knockout mouse displayed normal embryonic angiogenesis but with a lymphatic drainage problem due to disorganization and hypoplasia of the intestinal and dermal lymphatic capillaries. In addition, the hyaloid vasculature in eyes fails to regress and their retinal blood vessels fail to sprout in these Ang-2 knockout mice. These results indicated that Ang-2 plays a role in postnatal vessel remodeling and angiogenesis (84).

Ang-2 is a Naturally Occurring Antagonist of Tie-2

Many studies have shown that Ang-2 is a naturally occurring antagonist of Tie-2 (19, 30, 31, 55, 71, 85). Ang-1 activates Tie-2 receptors by inducing tyrosine phosphorylation of Tie-2 and promotes recruitment of pericytes and smooth muscle cells to neovessels, which are important for establishing and maintaining vascular integrity. Ang-1 and -2 bind to the same domain in Tie-2 receptor (86), and Ang-2 competes with Ang-1 for the binding of Tie-2 and blocks Tie-2 phosphorylation induced by Ang-1 (19). It is unclear whether Ang-2 merely blocks the binding of Ang-1 and Tie-2, or induces different unidentified signals or binds to and activates other receptor(s) as well. Limited publications have shown that under certain conditions, Ang-2 can induce Tie-2 phosphorylation (69, 86). So far, the evidences support that Ang-2 is a context dependent antagonist of Tie-2 (84).

It is well established that angiogenesis is regulated by the precise balance between pro- and anti-angiogenic factors (4, 7, 8). The existence of a pair of agonist and antagonist ligands for the same receptor underscores the importance of the precise regulation of Tie-2 activity for adequate endothelial function and angiogenesis. The transgenic mice overexpressing Ang-1 displayed increased vascularization and reduced vasculature leakage (36, 37, 38), which demonstrated once again that Ang-1 plays an important role in the formation of blood vessels and establishment of vascular integrity by recruiting and maintaining peri-endothelial support cells.

The Signal Transduction Pathways Activated by Angiopoietins

Several studies have provided possible mechanisms for the pro-angiogenic role of Ang-1. Unlike other angiogenic factors such as VEGF and bFGF, Ang-1 is not an endothelial mitogen. However, Ang-1 promotes adhesion and migration of endothelial cells (40, 41), inhibits endothelial cell apoptosis via PI-3 kinase/Akt pathway (42, 43, 44, 72, 78, 92) by inhibition of Smac release from mitochondria and up-regulation of Survivin proteins (124). In addition, Ang-1 induces endothelial cell sprouting via activation of focal adhesion kinase (FAK, 45, 46, 54). On the other hand, studies have shown that Ang-2 destabilizes vasculature and either initiates angiogenesis in the presence of pro-angiogenic factors, such as VEGFs, which supply endothelial cells with the necessary survival and proliferation signals (31, 47, 48, 49); or induces apoptosis of endothelial cells in the absence of pro-angiogenic factors (47, 50). Furthermore, both Ang-1 and Ang-2 can act synergistically with VEGF by enhancing VEGF-induced angiogenesis (19, 45, 49, 73). Thus, angiogenesis is likely dependent on the cooperative and complement effects of VEGF and angiopoietins (74).

Unlike Ang-2, Ang-1 Binds to the ECM which Regulates its Availability and Activity Ang-2 is wildly expressed by many tumor cells (31, 39), and its expression is often induced in the endothelia undergoing active remodeling or regression and by hypoxia and growth factors, including VEGF (19, 39, 48, 51, 52, 53); whereas Ang-1 is widely expressed primarily by mesenchymal cells in adult tissues (19, 75). Unlike that of Ang-2, little is known about how Ang-1 expression is regulated. Our recent finding offered a possible mechanism that may regulate the availability and activity of Ang-1 proteins.

To study the roles of angiopoietins in tumor growth and metastasis, LLC and TA3 murine mammary carcinoma (TA3) transfectants expressing the C-terminal v5 epitope tagged Ang-1 and Ang-2 were established (31, 32). We found that unlike Ang-2, which is primarily secreted, Ang-1 is secreted and incorporated into the ECM via its linker peptide region. Furthermore, the ECM binding of Ang-1 blocks the Ang-1-Tie-2 interaction (32) and the dissemination of Ang-1 from its production sites (FIG. 1B). The results suggest that the availability and activity of Ang-1 might be negatively regulated by its binding to the ECM. The strong ECM binding of Ang-1 ensures that Ang-1 is restricted to the local environment where it is produced, whereas Ang-2 can disseminate from its production site (FIG. 1B) and affect angiogenesis at distant metastatic sites. The difference in the ECM binding of Ang-1 and Ang-2 may be important in establishing and maintaining dormancy of micrometastases.

The Roles of Angiopoietins in Tumor Angiogenesis are not Well Established

Tumor angiogenesis, formation of the neovessels in primary and metastatic tumors, is essential for tumor growth and metastasis (1, 2, 3, 7, 9, 10, 56, 59, 60, 61, 66, 67, 93, 94, 76). Neovessels not only supply necessary nutrients and oxygen to primary and metastatic tumors, but also provide important routes for primary tumor cells to metastasize (2, 3, 9, 77, 79), which is the major cause of cancer related mortality. Previous studied have shown that blockade of the Tie-2 pathway by dominant negative soluble Tie-2 inhibits tumor angiogenesis, growth and metastasis (28, 29), Recent evidence indicated that Ang-1 and Ang-2 are expressed by tumor cells (31, 39) and involved in tumor angiogenesis (31, 62, 63, 64, 65, 80, 81). These results obtained from different in vivo tumor models were in conflict and showed that Ang-1 and Ang-2 either promote or inhibit tumor angiogenesis. These discrepancies are not clearly understood and may reflect the fact that different tumor models were used, which clearly have different background activity of the multiple interactive angiogenic pathways and other related signal transduction pathways.

It has been shown recently that overexpression of Ang-2, but not Ang-1, inhibits growth and metastasis of LLC and TA3 carcinoma cells by disruption of tumor angiogenesis (31). The tumors overexpressing Ang-2 exhibited aberrant and incomplete angiogenesis in vivo, characterized by the formation of disorganized endothelial cell aggregates without the associated smooth muscle cells, and by massive apoptosis of the endothelial cells and surrounding tumor cells (31). This result is consistent with the hypothesis that Ang-2 inhibits the Ang-1-dependent recruitment of periendothelial smooth muscle cells.

Significance

There is an increasing body of evidence that inhibition of tumor angiogenesis is a potentially effective and novel therapeutic strategy to slow down and block tumor growth and metastasis (82, 83, 87, 88, 89, 90, 91, 97, 98). However, since tumor angiogenesis is regulated by multiple factors secreted by tumor cells and the surrounding host stromal cells, and is involved in multiple complementary, overlap, and independent pathways (4, 7, 8, 10, 11, 12, 13, 66). As consequence, it is likely that blockade of one angiogenic pathway is neither enough to efficiently inhibit tumor angiogenesis nor to block tumor growth and metastasis. Thus, it is important to understand the roles of the important angiogenic factors in tumor angiogenesis and the underlying mechanisms of their functions. The understanding might lead to the development of successful combination therapies to block multiple angiogenic pathways and tumor angiogenesis, growth and metastasis.

Angiopoietins are potentially important as regulators of tumor angiogenesis due to following three reasons. First, Ang-1 and -2 is a naturally occurring agonist and antagonist Tie-2, respectively. Second, Ang-1 and -2 displayed different ECM binding capacity. Ang-2 is secreted, whereas Ang-1 incorporates into the ECM. The difference in the ECM binding suggests that Ang-2 can diffuse from their production site to affect angiogenesis at distant metastatic sites, whereas Ang-1 likely affects local angiogenesis, unless the mechanisms are deployed to block its binding to the ECM and/or to release Ang-1 from the ECM. Third, Tie-2 is primarily expressed by ECs. Thus, Tie-2-angiopoietin functional axis serves as a relative specific target for anti-angiogenesis based cancer therapy without the risk of potential side effects on other cell types.

Figure 4:
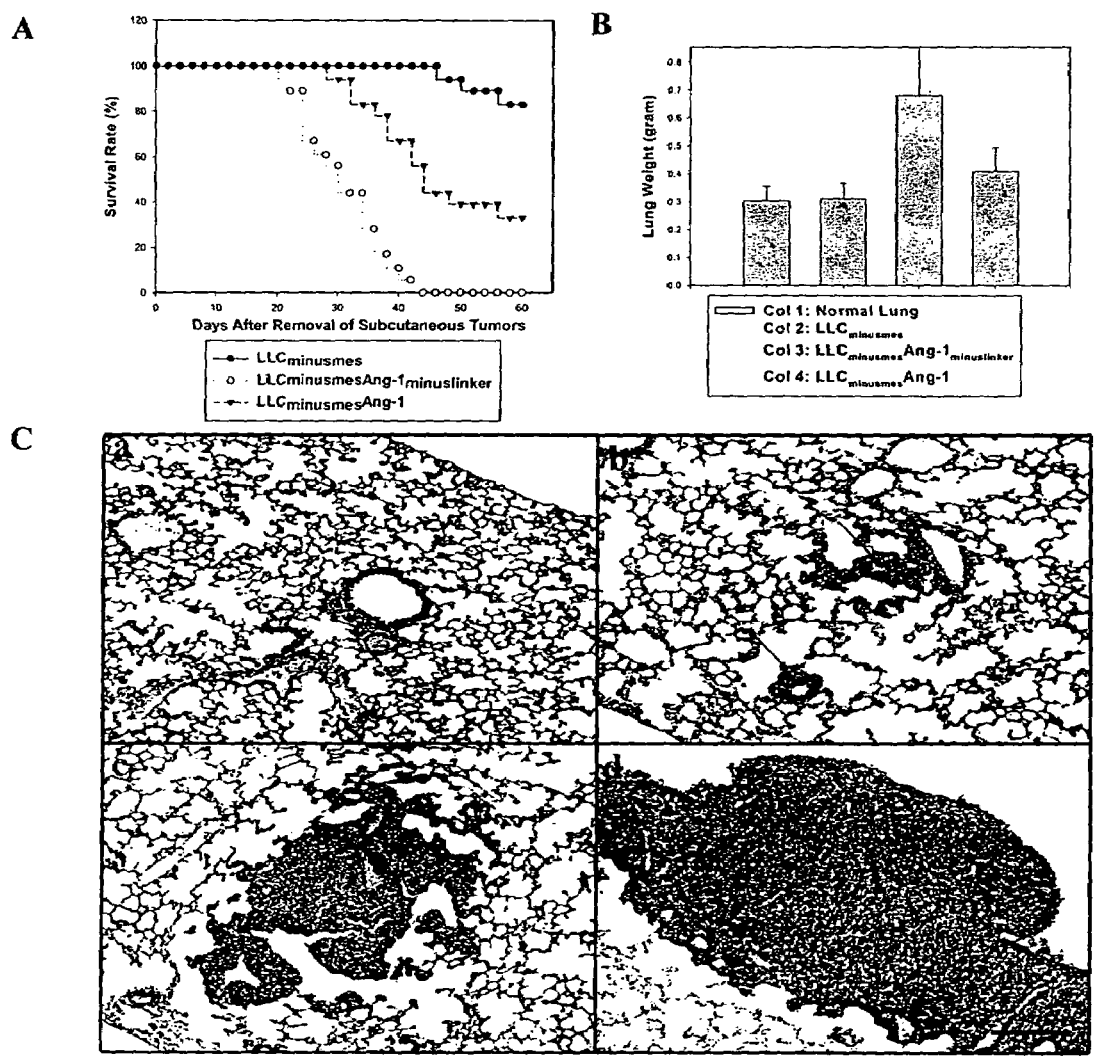
FIG. 4: Ang-1minusliner promotes spontaneous pulmonary metastasis of LLCminusmes cells much more effectively than wild type Ang-1. Transfected LLCminusmes cells ($1\times10^6$) were injected subcutaneously (s.c.) into syngeneic C57BL mice. 3 independent isolates of each transfectant were used. 6 mice were injected for each transfectant. The solid tumors were removed surgically 3-weeks after injection when the size of the tumor is approximately 1 cm in diameter. A. The survival rate of the mice after the surgery. B. To determine the extent of pulmonary metastasis, three weeks after the surgery, the mice were sacrifice and the lungs were dissected out and weighted. The data represent the average lung weight +/− SD. Normal lung: normal health lungs derived from the mice to which no tumor cells were injected. LLC$_{minusmes}$, LLCminusmesAng-1, and LLCminusmesAng-1minus linker represent LLC$_{minusmes}$ cells transfected with the expression vector alone or expressing Ang-1 or Ang-1minuslinker. C. Hematoxylin and eosin (H & E) stained sections of the normal health lung (C-a), or the lungs derived from the mice injected with LLC$_{minusmes}$ (C-b).

The results obtained so far support that Ang-1 and -2 play important opposite roles in tumor growth and metastasis by regulating tumor angiogenesis. We showed that 1) Ang-2 inhibits spontaneous pulmonary metastasis of LLC cells by blocking progression of micrometastases to lift-threatening macrometastatic lesions (FIG. 5); and 2) the non-ECM binding mutant of Ang-1 promotes spontaneous pulmonary metastasis of LLC cells much more effectively than wild type Ang-1 (FIG. 4).

Results:

Ang-1 and Ang-2 Displayed Different Ability to Bind to the ECM and Different Capacity to Disseminate from their Production Sites in vivo It has been shown recently that unlike mouse Ang-2, which is secreted, mouse Ang-1 is incorporated into the ECM (32). To determine whether this is true for the human homologs of mouse Ang-1 and Ang-2, Ang-1$_{human}$ and Ang-2$_{human}$ were cloned by RT-PCR from mRNAs of human placenta. The expression constructs containing v5-epitope tagged Ang-1$_{human}$ and Ang-2$_{human}$ were used to transfect Cos-7 cells. The v5 epitope is a 14 amino acid epitope derived from P and V proteins of the paramyxovirus, SV5 (68, Invitrogen). Attachment of short peptide tags to the proteins of interest has been used extensively for easy identification and purification of the intended proteins including angiopoietins (28, 30, 69, 70, 71). Seventy-two hours after the transfection, the proteins derived from the culture supernatants and the ECM were analyzed by Western blotting with anti-v5 monoclonal antibody (mAb). The result indicated that like their mouse counterparts, Ang-1$_{human}$ is incorporated into the ECM and Ang-2$_{human}$ is secreted (FIG. 1A).

To investigate how the difference in the ECM binding affects ability of Ang-1 and Ang-2 to diffuse away from their production sites in vivo, LLC transfectants expressing Ang-1 or Ang-2 were injected subcutaneously into the syngenic C57BL/6 mice as described (31). The subcutaneous tumors, were allowed to grow for 3-4 weeks to reach approximate 1.5 cm in diameter in size. The mice bearing these solid tumors were bled by making cuts on their tails, and approximate 200 µl blood from each mouse were collected. After spinning down the cells, the supernatants of the blood samples were used in immunoprecipitation using anti-v5 mAb conjugated agarose beads (Sigma). The precipitated proteins were eluted and analyzed by Western blotting with anti-v5 mAb. The solid tumors were extracted with phosphate buffer containing various proteinase inhibitors, and the insoluble materials were then extracted with 2M Urea buffer (32), which extracts the ECM and the ECM-bound proteins, as well as the proteins bound to transmembrane proteins and in intracellular compartments. The extracted proteins were analyzed by Western blotting with anti-v5 mAb. The results showed that Ang-2v5 proteins were detected in the serum samples and in the PBS extractable fraction of solid tumors, i.e. soluble (FIG. 1B). On the contrary, little amount of Ang-1v5 proteins was detected in the serum samples and most if not all of Ang-1v5 proteins in the urea extractable fraction of the solid tumors, i.e. ECM-associated (FIG. 1B). Lack of Ang-1 proteins in serum sample and PBS extraction is consistent with its association with the ECM. Together, these results indicated that the binding to the ECM blocks dissemination of Ang-1 proteins from its production site, whereas Ang-2 can readily diffuse away via circulation, which may affect angiogenesis at the distant metastatic sites. The activity balance of Ang-1 and Ang-2 at local and distant sites may play important roles in regulating dormancy of micrometastases.

The Linker Peptide Region of Ang-1 Mediates the Binding of Ang-1 to the ECM

Figure 2:
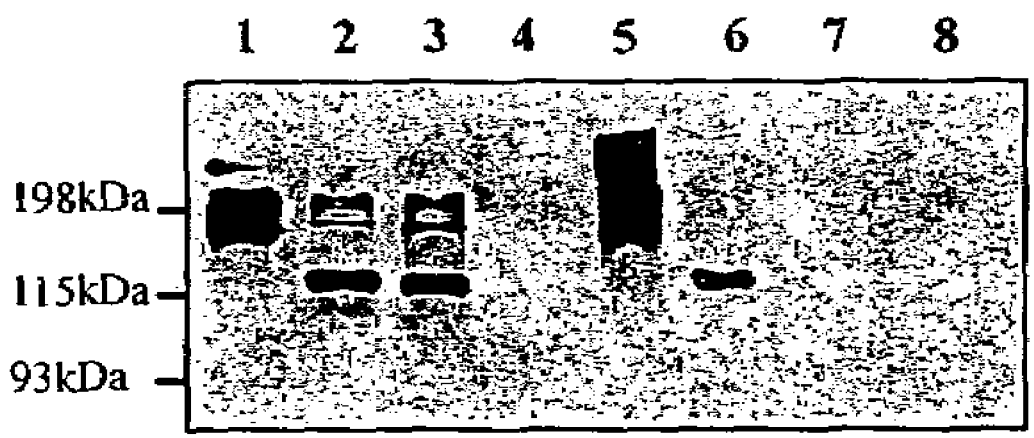
FIG. 2: The linker peptide region mediates the ECM binding of Ang-1. The expression constructs containing v5-ttagged wild type Ang-1, Ang-1$_{minuslinker}$, or Ang-1$_{cys2654ser}$ were sued to transfect Cos-7 cells. 72 hours after transfection, the cell culture supernatants (lanes 1-4) and the ECM materials (lanes 5-8) were analyzed by Western blotting with anti-v5 mAb to determine the distribution of Ang-1 and the Ang-1 mutants. Proteins were derived from Cos-7 cells transfected with wild-type Ang-1 (lanes 1 and 5), Ang-1$_{cys265ser}$ (lanes 2 and 6), Ang-1$_{minuslinker}$ (lanes 3 and 7), or the expression vectors alone (lanes 4 and 8).

It has been shown recently that the linker peptide region between the coiled-coil and the fibrinogen-homology domain (FHD) of Ang-1 likely mediates that interaction between Ang-1 and the ECM (32). The linker peptide region contains 26 amino acids ($_{258}$VHNLVSL$_{265}$CTKEGVLLKGGKREEEKTIF$_{283}$), and is highly conserved among different species. There is 96% identity at the amino acid level between human and mouse in this region. To confirm that the linker peptide region mediates the ECM binding of Ang-1 and determine the role of the cysteine265 residue, which is conserved among different species and unique to Ang-1, in the ECM binding of Ang-1, two Ang-1 mutants, in which either the linker peptide region was deleted (Ang-1$_{minuslinker}$), or the cysteine265 residue was mutated into a serine residue (Ang-1cys265ser) were generated. The expression constructs (pEF/6His-v5, Invitrogen) containing wild type Ang-1, Ang-1$_{minuslinker}$, and Ang-1cys265ser were used to transfect Cos-7 cells using Lipofectamine™ liposome reagent. Seventy-two hours after the transfection, the cell culture supernatants and the ECM materials deposited by the transfected cells were analyzed by Western blotting with anti-v5 mAb to determine the distribution of Ang-1 and the Ang-1 mutants. The results showed that the Ang-1 mutant that lacks the linker peptide region, Ang-1$_{minuslinker}$, displayed dramatically reduced binding to the ECM, and the mutation of cysteine$_{265}$ residue to a serine reduced the ECM binding of the mutants. Both mutations alter the aggregation pattern as well compared to that of wild type Ang-1 (FIG. 2). This result demonstrated the importance of the linker peptide region and the cysteine265 residue in the ECM binding of Ang-1 and provided us with useful tools to study how the ECM binding affects the function of Ang-1.

Soluble Ang-1 is Cleaved at the Linker Peptide Region

Figure 3:
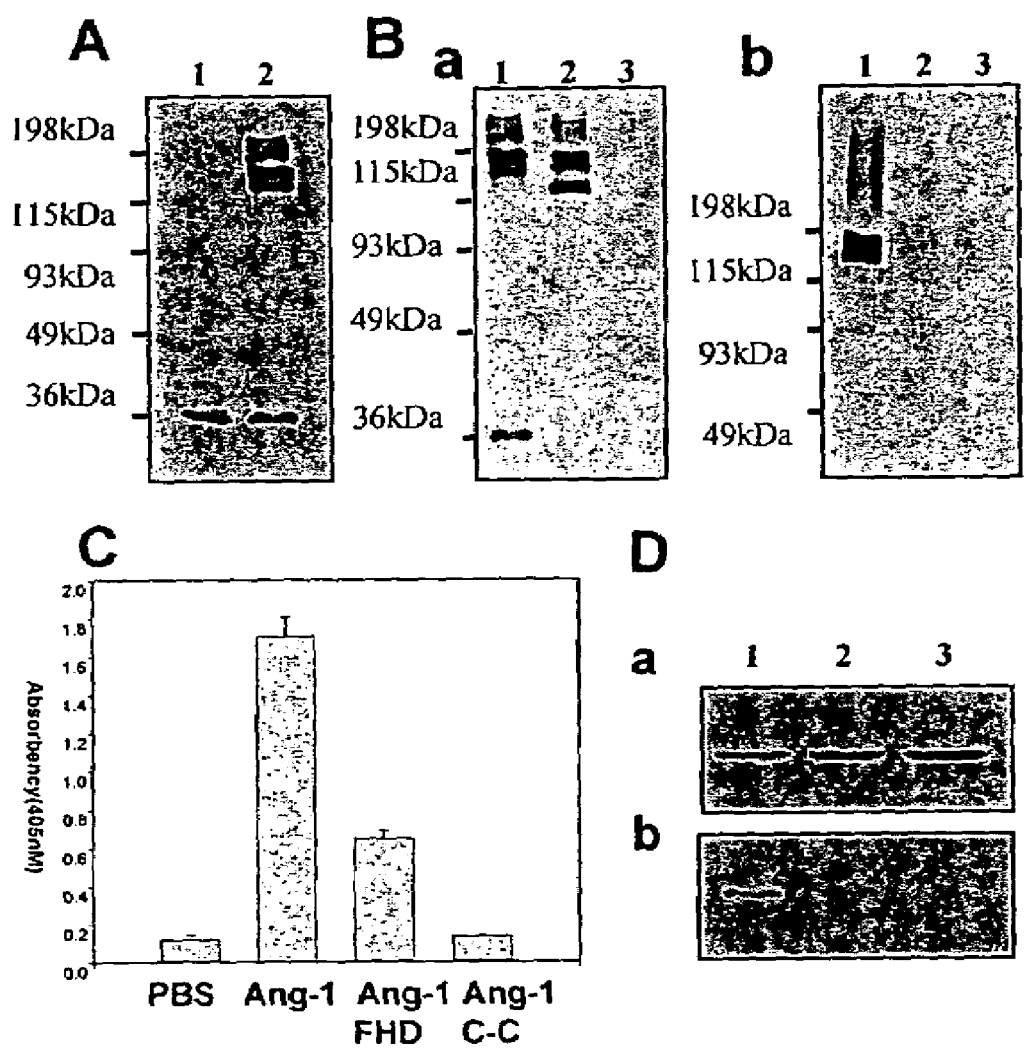
FIG. 3: Soluble Ang-1 is cleaved at the linker peptide region. A. The size of the C-terminal cleavage fragment of Ang-1 (lane 2) is similar to that of Ang-1FHD (lane 1, 32). B. Cos-7 cells were transfected with wild type Ang-1 (lane 1), Ang-1minus linker (lane 2), and the empty expression vector (lane 3). Proteins derived from the cell culture supernatants (B-a) and the ECM (B-b) were analyzed by Western blotting with anti-v5 mAB. C. Ang-1FHD, Ang-1C-C, and full-length Ang-1 proteins were coated on the 96-well Elisa plates in triplicate. After blocking the plates with BSA, 10 µg/ml of Tie-2Fc fusion proteins were applied to the plates and the bound Tie-2-Fc proteins were detected and the data were presented as means =/− SD. D. Ang-1FHD failed to induce Tie-2 phosphorylation. Unlike full-length Ang-1 (lane 1), Ang-1FHD (lane 2) and Ang-1C-C (lane 3) did not induce phosphorylation of Tie-2 on HUVECs. The total Tie-2 proteins were detected by Western blotting with anti-Tie-2 antibody (Santa Cruz, D-a), and the phosphorylated Tie-2 proteins in the immunoprecipitates were detected by Western Blotting with anti-phosphotyrosine (D-b).

Western blot analysis indicated that Ang-1 protein is cleaved, and the size of the C-terminal cleavage fragment of Ang-1 (c-Ang-1) is similar to that of FHD fragment of Ang-1 (Ang-1FHD), suggesting that the cleavage occurred at the linker peptide regions (FIG. 3A). To confirm this, the expression constructs containing wild type Ang-1 and Ang-1minuslinker were used to transfect Cos-7 cells, two days after the transfection, these cells were switched to serum-free culture medium and cultured for 4 additional days. The serum-free culture supernatants and the ECM of the transfected cells were analyzed by Western blotting with anti-v5 mAb. The results indicated that soluble Ang-1 in cell culture supernatants was cleaved, whereas Ang-1minuslinker is resistant to the cleavage. No cleavage fragments of Ang-1 were detected in the ECM fraction (FIG. 3B). This result demonstrated that the soluble Ang-1 is cleaved in the linker peptide region, which likely destroys the ECM binding site within the region and prohibits the incorporation of the fragments of Ang-1 into the ECM.

To determine whether the C-terminal cleavage fragment of Ang-1 (c-Ang-1) binds to and activates Tie-2 receptor, we need purified c-Ang-1 proteins. Although the exact cleavage site in Ang-1 has not yet been identified, it was located within the linker peptide region containing 26 amino acids. Thus, the expression construct, which contains the signal peptide plus the v5 tagged FHD fragment of Ang-1 (Ang-1FHD) was used. As shown in FIG. 3A, transient expression of Ang-1FHD expression construct in Cos-7 cells generated a secreted protein (Ang-1FHDv5) with a similar molecular weight as that of c-Ang-1. Therefore, it is believed that Ang- 1FHDv5 is very similar to c-Ang-1 fragment. Thus, the expression constructs containing v5-tagged Ang-1FHD and the coiled-coil fragment of Ang-1 (Ang-1C-C, 32) were used to transfect Cos-7 cells. Ang-1FHDv5 and Ang-1C-Cv5 proteins were purified from these Cos-7 cell-culture supernatants as described (32). The affinity purified Ang-1FHDv5 protein but not Ang-1C-Cv5 binds to Tie-2-Fc fusion protein in a solid phase binding assay (FIG. 3C). However, unlike full-length Ang-1, Ang-1FHD failed to induce Tie-2 phosphorylation on HUVECs (FIG. 3D). This result is consistent with a very recent report indicating that the tetramers of Ang-1 are the minimal size required for activating Tie-2 receptors on endothelial cells (99). This result suggested that the c-Ang-1 likely acts as a dominant negative regulator of full-length Ang-1.

Two Spontaneous Pulmonary Metastatic Models were Established Using LLC Cells

It is well established that tumor cells are often heterogeneous and display different properties, including differences in promoting angiogenesis and in metastatic potential (95, 96). To eliminate variations and to establish two different spontaneous pulmonary metastatic models, parental LLC cells were transfected with the expression vector containing the neomycin-resistant gene and selected for G418 resistance. 2-3 weeks after the selection, the clonal G418 resistant cells were isolated and tested for their ability to undergo spontaneous pulmonary metastasis. To achieve that, the clonal LLC cells ($1\times10^6$/mouse) were injected into the left flanks of the syngenic C57BL/6 mice and allow grow until the size of the tumors is approximately 1-1.5 cm in diameter 2-3 weeks after the tumor implantation. The solid tumors were then removed surgically and the mice were sacrificed three to four weeks after the surgery and, the lungs were removed. The pulmonary metastatic tumor nodules were dissected out and cultured in the cell culture medium containing G418 (500 μg/ml) to eliminate any contaminated host cells. The drug-resistant LLC cells derived from the pulmonary metastatic nodules were injected back to C57BL/6 mice subcutaneously and two additional rounds of selections for pulmonary metastatic LLC cells were carried out, and a clonal LLC cell, LLCmes, was established for its ability to form aggressive pulmonary metastases. Another clonal LLC cell, $LLC_{minusmes}$, was established as well for its inability to undergo aggressive pulmonary metastasis.

The Ang-1 mutant that lacks the ECM-binding linker peptide region promotes spontaneous pulmonary metastasis of $LLC_{minusmes}$ cells much more effectively than wild type Ang-1.

To test the hypothesis that the ECM binding of Ang-1 negatively regulates its pro-angiogenic activity, wild type Ang-1 and Ang-$1_{minuslinker}$ (FIG. 2) that lacks the ECM-binding linker peptide region were transfected into $LLC_{minusmes}$ cells which are incapable of aggressive pulmonary metastasis. Three independent clonal $LLC_{minusmes}$ transfectants expressing a similar level of wild type Ang-1 ($LLC_{minusmesAng-1}$) or Ang-$1_{minuslinker}$ ($LLC_{mninusmesAng-1minuslinker}$), or transfected with the expression vector alone: ($LLC_{minusmes}$) were identified. Histology analysis indicated that $LLC_{minusmes}$ cells are capable of forming micrometastases in host lung parenchyma, however, these micrometastases did not develop into life-threatening macrometastases, strongly suggesting that adequate angiogenesis is not established. Thus, it serves as a good model to investigate the roles of pro-angiogenic factors such as Ang-1 in spontaneous pulmonary metastasis.

The spontaneous pulmonary metastasis assay was performed as described in section C4a using these transfectants. The results showed that expression of Ang-1minuslinker promotes pulmonary metastasis of LLCminusmes cells much more effectively than wild type Ang-1 (FIG. 4), suggesting that the ECM binding negatively regulates the pro-angiogenic activity of Ang-1.

Ang-2 Inhibits Spontaneous Pulmonary Metastasis of LLCmes Cells

It has been shown that overexpression of Ang-2 inhibits experimental tumor metastasis (31). In these experiments, $1\times10^6$ of LLC and TA3 cells expressing Ang-2 were injected into the tail veins of syngenic mice. Because spontaneous pulmonary metastasis is more similar to the normal development of pulmonary metastasis, we investigated the role of Ang-2 in this process. To achieve that, $LLC_{mes}$ cells, which is capable of aggressive spontaneous pulmonary metastasis after removal of the primary solid tumors, were transfected with Ang-2 or the empty expression vector alone. Three independent clonal $LLC_{mes}$ transfectants expressing Ang-2 ($LLC_{mesAng-2}$) or transfected with the empty expression vectors were identified. The spontaneous pulmonary metastasis assay was performed as described (4). These studies showed that at the early stage of pulmonary metastasis (immediately after removal of the primary solid tumors), $LLC_{mesAng-2}$ (FIG. 5C-c), and LLCmes (FIG. 5C-b) cells form micrometastases, which are attached to the host blood vessels (arrows). This observation supports the vessel co-option theory (48), which hypothesize that tumor cells grow on the existing host blood vessels initially, then evoke angiogenesis to keep the progression of the tumor mass (1, 2, 3, 7, 11, 12, 47, 66).

As noted previously, micrometastases are often difficulty to identify. I knew that LLC cells express high level of CD44 proteins, the receptor of a matrix component, hyaluronan, while in normal health mouse lung, the evenly distributed macrophages are the major CD44 positive cells (data not shown). Using this knowledge, highlighting the localization of the micrometastases was performed by staining the lung sections with anti-CD44 antibody (FIG. 5C-b and C-c). This result was confirmed by H&E staining of the adjacent sections. The micrometastases derived from $LLC_{mes}$ cells were able to progress and form large metastatic lesions 2.5-weeks after removal of the primary tumors (FIG. 5C-e). However, the expression of Ang-2 inhibited the progression of the micrometastases derived from $LLC_{mesAng-2}$ cells (FIG. 5C-f; arrow) implying that adequate angiogenesis is not established in these micrometastases.

Summary of Results:

A novel and potentially important biochemical property of Ang-1 has been uncovered: Ang-1 binds to the ECM via its linker peptide region, and an important difference in the ECM binding between Ang-1 and Ang-2 (32, FIGS. 1-2). It has been shown that the ECM-binding of Ang-1 blocks the Ang-1-Tie-2 interaction, and dissemination of Ang-1 from its production site in vivo, whereas Ang-2-Tie-2 binding is not regulated by the ECM and it can diffuse away from its production site in vivo (FIG. 1). Furthermore, it was demonstrated that soluble Ang-1 but not the ECM-bound, Ang-1 is cleaved at the linker peptide region and the C-terminal cleavage fragment, c-Ang-1, may acts as a dominant negative regulator of the full-length Ang-1. Several obstacles have been overcome to purify angiopoietin proteins and generated an Ang-1 mutant, Ang-$1_{minuslinker}$ in which the ECM-binding linker peptide region was deleted. Ang-$1_{minuslinker}$ not only displayed dramatically reduced binding to the ECM but also is resistant to proteolytic cleavage.

Figure 5:
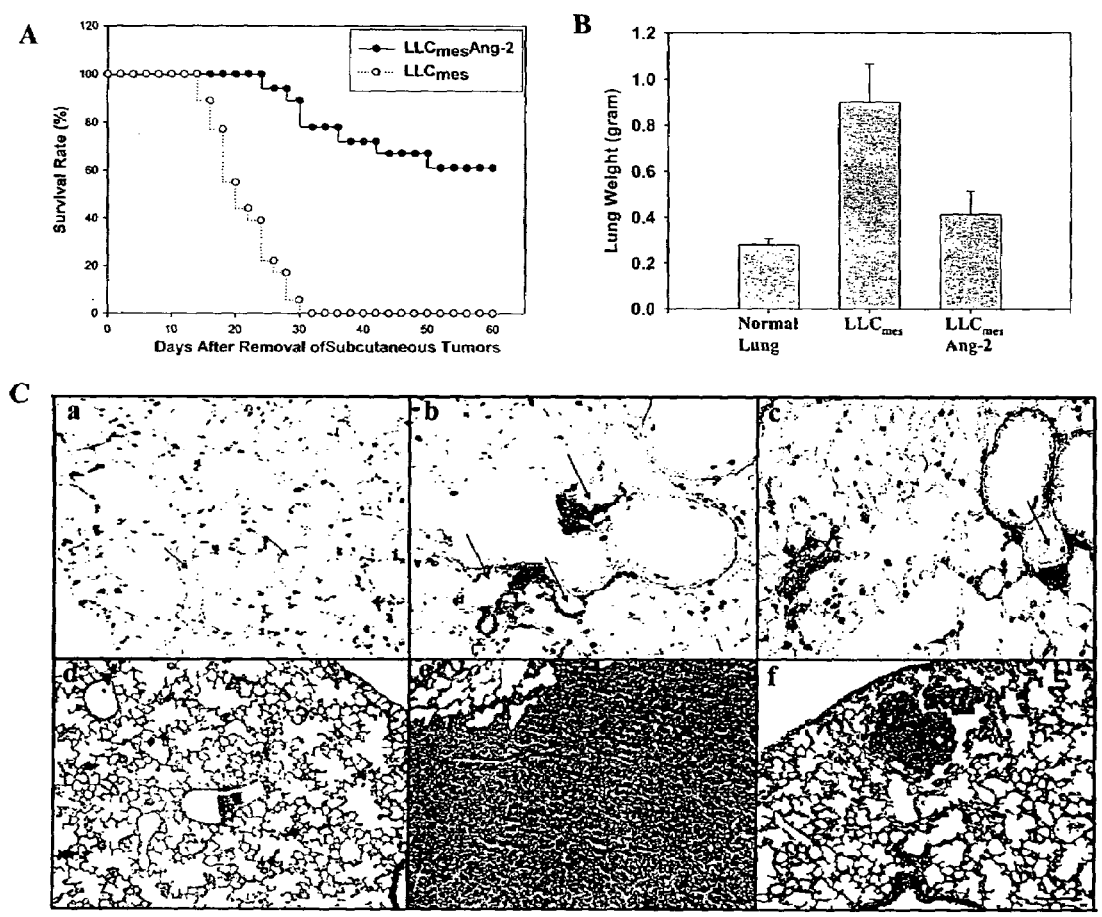
FIG. 5: Ang-2 inhibits spontaneous pulmonary metastasis of LLC$_{mes}$. The spontaneous pulmonary metastatic assay was performed using transfected LLC$_{mes}$ expressing Ang-2 (LLC$_{mes}$Ang-2) or transfected with the empty expression vector (LLC$_{mes}$). 3 independent isolates of each transfectant were used. 6 mice were injected for each transfectant. A. The survival rate of the mice after surgery. b. The extent of pulmonary metastasis was determined by the weight of the lungs dissected out from the sacrifice mice two and half weeks after the removal of the primary subcutaneous tumors. C. Immediately after removal of the primary tumors, pulmonary micrometastases derived from LLC$_{mes}$ (C-b) or LLC$_{mes}$ Ang-1 (C-c) were highlighted by anti-CD44 mAb, IM7.8. These micrometastases are localized around host pulmonary blood vessels (indicated by the arrows) C-a, the normal lung section stained with anti-CD44 mAb. Hematoxylin and eosin (H&E) staining of the normal lung section (C-d), and the ling sections derived from the mice 2.5 weeks after removal of the s.c. solid tumors derived from LLCmes (C-e) or LLCme-sAng-2 (C-f) cells. Bar: 200 μm.

Two spontaneous pulmonary metastasis models have also been established. Using LLC transfectants expressing Ang-1 or Ang-2, it has been demonstrated that Ang-1 and Ang-2 play opposite roles in spontaneous pulmonary metastasis of LLC cells and developed the hypothesis that this is due to their different effects on tumor angiogenesis. It has been demonstrated that Ang-1$_{minuslinker}$ promotes pulmonary metastasis of LLC$_{minusmes}$ cells much more efficiently than wild type Ang-1 (FIG. 4) suggesting the ECM binding of Ang-1 negatively regulates its function; whereas Ang-2 blocks pulmonary metastasis of LLCmes cells by inhibiting the progression of micrometastases to macrometastatic lesions (FIG. 5).

Example 3

Ang-1 was also discovered to have an additional ECM binding domain at the N-terminal end of Ang-1 in addition to the linker peptide region described in above. The N-terminal ECM binding domain is expected to have a coiled-coil structure and has a sequence of SEQ ID NO: 3 or SEQ ID NO:4 in human and mouse respectively. The peptides can be encoded by nucleotide sequences having the sequence SEQ ID NO: 21 or SEQ ID NO: 22, respectively.

Figure 6:
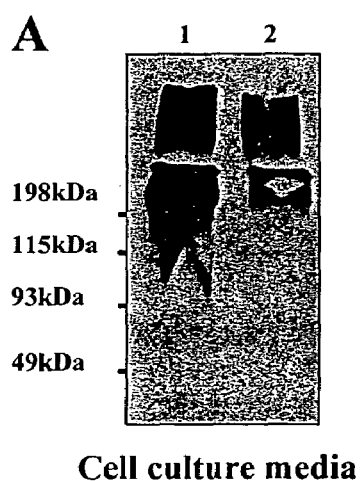
FIG. 6: A deletion Ang-1 mutant lacking the N-terminal coiled-coil ECM binding domain (NQRRNPENGGRRYN-RIQHGQCAYTFILPEHDGNCRESATEQY), Ang-1$_{minusN-ECM}$, displayed a marked reduction in its binding to the ECM.
Figure 6:
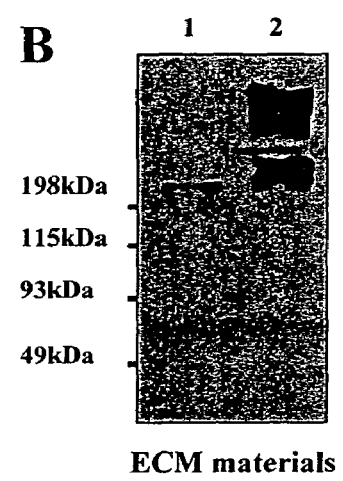
Figure 6:
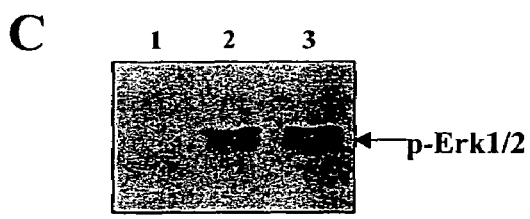
Figure 6:
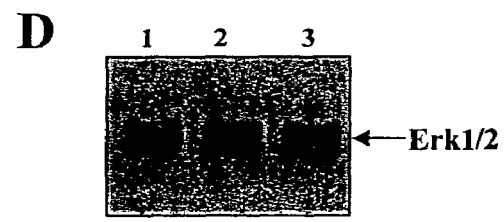

The deletion mutant of Ang-1 lacking the N-terminal coiled-coil ECM binding domain (Ang-1$_{minusN-ECM}$) displayed significant reduction in its binding to ECM and also was found to promote the activation of Erk1/2 kinase effectively (FIG. 6). Western blot was performed under non-reducing conditions using antibodies against the v5 epitope tag at the C-terminal end of either the full length or Ang-1$_{minusN-ECM}$ proteins to determine their distribution patterns in the cell culture supernatants (FIG. 6, Panel A) and in the ECM (FIG. 6, Panel B) of Lewis Lung Carcinomal transfectants expressing either full-length Ang-1 (lane 2 in Panels A and B) or Ang-1$_{minusN-ECM}$ (lane 1 in Panels A and B).

HUVEC cells were cultured until subconfluence, switched into serum free media (SFM) and cultured overnight. SFM alone (FIG. 6, Panels C and D, lane 1), SFM containing 100 ng purified Ang-1 (FIG. 6, Panels C and D, lane 2), Ang-1$_{minusN-ECM}$ (FIG. 6, Panels C and D, lane 3) was applied to serum-starved HUVECs for 25 minutes. The cells were then lysed and the protein samples were analyzed by Western blotting with anti-phospho-Erk1/2 antibody (Panel C) to detect phospho-Erk1/2 (p-Erk1/2) proteins and anti-Erk (Panel D) to detect total Erk1/2 proteins. Results demonstrate that Ang-1$_{minusN-ECM}$ can induce the phosphorylation of Erk1/2 to the same extent as full-length.

Figure 7:
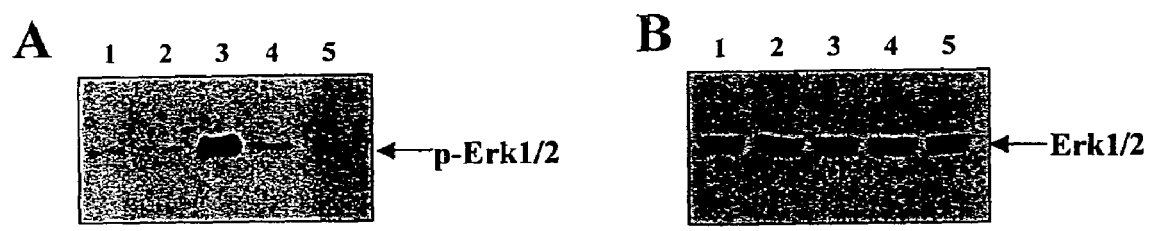
FIG. 7: The C-terminal cleavage fragment of Ang-1, c-Ang-1 blocks activation of Erk1/2 kinase induced by Ang-1.

The C-terminal cleavage fragment of Ang-1 (c-Ang-1) blocks the activation of Erk1/2 kinase induced by Ang-1. HUVEC cells were cultured until subconfluence, switched into serum free media (SFM) and cultured overnight. SFM alone (FIG. 7, lane 1), SFM containing 800 ng of purified c-Ang-1(FIG. 7, lane 2), 100 ng of Ang-1 (FIG. 7, lane 3) or Ang-1 (100 ng) plus 800 ng (FIG. 7, lane 4) or 1600 ng (FIG. 7, lane 5) of c-Ang-1 were applied to the serum-starved HUVECs for 25 minutes. The cells were then lysed and the protein samples were analyzed by Western blotting with anti-phospho-Erk1/2 antibody (A) to detect phospho-Erk1/2 (p-Erk1/2) proteins and anti-Erk (B) antibody to detect total Erk1/2 proteins. The experiment c-Ang-1 can inhibit the Ang-1 induced activation of Erk1/2.

Figure 8:
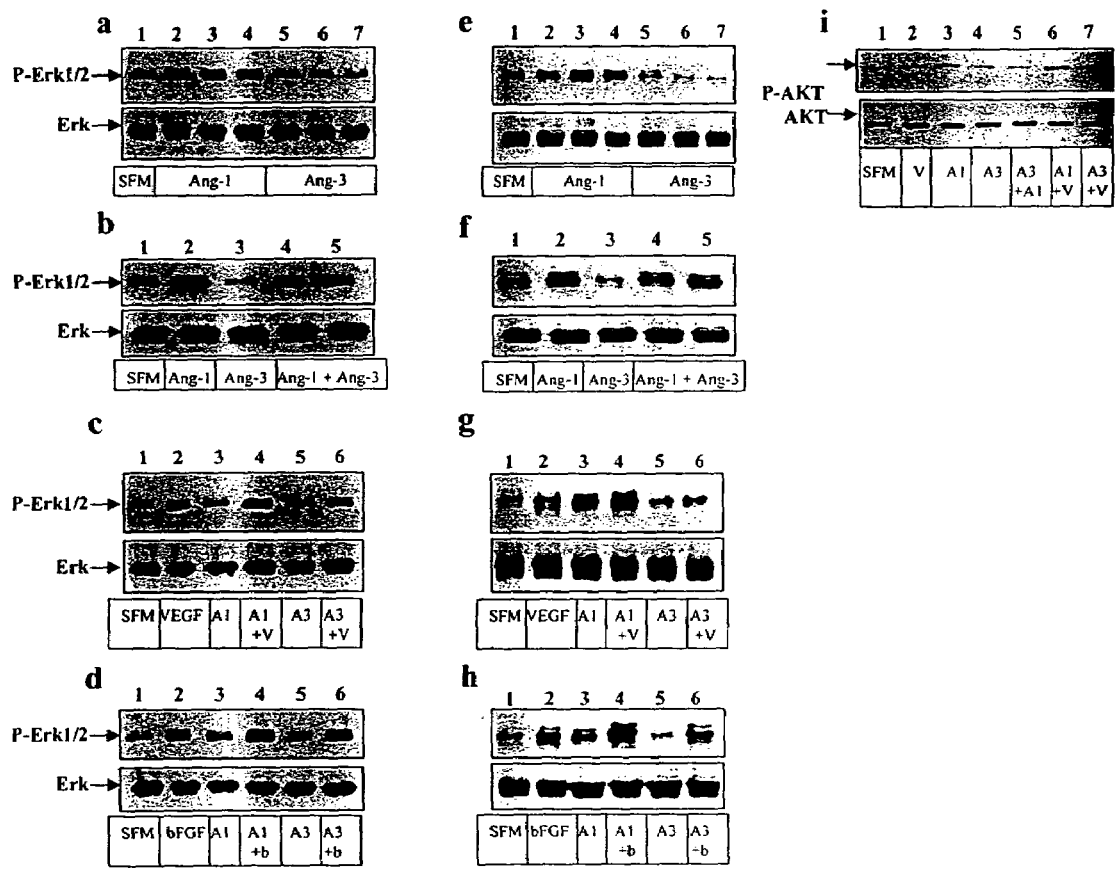
FIG. 8: Ang-3 blocks activation of Erk1/2 kinases induced by Ang-1 or VEGF$_{165}$.

The properties of Ang-3 were investigated to determine if Ang-3 can block the activation of Erk1/2 by Agn-1 or VEGF$_{165}$. Different amount of Ang-1, Ang-3, VEGF, and bFGF in different combinations were applied to the serum-starved HUVECs for either 25 minutes (FIG. 8, Panels a, b, c, and d) or 24 hours (FIG. 8 Panels e, f, g, h, and i). The cells were lysed and the protein samples were analyzed by Western blotting with anti-phospho-Erk1/2 (FIG. 8, upper panels in a-h) or anti-phospho-Akt antibody (FIG. 8, upper panel in i) to detect phospho-Erk1/2 (p-Erk1/2) or phospho-Akt (p-Akt), respectively. The membranes were then stripped to apply anti-Erk (FIG. 8, bottom panels in a-h) or anti-Akt (FIG. 8, bottom panel in i) antibody to detect total Erk or Akt protein, respectively. In panels a and e, 50, 100, 200 ng of Ang-1 (FIG. 8, lanes 2-4) or Ang-3 (FIG. 8, lanes 5-6) were used. In panels b and f, 100 ng Ang-1 or 200 ng of Ang-3 were used separately (lanes 2-3) or in combination as indicated in the panels (FIG. 8, lanes, 4-5). In panels c-i, 15 ng of VEGF165 or bFGF, 100 ng of Ang-1 or 200 ng of Ang-3 were used alone or in combination as indicated in the panels. A1 stands for Ang-1; A3 stands for Ang-3; V stands VEFG165, and b stands for bFGF. The results show that Ang-3 blocks the activation of Erk1/2 kinases, which have been induced by either Ang-1 or VEGF$_{165}$.

LITERATURE CITED which is incorporated herein by reference.

1. Folkman, J. (1971). Tumor angiogenesis: therapeutic implications. N. Engl. J. Med. 285, 1182-1186.
2. Folkman, J. (1986). How is blood vessel growth regulated in normal and neoplastic tissue? Cancer Res. 46, 467-473.
3. Folkman, J. (1995). Angiogenesis in cancer, vascular, rheumatoid and other disease. Nat. Med. 1, 27-31.
4. Risau, W. (1997). Mechanisms of angiogenesis. Nature 386, 671-674.
5. Kim, K. J., Li, B., Winer, J., Armanini, M., Gillett, N., Phillips, H. S., and Ferrara, N. (1993). Inhibition of vascular endothelial growth factor-induced angiogenesis suppresses tumour growth in vivo. Nature 362, 841-844.
6. Koch, A. E., Halloran, M. M., Haskell, C. J., Shah, M. R., and Polverini, P. J. (1995). Angiogenesis mediated by soluble forms of E-selectin and vascular cell adhesion molecule-1. Nature 376, 517-519.
7. Hanahan, D., and Folkman, J. (1996). Patterns and emerging mechanisms of the angiogenic switch during tumorigenesis. Cell 86, 353-364.
8. Hanahan, D. (1997). Signaling vascular morphogenesis and maintenance. Science 277, 48-50.
9. Hanahan, D., and Weinberg, R. A. (2000). The hallmarks of cancer. Cell 100, 57-70.
10. Folkman, J., and D'Amore, P. (1996). Blood vessel formation: what is its molecular basis? Cell 87, 1153-1155.
11. Yancopoulos, G. D. (1999). The angiopoietins: Yin and Yang in angiogenesis. Curr. Top Microbiol. Immunol. 237, 173-185.
12. Yancopoulos, G. D., Davis, S., Gale, N. W., Rudge, J. S., Wiegand, S. J., Holash, J. (2000). Vascular-specific growth factors and blood vessel formation. Nature 407, 242-248.
13. Ingber, D. E., and Folkman, J. (1989). How does extracellular matrix control capillary morphogenesis? Cell 58, 803-805.
14. Ramsauer, M., and D'Amore, P. A. (2002). Getting Tie(2)d up in angiogenesis. J. Clin. Invest. 110, 1615-1617.
15. Lindahl, P., Hellstrom, M., Kalen, M., and Betsholtz, C. (1998). Endothelial-perivascular cell signaling in vascular development: lessons from knockout mice. Curr. Opin. Lipidol. 9, 407-411.
16. Betsholtz, C., Karlsson, L., and Lindahl, P. (2001). Developmental roles of platelet-derived growth factors. Bioessays. 23, 494-507.
17. Fong, G.-H., Rossant, J., Gertsenstein, M., and Breitman, M. L. (1995). Role of the Flt-1 receptor tyrosine kinase in regulating the assembly of vascular endothelium. Nature 376, 66-70.

18. Davis, S., Aldrich, T. H., Jones, P. F., Acheson, A., Compton, D. L., Jain, V., Ryan, T. E., Bruno, J., Radziejewski, C., Maisonpierre, P. C., and Yancopoulos, G. D. (1996). Isolation of angiopoietin-1, a ligand for the TIE2 receptor, by secretion-Trap expression cloning. Cell 87, 1161-1169.

19. Maisonpierre, P. C., Suri, C., Jones, P. F., Bartunkova, S., Wiegand, S. J., Radziejewski, C., Compton, D., McClain, J., Aldrich, T. H., Papadopoulos, N., Daly, T. J., Davis, S., Sato, T. N., and Yancopoulos, G, D. (1997). Angiopoietin-2, a natural antagonist for Tie2 that disrupts in vivo angiogenesis. Science 277, 55-60.

20. Sato, T. N., Quin, Y., Kozak, C. A., and Audus, K. L. (1993). Tie-1 and Tie-2 define another class of putative receptor tyrosine kinase genes expressed in early embryonic vascular system. Proc. Natl. Acad. Sci. USA 90, 9355-9358.

21. Schnurch, H., and Risau, W. (1993). Expression of Tie-2, a member of a novel family of receptor tyrosine kinases, in the endothelial cell lineage. Development 119, 957-968.

22. Ziegler, S. F., Bird, T. A., Schneringer, K. A., Schooley, K. A., and Baum, P. R. (1993). Molecular cloning and characterization of a novel receptor protein tyrosine kinase from human placenta. Oncogene 8, 663-670.

23. Dumont, D. J., Gradwohl, G., Fong, G. H., Puri, M. C., Gertsenstein, M., Auerbach, A., and Breitman, M. L. (1994). Dominant-negative and targeted null mutations in the endothelial receptor tyrosine kinase, tek, reveal a critical tole in vasculogenesis of the embryo. Genes Dev. 8, 1897-1909.

24. Dumont, D. J., Gradwohl, G. J., Fong, G. H., Auerbach, R., and Breitman, M. L. (1993). The endothelial-specific receptor tyrosine kinase, tek, is a member of a new subfamily of receptors. Oncogene 8, 1293-1301.

25. Korhonen, J., Polvi, A., Partanen, J., and Alitalo, K. (1994). The mouse Tie receptor tyrosine kinase gene: expression during embryonic angiogenesis. Oncogene 9, 395-403.

26. Peters, K. G., Coogan, A., Berry, D., Marks, J., Iglehart, J. D., Kontos, C. D., Rao, P., Sankar, S., and Trogan, E. (1998). Expression of Tie2/Tek in breast tumour vasculature provides a new marker for evaluation of tumour angiogenesis. Br. J. Cancer 77, 51-56.

27. Sato, T. N., Tozawa, Y., Deutsch, U., Wolburg-Burcholz, K., Fujiwara, Y., Gendron-Maguire, M., Gridley, T., Wolburg, H., Risau, W., and Qin, Y. (1995). Distinct roles of the receptor tyrosine kinases Tie-1 and Tie-2 in blood vessel formation. Nature 376, 70-74.

28. Lin, P., Polverini, P., Dewhirst, M., Shan, S., Rao, P. S., and Peter, K. G. (1997). Inhibition of tumor angiogenesis using a soluble receptor establishes a role for Tie-2 in pathologic vascular growth. J. Clin. Invest. 100, 2072-2078.

29. Lin, P., Buxton, J. A., Acheson, A., Radziejewski, C., Maisonpierre, P. C., Yancopoulos, G. D., Channon, K. M., Hale, L. P., Dewhirst, M. W., George, S. E., and Peters, K. G. (1998). Antiangiogenic gene therapy targeting the endothelium-specific receptor tyrosine kinase Tie2. Proc. Natl. Acad. Sci. USA 95, 8829-8834.

30. Procopio, W. N., Pelavin, P. I., Lee, W. M. F., and Yeilding, N. M. (1999). Angiopoietin-1 and -2 coiled ciol domains mediate distinct homo-oligomerization patterns, but fibrinogen-like domains mediate ligand activity. J. Biol. Chem. 274, 30196-30201.

31. Yu, Q., and Stamenkovic, I. (2001). Angiopoietin-2 is implicated in the regulation of tumor angiogenesis. Am. J. Pathol. 158, 563-570.

32. Xu, Y., and Yu, Q. (2001). Angiopoietin-1, unlike angiopoietin-2, is incorporated into the extracellular matrix via its linker peptide region. J. Biol. Chem. 276, 34990-34998.

33. Shalaby, F., Rossant, J., Yamaguchi, T. P., Gertsenstein, M., Wu, X. F., Breitman, M. L., and Schuh, A. C. (1995). Failure of blood-island formation and vasculogenesis in Flk-1-deficient mice. Nature 376, 62-66.

34. Suri, C., Jones, P. F., Patan, S., Bartunkova, S., Maisonpierre, P. C., Davis, S., Sato, T. N., and Yancopoulos, G. D. (1996). Requisite role of angiopoietin-1, a ligand for the TIE2 receptor, during embryonic angiogenesis. Cell 87, 1171-1180.

35. Gale, N. W., and Yancopoulos, G. D. (1999). Growth factors acting via endothelial cell-specific receptor tyrosine kinases: VEGFs, angiopoietins, and ephrins in vascular development. Genes Dev. 13, 1055-1066.

36. Suri, C., McClain, J., Thursyon, G., McDonald, D. M., Zhou, H., Oldmixon, E. H., Sato, T. N., and Yancopoulos, G. D. (1998). Increased vascularization in mice overexpressing angiopoietin-1. Science 282, 468-471.

37. Thurston, G., Suri, C., Smith, K., McClain, J., Sato, T. N., Yancopoulos, G. D., and McDonald, D. M. (1999). Leakage-resistant blood vessels in mice transgenically overexpressing angiopoietin-1. Science 286, 2511-2514.

38. Thurston, G., Rudge, J. S., Ioffe, E., Zhou, H., Ross, L., Croll, S. D, Glazer, N., Holash, J., McDonald, D. M., and Yancopoulos, G. D. (2000). Angiopoietin-1 protects the adult vasculature against plasma leakage. Nat. Med. 6, 460-463.

39. Stratmann, A., Risau, W., and Plate, K. H. (1998). Cell type-specific expression of angiopoietin-1 and angiopoietin-2 suggests a role in glioblastoma angiogenesis. Am. J. Pathol. 153, 1459-1466.

40. Witzenbichler, B., Maisonpierre, P. C., Jones, P., Yancopoulos, G. D., and Isner, J. M. (1998). Chemotactic properties of angiopoietin-1 and -2, ligands for the endothelial-specific receptor tyrosine kinase Tie2. J. Biol. Chem. 273, 18514-18521.

41. Carlson, T. R., Feng, Y., Maisonpierre, P. C., Mrksich, M., and Morla, A. O. (2001). Direct cell adhesion to the angiopoietins mediated by integrins. J. Biol. Chem. 276, 26516-26525.

42. Papapetropoulos, A., Fulton, D., Mahboubi, K., Kalb, R. G., O'Connor, D. S., Li, F., Altieri, D. C., and Sessa, W. C. (2000). Angiopoietin-1 inhibits endothelial cell apoptosis via the Akt/survivin pathway. J. Biol. Chem. 275, 9102-9105.

43. Kim, I., Kim, H. G., So, J.-N., Kim, J. H., Kwak, H. J., and Koh, G. Y. (2000). Angiopoietin-1 regulates endothelial cell survival through the phosphatidylinositol 3'-kinase/Akt signal transduction pathway. Circ. Res. 86, 24-29.

44. Kwak, H. J., Lee, S. J., Lee, Y.-H., Ryu, C. H., Koh, K. N., Choi, H. Y., and Koh, G. Y. (2000). Angiopoietin-1 inhibits irradiation- and mannitol-induced apoptosis in endothelial cell. Circulation 101, 2317-2324.

45. Koblizek, T. I., Weiss, C., Yancopoulos, G. D., Deutsch, U., and Risau, W. (1998). Angiopoietin-1 induces sprouting angiogenesis in vitro. Curr. Biol. 8, 529-532.

46. Hayes, A. J., Huang, W.-Q., Mallah, J., Yang, D., Lippman, M. E. and Li, L.-Y. (1999). Angiopoietin-1 and its receptor Tie-2 participate in the regulation of capillary-like tubule formation and survival of endothelial cells. Microvasc. Res. 58, 224-237.

47. Holash, J., Wiegand, S. J., and Yancopoulos, G. D. (1999). New model of tumor angiogenesis: dynamic balance between vessel regression and growth mediated by angiopoietins and VEGF. Oncogene 18, 5356-5362.

48. Holash, J., Maisonpierre, D., Compton, D., Boland, P., Alexander, C. R., Zagzag, D., Alexander, C. R., Zagzag, D., Yancopoulos, G. D., and Wiegland, S. J. (1999). Vessel cooption, regression, and growth in tumors mediated by angiopoietins and VEGF. Science 284, 1994-1998.

49. Asahara, T., Chen, D., Takahashi, T., Fujikawa, K., Kearney, M., Magner, M., Yancopoulos, G. D., and Isner, J. M. (1998). Tie2 receptor ligands, angiopoietin-1 and angiopoietin-2, modulate VEGF-induced postnatal neovascularization. Circ Res. 83, 233-240.

50. Lauren, J., Gunji, Y., and Alitalo, K. (1998). Is angiopoietin-2 necessary for the initiation of tumor angiogenesis? Am. J. Pathol. 153, 1333-1339.

51. Oh, H., Takagi, H., Suzuma, K., Otani, A., Matsumura, M., and Honda, Y. (1999). Hypoxia and vascular endothelial growth factor selectively up-regulate angiopoietin-2 in bovine microvascular endothelial cells. J. Biol. Chem. 274, 15732-15739.

52. Mandriota, S. J., and Pepper. M. S. (1998). Regulation of angiopoietin-2 mRNA levels in bovine microvascular endothelial cells by cytokines and hypoxia. Circ. Res. 83, 852-859.

53. Kim, I., Kim, J.-H., Ryu, Y. S., Liu, M., and Koh, G. Y. (2000). Tumor necrosis factor-α upregulates angiopoietin-2 in human umbilical vein endothelial cells. Biochem. Biophys. Res. Commun. 269, 361-365.

54. Kim, I., Kim, H. G., Moon, S.-O., Chae, S. W., So, J.-N., Koh, K. N., Ahn, B. C., and Koh, G. Y. (2000). Angiopoietin-1 induces endothelial cell sprouting through the activation of focal adhesion kinase and plasmin secretion. Circ Res. 86, 952-959.

55. Valenzuela, D. M., Griffiths, J. A., Rojas, J., Aldrich, T. H., Jones, P. F., Zhou, H., McClain, J., Copeland, N. G., Gilbert, D. J., Jenkins, N. A., Huang, T., Papadopoulos, N., Maisonpierre, P. C., Davis, S., and Yancopoulos, G. D. (1999). Angiopoietins 3 and 4: diverging gene counterparts in mice and humans. Proc. Natl. Acad. Sci. USA 96, 1904-1909.

56. Siemeister, G., Schimer, M., Weindel, K., Reusch, P., Menrad, A., Marme, D., and Martiny-Baron, G. (1999). Two independent mechanisms essential for tumor angiogenesis: inhibition of human melanoma xenograft growth by interfering with either the vascular endothelial growth factor receptor pathway of the Tie-2 pathway. Cancer Res. 59, 3185-3191.

57. Carmeliet, P., Ferreira, V., Breier, G., Pollefeyt, S., Kieckens, L., Gertsenstein, M., Fahrig, M., Vandenhoeck, A., Harpal, K., Eberhardt, C., Declercq, C., Pawling, J., Moons, L., Collen, D., Risau, W., and Nagy, A. (1996). Abnormal blood vessel development and lethality in embryoslacking a single VEGF allele. Nature 380, 435-439.

58. Ferrara, N., Carver-Moore, Chen, H., Dowd, M., Lu, L., O'shea, K. S., Powell-Braxton, L., Hillan, K. J., and Moore, M. W. (1996). Heterozygous embryonic lethality induced by targeted inactivation of the VEGF gene. Nature 380, 439-442.

59. Kim, K. J., Li, B., Winer, J., Armanini, M., Gillett, N., Phillips, H. S., and Ferrara, N. (1993). Inhibition of vascular endothelial growth factor-induced angiogenesis suppresses tumor growth in vivo. Nature 362, 841-844.

60. Millauer, B., Shawver, L. K., Plate, K. H., Risau, W., and Ullrich, A. (1994). Glioblastoma growth inhibited in vivo by a dominant-negative Flk-1 mutant. Nature 367, 576-579.

61. Goldman, C. K., Kendall, R. L., Cabrera, G., Soroceanu, L., Heike, Y., Gillespie, G. Y., Siegal, G. P., Mao, X., Bett, A. J., Huckle, W. R., Thomas, K. A., and Curiel, D. T. (1998). Paracrine expression of a native soluble vascular endothelial growth factor receptor inhibits tumor growth, metastasis, and mortality rate. Proc. Natl. Acad. Sci. USA 95, 8795-8800.

62. Ahmad, S. A., Liu, W., Jung, Y. D., Fan, F., Wilson, M., Reinmuth, N., Shaheen, R. M., Bucana, C. D., and Ellis, L. M. (2001). The effects of angiopoietin-1 and -2 on tumor growth and angiogenesis in human colon cancer. Cancer Res. 61, 1255-1259.

63. Etoh, T., Inoue, H., Tanaka, S., Barnard, G. F., Kitano, S., and Mori, M. (2001). Angiopoietin-2 is related to tumor angiogenesis in gastric carcinoma: possible in vivo regulation via induction of proteases. Cancer Res. 61, 2145-2153.

64. Hawighorst, T., Skobe, M., Streit, M., Hong, Y.-K., Velasco, P., Brown, L. F., Riccardi, L., Lange-Asschenfeldt, B., and Detmar, M. (2002). Activation of the Tie2 receptor by angiopoietin-1 enhances tumor vessel maturation and impairs squamous cell carcinoma growth. Am. J. Pathol. 160, 1381-1392.

65. Koga, K., Todaka, T., Morioka, M., Hamada, J., Kai, Y., Yano, S., Okamura, A., Takakura, N., Suda, T., and Ushio, Y. (2001). Expression of angiopoietin-2 in human glioma cells and its role for angiogenesis. Cancer Res. 61, 6248-6254.

66. Papetti, M., and Herman, I. M. (2002). Mechanisms of normal and tumor-derived angiogenesis. Am. J. Physiol. Cell Physiol. 282, C947-C970.

67. Weicner, N., Carroll, P. R., Flax, J., Blumenfeld, W., and Folkman, J. (1993). Tumor angiogenesis correlates with metastasis in invasive prostate cancer. Am. J. Pathol. 143, 401-409.

68. Southern, J. A., Young, D. F., Heaney, F., Gaumgartner, W., and Randall, R. E. (1991). Identification of an epitope on the P and V proteins of Simian virus 5 that distinguishes between two isolates with different biological characteristics. J. Gen. Virol. 72, 1551-1557.

69. Teichert-kuliszewska, K., Maisonpierre, P. C., Jones, N., Campbell, A. I. M., Master, Z., Bendeck, M. P., Alitalo, K., Dumont, D. J., Yancopoulos, G. D., and Stewart, D. J. (2001). Biological action of angiopoietin-2 in a fibrin matrix model of angiogenesis is associated with activation of Tie2. Cardiovasc. Res. 49, 659-670.

70. Kim, I., Moon, S.-O., Koh, K. N., Kim, H., Uhm, C.-S., Kwak, H. J., Kim, N.-G., and Koh, G. Y. (1999). Molecular cloning, expression, and characterization of angiopoietin-related protein. J. Biol. Chem. 274, 26523-26528.

71. Kim, I., Kim, J.-H., Ryu, Y. S., Jung, S. H., Nah, J. J., and Koh, G. Y. (2000). Characterization and expression of a novel alternatively spliced human angiopoietin-2. J. Biol. Chem. 275, 18550-18556.

72. Huang, Y.-Q., Li, J.-J. and Karpatkin, S. (2000). Identification of a family of alternatively spliced mRNA species of angiopoietin-1. Blood 95, 1993-1999.

73. Houck, K. A., Leung, D. W., Rowland, A. M., Winer, J., and Ferrara, N. (1992). Dual regulation of vascular endothelial growth factor bioavailability by genetic and proteolytic mechanisms. J. Biol. Chem. 267, 26031-26037.

74. Gamble, J. R., Drew, J., Trezise, L., Underwood, A., Parsons, M., Kasminkas, L., Rudge, J., Yancopoulos, G., and Vadas, M. A. (2000). Angiopoietin-1 is an antipermeability and antiinflammatory agent in vitro and targets cell junctions. Circ. Res. 87, 603-607.

75. Gospodarowicz, D., Abraham, J. A., and Schilling, J. (1989). Isolation and characterization of a vascular endothelial cell mitogen produced by pituitary-derived folliculo stellate cells. Proc. Natl. Acad. Sci. USA 86, 7311-7315.

76. Cohen, T., Gitay-Goren, H., Sharon, R., Shibuya, M., Halaban, R., Levi, B.-Z., and Neufeld, G. (1995). VEGF121, a vascular endothelial growth factor (VEGF) isoform lacking heparin binding ability, requires cell-surface heparan sulfates for efficient binding to the VEGF receptors of human melanoma cells. J. Biol. Chem. 270, 11322-11326.

77. Miralem, T., Steinberg, R., Price, D., and Avraham, H. (2001). VEGF(165) requires extracellular matrix components to induce mitogenic effects and migratory response in breast cancer cells. Oncogene 20, 5511-5524.

78. Kim, I., Moon, S.-O., Han, C.-Y., Pak, Y. K., Moon, S. K., Kim, J. J., and Koh, G. Y. (2001). The angiopoietin-tie2 system in coronary artery endothelium prevents oxidized low-density lipoprotein induced apoptosis. Cardiovasc. Res. 49, 872-881.

79. Kim, I., Moon, S.-O., Park, S. K., Chae, S. W., and Koh G. Y. (2001). Angiopoietin-1 reduces VEGF stimulated leukocyte adhesion to endothelial cells by reducing ICAM-1, VCAM-1, and E-selectin expression. Circ Res. 89, 477-479.

80. Kim, I., Oh, J.-L., Ryu, Y. S., So, J.-N., Sessa, W. C., Walsh, K., and Koh, G. Y. (2002). Angiopoietin-1 negatively regulates expression and activity of tissue factor in endothelial cells. FASEB J. 16, 126-128.

81. Kim, I., Ryu, Y. S., Kwak, H. J., Ahn, S. Y., Oh, J.-L., Yancopoulos, G. D., Gale, N. W., and Koh, G. Y. (2002). EphB ligand, ephrinB2, suppresses the VEGF- and angiopoietin 1-induced Ras/mitogen activated protein kinase pathway in venous endothelial cells. FASEB J. 16, 1126-1128.

82. Yu, Q., and Stamenkovic, I. (1999). Localization of matrix metalloproteinase 9 (MMP-9) to the cell surface provides a mechanism for CD44-mediated tumor invasion. Genes Dev. 13, 35-48.

83. Hungerford, J. E., and Little, C. D. (1999). Developmental biology of the vascular smooth muscle cell: building a multilayered vessel wall. J. Vasc. Res. 36, 2-27.

84. Gale, N. W., Thurston, G., Hackett, S. F., Renard, R., Wang, Q., McClain, J., Martin, C., Witte, C., Wette, M. H., Jackson, D., Suri, C., Campochiaro, P. A., Wiegand, S. J., and Yancopoulos, G. D. (2002). Angiopoietin-2 is required for postnatal angiogenesis and lymphatic patterning, and only the latter role is rescued by angiopoietin-1. Dev. Cell 3, 411-423.

85. Shyu, K. G., Manor, O., Manger, M., Yancopoulos, G. D., and Isner, J. M. (1998). Direct intramuscular injection of plasmid DNA encoding angiopoietin-1 but not angiopoietin-2 auguments revascularization in the rabbit ischemic hindlimb. Circulation 98, 2081-2087.

86. Kim, I., Kim, I. H., Moon, S. O., Kwak, H. J., Kim, N. G., and Koh, G. Y. (2000). Angiopoietin-2 at high concentration can enhance endothelial cell survival through the phosphatidylinositol 3'-kinase/Akt signal transduction pathway. Oncogene 19, 4549-4552.

87. Lander, A. D., and Selleck, S. B. (2000). The elusive functions of proteoglycans: in vivo veritas. J. Cell. Biol. 148, 227-232.

88. Iozzo, R. V. (1998). Matrix proteoglycans: from molecular design to cellular function. Annu. Rev. Biochem. 67, 609-652.

89. Iozzo, R. V., and San Antonio, J. D. (2001). Heparan sulfate proteoglycans: heavy hitters in the angiogenesis arena. J. Clin. Invest. 108, 349-355.

90. Fiedler, U., Krissl, T., Koidl, S., Weiss, C., Koblizek, T., Deutsch, U., Martiny-Baron, G., Marme, D., and Augustin, H. G. (2002). Angiopoietin-1 and angiopoietin-2 share the same binding domains in the Tie-2 receptor involving the first Ig-like loop and the EGF-like repeats. J. Biol. Chem.

91. Yu, Q., Toole, B. P., and Stamenkovic, I. (1997). Induction of apoptosis of metastatic mammary carcinoma cells in vivo by disruption of tumor cell surface CD44 function. J. Exp. Med. 186, 1985-1996.

92. Kontos, C. D., Stauffer, T. P., Yang, W. P., York, J. D., Huang, L., Blanar, M. A., Meyer, T., and Peters, K. G. (1998). Tyrosine 1101 of Tie2 is the major site of association of p85 and is required for activation of phosphatidylinositol 3-kinase and akt. Mol. Cell. Biol. 18, 4131-4140.

93. Folkman, J. (1990). What is the evidence that tumors are angiogenesis dependent? J. Natl. Cancer Inst. 82, 4-6.

94. Fidler, I. J., and Ellis, L. M. (1994). The implications of angiogenesis for the biology and therapy of cancer metastasis. Cell 79, 185-188.

95. Fidler, I. J. (1990). Critical factors in the biology of human cancer metastasis: twenty-eighth G.H.A. clowes memorial award lecture. Cancer Res. 50, 6130-6138.

96. Fidler, I. J. (2001). Angiogenic heterogeneity: regulation of neoplastic angiogenesis by the organ microenvironment. J. Natl. Cancer Inst. 93, 1040-1041.

97. Hamid Ali, S., O'Donnell, A. L., Balu, D., Pohl, M. B., Seyler, M. J., Mohamed, S., Mousa, S., and Dandona, P. (2000). Estrogen receptor-α in the inhibition of cancer growth and angiogenesis. Cancer Res. 60, 7094-7098.

98. Nokihara, H., Yanagawa, H., Nishioka, Y., Yano, S., Mukaida, N., Matsushima, K., and Sone, S. (2000). Natural killer cell-dependent suppression of systemic spread of human lung adenocarcinoma cells by monocyte chemoattractant protein-1 gene transfection in severe combined immunodeficient mice. Cancer Res. 60, 7002-7007.

99. Lindahl, P., Johansson, B. R., Leveen, P., and Betsholtz, C. (1997). Pericyte loss and microaneurysm formation in PDGF-B-deficient mice. Science 277, 242-245.

100. Lindahl, P., Hellstrom, M., Kalen, M., and Betsholtz, C. (1998). Endothelial-perivascular cell signaling in vascular development: lessons from knockout mice. Curr. Opin. Lipidol. 9, 407-411.

101. Murray, C. (1995). Tumour dormancy: not so sleepy after all. Nat. Med. 1, 117-118.

102. Cross, M. J., and Claesson-Welsh, L. (2001). FGF and VEGF function in angiogenesis: signaling pathways, biological responses and therapeutic inhibition. Trends Phar. Sci. 22, 201-207.

103. Gengrinovitch, S., Berman, B., David, G., Witte, L., Neufeld, G., and Ron, D. (1999). Glypican-1 is a VEGF165 binding proteoglycan that acts as an extracellular chaperone for VEGF165. J. Biol. Chem. 274, 10816-10822.

104. Li, J., Shworak, N. W., and Simons, M. (2002). Increased responsiveness of hypoxic endothelial cells to FGF2 is mediated by HIF-1 α-dependent regulation of enzymes involved in synthesis of heparan sulfate FGF2-binding sites. J. Cell Sci. 115, 1951-1959.

105. Neufeld, G., Cohen, T., Gengrinovitch, S., and Poltorak, Z. (1999). Vascular endothelial growth factor (VEGF) and its receptors. FASEB J. 13, 9-22.

106. Nagase, H. (1997). Activation mechanisms of matrix metalloproteinases. Biol. Chem. 378, 151-160.

107. Park, J. E., Keller, G. A., and Ferrara, N. (1993). The vascular endothelial growth factor (VEGF) isoforms: differential deposition into the subepithelial extracellular matrix and bioactivity of extracellular matrix-bound VEGF. Mol. Biol. Cell 4, 1317-1326.

108. Pepper, M. S. (1997). Transforming growth factor-beta: vasculogenesis, angiogenesis, and vessel wall integrity. Cytokine Growth Factor Rev. 8, 21-43.

109. Xu, Y., and Yu, Q. (2003). E-cadherin negatively regulates CD44-hyaluronan interaction and CD44-mediated tumor invasion and branching morphogenesis. J. Biol. Chem. In Press.

110. Poltorak, Z., Cohen, T., Sivan, R., Kandelis, Y., Spira, G., Vlodavsky, I., Keshet, E., and Neufeld, G. (1997). VEGF145, a secreted vascular endothelial growth factor isoform that binds to extracellular matrix. J. Biol. Chem. 272, 7151-7158.

111. Robinson, C. J., and Stringer, S. E. (1999). The splice variants of vascular endothelial growth factor (VEGF) and their receptors. J. Cell Sci. 114, 853-865.

112. Ruhrberg, C. (2001). Endogenous inhibitors of angiogenesis. J. Cell Sci. 114, 3215-3216.

113. Saaristo, A., Karpanen, T., and Alitalo, K. (2000). Mechanisms of angiogenesis and their use in the inhibition of tumor growth and metastasis. Oncogene 19, 6122-6129.

114. Maeshima, Y., Sudhakar, A., Lively, J. C., Ueki, K., Kharbanda, S., Kahn, C. R., Sonenberg, N., Hynes, R. O., and Kalluri, R. (2002). Tumstatin, an endothelial cell-specific inhibitor of protein synthesis. Science 295, 140-143.

115. O'Reilly, M. S. et al. (1994). Angiostatin: a novel angiogenesis inhibitor that mediates the suppression of metastases by a lewis lung carcinoma. Cell 79, 315-328.

116. O'Reilly, M. S., Pirie-Shepherd, S., Lane, W. S., and Folkman, J. (1999). Antiangiogenic activity of the cleaved conformation of the serpin antithrombin. Science 285, 1926-1928.

117. Yi, M., and Ruoslahti, E. (2001). A fibronectin fragment inhibits tumor growth, angiogenesis, and metastasis. Proc. Natl. Acad. Sci. USA 98, 620-624.

118. Johnson, L. L., Dyer, R., and Hupe, D. J. (1998). Matrix metalloproteinases. Curr. Opin. Chem. Biol. 2, 466-471.

119. Rastinejad, F., Polverini, P. J., and Bouck, N. P. (1989). Regulation of the activity of a new inhibitor of angiogenesis by a cancer suppressor gene. Cell 56, 345-355.

120. Vu, T. H., Shipley, J. M., Bergers, G., Berger, J. E., Helms, J. A., Hanahan, D., Shapiro, S. D., Senior, R. M., and Werb, Z. (1998). MMP-9/gelatinase B is a key regulator of growth plate angiogenesis and apoptosis of hypertrophic chondrocytes. Cell 93, 411-422.

121. Davda, J., and Labhasetwar, V. (2001). An update on angiogenesis therapy. Crit. Rev. Eukaryot. Gene Expr. 11, 1-21.

122. Vajkoczy, P., Farhadi, M., Gaumann, A., Heidenreich, R., Erber, R., Wunder, A., Tonn, J. C., Menger, M. D., and Breier, G. (2002). Microtumor growth initiates angiogenic sprouting with simultaneous expression of VEGF, VEGF receptor-2, and angiopoietin-2. J. Clin. Invest. 109, 777-785.

123. Bloemendal, H. J., Logtenberg, T., and Voest, E. E. (1999). New strategies in anti-vascular cancer therapy. Eur. J. Clin. Invest. 29, 802-809.

124. Harfouche, R., Hassessian, H. M., Guo, Y., Faivre, V., Srikant, C. B., Yancopoulos, G. D., and Hussain, S. N. (2002). Mechanisms which mediate the antiapoptotic effects of angiopoietin-1 on endothelial cells. Microvasc. Res. 64, 135-147.

125. Hiraoka, N., Allen, E., Apel, I. J., Gyetko, M. R., and Weiss, S. J. (1998). Matrix metalloproteinases regulate neovascularization by acting as pericellular fibrinolysins. Cell 95, 365-377.

126. Bergers, G., Brekken, R., McMahon, G., Vu, T. H., Itoh, T., Tamaki, K., Tanzawa, K., Thorpe, P., Itohara, S., Werb, Z., and Hanahan, D. (2000). Matrix metalloproteinase-9 triggers the angiogenic switch during carcinogenesis. Nat. Cell Biol. 2, 737-744.

127. Itoh, T., Tanioka, M., Yoshida, H., Yoshioka, T., Nishimoto, H., and Itohara, S. (1998). Reduced angiogenesis and tumor progression in gelatinase A-deficient mice. Cancer Res. 58, 1048-1051.

128. Fang, J., Shing, Y., Wiederschain, D., Yan, L., Butterfield, C., Jackson, G., Harper, J., Tamvakopoulos, G., and Moses, M. A. (2000). Matrix metalloproteinase-2 is required for the switch to the angiogenic phenotype in a tumor model. Proc. Natl. Acad. Sci. USA 97, 3884-3889.

129. Visconti, R. P., Richardson, C. D., and Sato, T. N. (2002). Orchestration of angiogenesis and arteriovenous contribution by angiopoietins and vascular endothelial growth factor (VEGF). PNAS. 99, 8219-8224.

130. Pfeifer, A., Kessler, T., Silletti, S., Cheresh, D. A., and Verma, I. M. (2000). Suppression of angiogenesis by lentiviral delivery of PEX, a noncatalytic fragment of matrix metalloproteinase 2. Proc. Natl. Acad. Sci. USA 97, 12227-12232.

131. Sternlicht, M. D., and Werb, Z. (2001). How matrix metalloproteinases regulate cell behavior. Annu. Rev. Cell Dev. Biol. 17, 463-516.

132. Silletti, S., Kessler, T., Goldberg, J., Boger, D. L., and Cheresh, D. A. (2001). Disruption of matrix metalloproteinase 2 binding to integrin $\alpha v\beta 3$ by an organic molecule inhibits angiogenesis and tumor growth in vivo. PNAS 98, 119-124.

133. Holmgren, L., O'Reilly, M. S., and Folkman, J. (1995). Dormancy of micrometastases: balanced proliferation and apoptosis in the presence of angiogenesis suppression. Nature Med. 1, 149-153.

134. Sipes, J. M., Krutzsch, H. C., Lawler, J., and Roberts, D. D. (1999). Cooperation between thrombospondin-1 type 1 repeat peptides and $\alpha x\beta 3$ integrin ligands to promote melanoma cell spreading and focal adhesion kinase phosphorylation. J. Biol. Chem. 274, 22755-22762.

135. Saaristo, A., Karpanen, T., and Alitalo, K. (2000). Mechanisms of angiogenesis and their use in the inhibition of tumor growth and metastasis. Oncogene 19, 6122-6129.

136. Uemura, A., Ogawa, M., Hirashima, M., Fujiwara, T., Koyama, S., Takagi, H., Honda, Y., Wiegand, S. J., Yancopoulos, G. D., and Nishikawa, S. I. (2002). Recombinant angiopoietin-1 restores higher-order architecture of growing blood vessels in mice in the absence of mural cells. J. Clin. Invest. 110, 1619-1628.

137. Yu, Q., and Stamenkovic, I. (2000). Cell surface-localized matrix metalloproteinase-9 proteolytically activates TGF-$\beta$ and promotes tumor invasion and angiogenesis. Genes Dev. 14, 163-176.

138. McFall, A. J., and Rapraeger, A. C. (1998). Characterization of the high affinity cell-binding domain in the cell surface proteoglycan syndecan-4. J. Biol. Chem. 273, 28270-28276.

139. Olson, M. W., Toth, M., Gervasi, D. C., Sado, Y., Ninomiya, Y., and Fridman, R. (1998). High affinity binding of latent matrix metalloproteinase-9 to the $\alpha 2$(IV) chain of collagen IV. J. Biol. Chem. 273, 10672-10681.

140. Brooks, P. C., Stromblad, S., Sanders, L. C., von Schalscha, T. L., Aimes, R. T., Stetler-Stevenson, W. G., Quigley, J. P., and Cheresh, D. A. (1996). Localization of matrix metalloproteinase MMP-2 to the surface of invasive cells by interaction with integrin $\alpha v\beta 3$. Cell 85, 683-693.

141. Moyon, D., Pardanaud, L., Yuan, L., Breant, C., and Eichmann, A. (2001). Selective expression of angiopoietin 1 and 2 in mesenchymal cells surrounding veins and arteries of the avian embryo. Mech. Dev. 106, 133-136.

142. Wong, A. L., Haroon, Z. A., Werner, S., Dewhirst, M. W., Greenberg, C. S., and Peters, K. G. (1997). Tie2 expression and phosphorylation in angiogenic and quiescent adult tissues. Circ. Res. 81, 567-574.

143. Shim, W. S. N., The, M., Mack, P. O. P., and Ge, R. (2001). Inhibition of angiopoietin-1 expression in tumor cells by an antisense RNA approach inhibited xenograft tumor growth in immunodeficient mice. Int. J. Cancer 94, 6-15.

144. Weidner, N. (1993). Tumor angiogenesis: review of current applications in tumor prognostication. Semin. Diagn. Pathol. 10, 302-313.

145. Shim, W. S. N., The, M., Bapna, A., Kim, I., Koh, G. Y., Mack, P. O. P. and Ge, R. (2002). Angiopoietin 1 promotes tumor angiogenesis and tumor vessel plasticity of human cervical cancer in mice. Exp. Cell Res. 279, 299-309.

146. Joussen, A. M., Poulaki, V., Tsujikawa, A., Qin, W., Qaum, T., Xu, Q., Moromizato, Y., Bursell, S.-E., Wiegand, S. J., Rudge, J., Ioffe, E., Yancopoulos, G. D., and Adamis, A. P. (2002). Suppression of diabetic retinopathy with angiopoietin-1. Am. J. Pathol. 160, 1683-1693.

147. Hattori, K., Dias, S., Heissig, B., Hackett, N. R., Lyden, D., Tateno, M., Hicklin, D. J., Zhu, Z., Witte, L., Crystal, R. G., Moore, M. A. S., and Rafii, S. (2001). Vascular endothelial growth factor and angiopoietin-1 stimulate postnatal hematopoiesis by recruitment of vasculogenic and hematopoietic stem cells. J. Exp. Med. 193, 1005-1014.

148. Davis, S., Papadopoulos, N., Aldrich, T. H., Maisonpierre, P. C., Huang, T., Kovac, L., Xu, A., Leidich, R., Radziejewska, E., Rafique, A., Goldberg, J., Jain, V., Bailey, K., Karow, M., Fandl, J., Samuelsson, S. J., Loffe, E., Rudge, J. S., Daly, T. J., Radziejewski, C., and Yancopoulos, G. D. (2002). Angiopoietins have distinct modular domains essential for receptor binding, dimerization and superclustering. Nature Struct. Biol. 10, 38-44.

The disclosures of each and every patent, patent application, and publication cited herein are hereby incorporated herein by reference in their entirety. The appended sequence listing is also hereby incorporated herein by reference in its entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A pharmaceutical composition comprising a pharmaceutically acceptable carrier, wherein said composition comprises:
    a therapeutically effective amount of an extracellular matrix (ECM) binding domain of an Ang-1 protein consisting of SEQ ID NO:1.

2. A pharmaceutical composition comprising:
    a) a pharmaceutically acceptable carrier; and
    b) a therapeutically effective amount of an Ang-1 fragment consisting of SEQ ID NO:1, wherein said fragment has antagonist activity.

* * * * *